US011078540B2

(12) United States Patent
Garraway et al.

(10) Patent No.: US 11,078,540 B2
(45) Date of Patent: Aug. 3, 2021

(54) METHODS OF DIAGNOSING AND TREATING CANCER IN PATIENTS HAVING OR DEVELOPING RESISTANCE TO A FIRST CANCER THERAPY

(71) Applicants: Levi A. Garraway, Newton, MA (US); Cory M. Johannessen, Roslindale, MA (US)

(72) Inventors: Levi A. Garraway, Newton, MA (US); Cory M. Johannessen, Roslindale, MA (US)

(73) Assignees: DANA-FARBER CANCER INSTITUTE, INC., Boston, MA (US); BROAD INSTITUTE, INC., Cambridge, MA (US)

( * ) Notice: Subject to any disclaimer, the term of this patent is extended or adjusted under 35 U.S.C. 154(b) by 531 days.

(21) Appl. No.: 15/480,126

(22) Filed: Apr. 5, 2017

(65) Prior Publication Data
US 2017/0268069 A1 Sep. 21, 2017

Related U.S. Application Data

(62) Division of application No. 13/583,056, filed as application No. PCT/US2011/027689 on Mar. 9, 2011, now abandoned.

(60) Provisional application No. 61/415,569, filed on Nov. 19, 2010, provisional application No. 61/326,021, filed on Apr. 20, 2010, provisional application No. 61/312,519, filed on Mar. 10, 2010, provisional application No. 61/312,193, filed on Mar. 9, 2010.

(51) Int. Cl.
*C12Q 1/6886* (2018.01)
*A61K 31/4184* (2006.01)
*C12N 9/12* (2006.01)

(52) U.S. Cl.
CPC ........ *C12Q 1/6886* (2013.01); *A61K 31/4184* (2013.01); *C12N 9/12* (2013.01); *C12N 9/1205* (2013.01); *C12Y 207/11024* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 6,310,060 B1 | 10/2001 | Barrett et al. |
| 6,440,966 B1 | 8/2002 | Barrett et al. |
| 6,455,582 B1 | 9/2002 | Tecle |
| 6,469,004 B1 | 10/2002 | Barrett et al. |
| 6,492,363 B2 | 12/2002 | Barrett et al. |
| 6,506,798 B1 | 1/2003 | Barrett et al. |
| 6,545,030 B1 | 4/2003 | Barrett et al. |
| 6,750,217 B2 | 6/2004 | Barrett et al. |
| 6,770,778 B2 | 8/2004 | Barrett et al. |
| 6,821,963 B2 | 11/2004 | Barrett et al. |
| 6,835,749 B2 | 12/2004 | Tecle |
| 6,891,066 B2 | 5/2005 | Rewcastle et al. |
| 6,960,614 B2 | 11/2005 | Barrett et al. |
| 6,989,451 B2 | 1/2006 | Zhang et al. |
| 7,019,033 B2 | 3/2006 | Barrett et al. |
| 7,078,438 B2 | 7/2006 | Rewcastle et al. |
| 7,144,907 B2 | 12/2006 | Wallace et al. |
| 7,160,915 B2 | 1/2007 | Barrett et al. |
| 7,169,816 B2 | 1/2007 | Barrett et al. |
| 7,173,136 B2 | 2/2007 | Hennequin |
| 7,230,099 B2 | 6/2007 | Wallace et al. |
| 7,232,826 B2 | 6/2007 | Velaparthi et al. |
| 7,253,199 B2 | 8/2007 | Arkinstall et al. |
| 7,271,178 B2 | 9/2007 | Wallace et al. |
| 7,273,877 B2 | 9/2007 | Black et al. |
| 7,307,071 B2 | 12/2007 | Lyons et al. |
| 7,371,869 B2 | 5/2008 | Goodnow, Jr. et al. |
| 7,378,423 B2 | 5/2008 | Kawasaki et al. |
| 7,411,001 B2 | 8/2008 | Barrett et al. |
| 7,423,150 B2 | 9/2008 | Costales et al. |
| 8,415,382 B2 | 4/2013 | Costales et al. |
| 2002/0022647 A1 | 2/2002 | Barrett et al. |
| 2003/0004193 A1 | 1/2003 | Barrett et al. |

(Continued)

FOREIGN PATENT DOCUMENTS

| | | |
|---|---|---|
| AT | 404556 B | 12/1998 |
| AT | 277895 T | 10/2004 |

(Continued)

OTHER PUBLICATIONS

Azam et al.; "Mechanisms of Autoinhibition and STI-571/Imatinib Resistance Revealed by Mutagenesis of BCR-ABL"; Cell, vol. 112; Mar. 21, 2003; pp. 831-843.

(Continued)

*Primary Examiner* — Jeffrey S Lundgren
*Assistant Examiner* — Michael J Schmitt
(74) *Attorney, Agent, or Firm* — Brinks Gilson & Lione; Yuezhong Feng

(57) ABSTRACT

A method of identifying a subject having cancer who is likely to benefit from treatment with a combination therapy with a RAF inhibitor and a second inhibitor is provided. A method of treating cancer in a subject in need thereof is also provided and includes administering to the subject an effective amount of a RAF inhibitor and an effective amount of a second inhibitor, wherein the second inhibitor is a MEK inhibitor, a CRAF inhibitor, a CrkL inhibitor or a TPL2/COT inhibitor. A method of identifying a kinase target that confers resistance to a first inhibitor is also provided.

12 Claims, 24 Drawing Sheets
Specification includes a Sequence Listing.

(56) References Cited

U.S. PATENT DOCUMENTS

| | | |
|---|---|---|
| 2003/0149015 A1 | 8/2003 | Barrett et al. |
| 2003/0216460 A1 | 11/2003 | Wallace et al. |
| 2004/0171632 A1 | 9/2004 | Gowan et al. |
| 2005/0004186 A1 | 1/2005 | Barrett et al. |
| 2005/0049276 A1 | 3/2005 | Kaufman et al. |
| 2005/0049429 A1 | 3/2005 | Barrett et al. |
| 2005/0059710 A1 | 3/2005 | Barrett et al. |
| 2005/0130943 A1 | 6/2005 | Wallace et al. |
| 2005/0130976 A1 | 6/2005 | Wallace et al. |
| 2005/0153942 A1 | 7/2005 | Wallace et al. |
| 2005/0187247 A1 | 8/2005 | Berger et al. |
| 2005/0250782 A1 | 11/2005 | Marlow et al. |
| 2005/0256123 A1 | 11/2005 | Marlow et al. |
| 2006/0030610 A1 | 2/2006 | Koch et al. |
| 2006/0041146 A1 | 2/2006 | Chu et al. |
| 2006/0079526 A1 | 4/2006 | Wrasidlo et al. |
| 2006/0106225 A1 | 5/2006 | Wallace et al. |
| 2006/0189668 A1 | 8/2006 | Wallace et al. |
| 2006/0189808 A1 | 8/2006 | Wallace et al. |
| 2006/0194802 A1 | 8/2006 | Abdellaoui et al. |
| 2006/0270643 A1 | 11/2006 | Chang et al. |
| 2007/0049591 A1 | 3/2007 | Pinkerton et al. |
| 2007/0105859 A1 | 5/2007 | Isshiki et al. |
| 2007/0112038 A1 | 5/2007 | Marlow et al. |
| 2007/0191346 A1 | 8/2007 | Hennequin |
| 2007/0197617 A1 | 8/2007 | Chen et al. |
| 2007/0238710 A1 | 10/2007 | Yan et al. |
| 2007/0244164 A1 | 10/2007 | Yan et al. |
| 2007/0287709 A1 | 12/2007 | Goutopoulos et al. |
| 2007/0287737 A1 | 12/2007 | Goutopoulos et al. |
| 2007/0293544 A1 | 12/2007 | Abel et al. |
| 2007/0293555 A1 | 12/2007 | Arkinstall et al. |
| 2007/0299103 A1 | 12/2007 | Abel et al. |
| 2008/0058340 A1 | 3/2008 | Maderna et al. |
| 2008/0081821 A1 | 4/2008 | Savy et al. |
| 2008/0085886 A1 | 4/2008 | Savy et al. |
| 2008/0166359 A1 | 7/2008 | Lamb |
| 2008/0188453 A1 | 8/2008 | Adams et al. |
| 2009/0047675 A1 | 2/2009 | Roberts |
| 2009/0163525 A1 | 6/2009 | Aquila et al. |
| 2013/0224195 A1 | 8/2013 | Costales et al. |

FOREIGN PATENT DOCUMENTS

| | | |
|---|---|---|
| AT | 302193 T | 9/2005 |
| AT | 302761 T | 9/2005 |
| AT | 309205 T | 11/2005 |
| AT | 310567 T | 12/2005 |
| AT | 311363 T | 12/2005 |
| AT | 344791 T | 11/2006 |
| AT | 383360 T | 1/2008 |
| AU | 2001273498 B2 | 1/2002 |
| AU | 757046 B2 | 1/2003 |
| AU | 2002359291 B2 | 5/2003 |
| AU | 2002347360 A1 | 6/2003 |
| AU | 2002365665 A1 | 6/2003 |
| AU | 2002365899 B2 | 6/2003 |
| AU | 2003220202 A1 | 9/2003 |
| AU | 756586 C | 1/2004 |
| AU | 2003275282 A1 | 4/2004 |
| AU | 2003278369 A1 | 6/2004 |
| AU | 2003287366 A8 | 6/2004 |
| AU | 2003291268 A1 | 6/2004 |
| AU | 2003286306 A1 | 7/2004 |
| AU | 2004270699 A1 | 3/2005 |
| AU | 2004293018 A1 | 6/2005 |
| AU | 2004293019 A1 | 6/2005 |
| AU | 2005252110 B2 | 12/2005 |
| AU | 2005265769 A1 | 2/2006 |
| AU | 2005274390 A1 | 2/2006 |
| AU | 2005276974 A1 | 3/2006 |
| AU | 2005284293 A1 | 3/2006 |
| AU | 2005298932 A1 | 5/2006 |
| AU | 2005311451 A1 | 6/2006 |
| AU | 2006272837 A1 | 2/2007 |
| AU | 2006299902 A1 | 4/2007 |
| AU | 2006302415 A1 | 4/2007 |
| AU | 2008202731 A1 | 7/2008 |
| BR | 0317254 | 11/2005 |
| BR | 0412851 | 10/2006 |
| BR | 0414111 | 10/2006 |
| BR | 0416692 | 1/2007 |
| BR | 0511967 | 1/2008 |
| BR | 0513750 | 5/2008 |
| BR | 0514515 | 6/2008 |
| BR | 0515371 | 7/2008 |
| CA | 2 290 506 A1 | 1/1999 |
| CA | 2 290 509 A1 | 1/1999 |
| CA | 2 352 326 A1 | 6/2000 |
| CA | 2 349 467 A1 | 7/2000 |
| CA | 2 349 832 A1 | 7/2000 |
| CA | 2 355 374 A1 | 7/2000 |
| CA | 2 355 470 A1 | 7/2000 |
| CA | 2 416 685 A1 | 1/2002 |
| CA | 2 463 101 A1 | 5/2003 |
| CA | 2 466 762 A1 | 6/2003 |
| CA | 2 472 367 A1 | 7/2003 |
| CA | 2 473 545 A1 | 7/2003 |
| CA | 2 478 534 A1 | 9/2003 |
| CA | 2 509 405 A1 | 7/2004 |
| CA | 2 532 067 A1 | 2/2005 |
| CA | 2 537 321 A1 | 3/2005 |
| CA | 2 545 660 A1 | 6/2005 |
| CA | 2 546 353 A1 | 6/2005 |
| CA | 2 569 850 A1 | 12/2005 |
| CA | 2 575 232 A1 | 2/2006 |
| CA | 2 576 599 A1 | 2/2006 |
| CA | 2 578 283 A1 | 3/2006 |
| CA | 2 579 130 A1 | 3/2006 |
| CA | 2 582 247 A1 | 5/2006 |
| CA | 2 586 796 A1 | 6/2006 |
| CA | 2 587 178 A1 | 6/2006 |
| CA | 2 618 218 A1 | 2/2007 |
| CA | 2 608 201 A1 | 4/2007 |
| CA | 2 622 755 A1 | 4/2007 |
| CN | 1652792 A | 8/2005 |
| CN | 1874769 A | 12/2006 |
| CN | 1905873 A | 1/2007 |
| CN | 101006085 A | 7/2007 |
| CN | 101006086 A | 7/2007 |
| CN | 101023079 A | 8/2007 |
| CN | 101044125 A | 9/2007 |
| CN | 101065358 A | 10/2007 |
| CN | 101124199 A | 2/2008 |
| EE | 200100339 A | 10/2002 |
| EE | 200100373 A | 10/2002 |
| EE | 200100374 A | 12/2002 |
| EE | 200300030 A | 10/2004 |
| EP | 0 050 424 A1 | 4/1982 |
| EP | 0 084 796 B1 | 8/1983 |
| EP | 0 201 184 A2 | 12/1986 |
| EP | 0 237 362 A1 | 9/1987 |
| EP | 0 266 032 A1 | 5/1988 |
| EP | 1 438 295 A2 | 7/2004 |
| EP | 0 993 439 B1 | 9/2004 |
| EP | 1 467 965 A2 | 10/2004 |
| EP | 1 467 968 A2 | 10/2004 |
| EP | 0 258 017 B2 | 12/2004 |
| EP | 1 482 944 A2 | 12/2004 |
| EP | 1 545 529 A2 | 6/2005 |
| EP | 1 144 385 B1 | 8/2005 |
| EP | 1 144 394 B1 | 8/2005 |
| EP | 1 575 943 A1 | 9/2005 |
| EP | 1 578 346 A2 | 9/2005 |
| EP | 1 578 736 A1 | 9/2005 |
| EP | 1 140 291 B1 | 11/2005 |
| EP | 1 144 371 B1 | 11/2005 |
| EP | 1 144 372 B1 | 11/2005 |
| EP | 1 673 339 A2 | 6/2006 |
| EP | 1 674 452 A1 | 6/2006 |
| EP | 1 682 138 A2 | 7/2006 |
| EP | 1 689 233 A2 | 8/2006 |
| EP | 0 993 437 B1 | 11/2006 |
| EP | 1 780 197 A1 | 5/2007 |

(56) References Cited

FOREIGN PATENT DOCUMENTS

| | | |
|---|---|---|
| EP | 1 799 656 A1 | 6/2007 |
| EP | 1 802 579 A1 | 7/2007 |
| EP | 1 803 821 A2 | 7/2007 |
| EP | 1 838 675 A1 | 10/2007 |
| EP | 1 761 528 B1 | 1/2008 |
| EP | 1 894 932 A1 | 3/2008 |
| EP | 1 912 636 A2 | 4/2008 |
| EP | 1 922 307 A2 | 5/2008 |
| EP | 1 781 649 B1 | 8/2008 |
| EP | 1 966 155 A1 | 9/2008 |
| EP | 1 967 516 A1 | 9/2008 |
| EP | 1 791 837 B1 | 8/2009 |
| EP | 1 651 214 B1 | 9/2009 |
| EP | 1 828 184 B1 | 9/2009 |
| EP | 1 934 174 B1 | 4/2011 |
| ES | 2 229 515 T3 | 4/2005 |
| ES | 2 247 859 T3 | 3/2006 |
| ES | 2 249 060 T3 | 3/2006 |
| ES | 2 251 851 T3 | 5/2006 |
| ES | 2 252 996 T3 | 5/2006 |
| FR | 2 650 840 A1 | 2/1991 |
| GB | 2323845 | 10/1998 |
| JP | 2000-204075 A | 7/2000 |
| JP | 2000-204077 A | 7/2000 |
| JP | 2000-204079 A | 7/2000 |
| JP | 2000-212157 A | 8/2000 |
| JP | 2002-509536 A | 3/2002 |
| JP | 2002-511092 A | 4/2002 |
| JP | 2002-532570 A | 10/2002 |
| JP | 2002-534497 A | 10/2002 |
| JP | 2002-534510 A | 10/2002 |
| JP | 2002-534515 A | 10/2002 |
| JP | 2004-504294 A | 2/2004 |
| JP | 2005-508972 A | 4/2005 |
| JP | 2005-515251 A | 5/2005 |
| JP | 2005-515253 A | 5/2005 |
| JP | 2005-526008 A | 9/2005 |
| JP | 2005-526076 A | 9/2005 |
| JP | 2006-083133 A | 3/2006 |
| JP | 2006-508944 A | 3/2006 |
| JP | 2006-516967 A | 7/2006 |
| JP | 3811775 B2 | 8/2006 |
| JP | 2006-528621 A | 12/2006 |
| JP | 2007-504241 A | 3/2007 |
| JP | 2007-511614 A | 5/2007 |
| JP | 2007-511615 A | 5/2007 |
| JP | 2008-501631 A | 1/2008 |
| JP | 2008-509950 A | 4/2008 |
| JP | 2008-510839 A | 4/2008 |
| JP | 2008-513397 A | 5/2008 |
| JP | 2008-517024 A | 5/2008 |
| JP | 4090070 B2 | 5/2008 |
| JP | 2008-520615 A | 6/2008 |
| JP | 2008-521858 A | 6/2008 |
| JP | 4131741 B2 | 8/2008 |
| JP | 2008-201788 A | 9/2008 |
| KR | 10-2007-026343 | 3/2007 |
| KR | 10-2007-034581 | 3/2007 |
| KR | 10-2007-034635 | 3/2007 |
| KR | 10-2007-041752 | 4/2007 |
| KR | 10-2007-043895 | 4/2007 |
| KR | 10-2007-067727 | 6/2007 |
| KR | 10-2008-019236 | 3/2008 |
| KR | 10-2008-050601 | 6/2008 |
| KR | 10-2008-068637 | 7/2008 |
| RU | 2300528 C2 | 6/2007 |
| TR | 2001 01871 T2 | 10/2001 |
| TR | 2001 02029 T2 | 11/2001 |
| TR | 2001 02030 T2 | 1/2002 |
| TW | 396149 B | 7/2000 |
| TW | 592692 B | 6/2004 |
| WO | WO 91-02087 A1 | 2/1991 |
| WO | WO 92-15712 A1 | 9/1992 |
| WO | WO 94-09699 A1 | 5/1994 |
| WO | WO 95-06128 A2 | 3/1995 |
| WO | WO 99-01421 A1 | 1/1999 |
| WO | WO 99-01426 A1 | 1/1999 |
| WO | WO 2000-037141 A1 | 6/2000 |
| WO | WO 2000-041994 A1 | 7/2000 |
| WO | WO 2000-042002 A1 | 7/2000 |
| WO | WO 2000-042003 A1 | 7/2000 |
| WO | WO 2000-042022 A1 | 7/2000 |
| WO | WO 2000-042029 A1 | 7/2000 |
| WO | WO 2002-006213 A2 | 1/2002 |
| WO | WO 2003-035626 A2 | 5/2003 |
| WO | WO 2003-047523 A2 | 6/2003 |
| WO | WO 2003-047583 A1 | 6/2003 |
| WO | WO 2003-047585 A1 | 6/2003 |
| WO | WO 2003-062189 A1 | 7/2003 |
| WO | WO 2003-062191 A1 | 7/2003 |
| WO | WO 2003-077855 A2 | 9/2003 |
| WO | WO 2004-030620 A2 | 4/2004 |
| WO | WO 2004-041185 A2 | 5/2004 |
| WO | WO 2004-041811 A1 | 5/2004 |
| WO | WO 2004-044219 A2 | 5/2004 |
| WO | WO 2004-056789 A1 | 7/2004 |
| WO | WO 2004/080464 A1 | 9/2004 |
| WO | WO 2005-000818 A1 | 1/2005 |
| WO | WO 2005-007616 A1 | 1/2005 |
| WO | WO 2005-009975 A2 | 2/2005 |
| WO | WO 2005-023759 A2 | 3/2005 |
| WO | WO 2005-028426 A1 | 3/2005 |
| WO | WO 2005-051301 A2 | 6/2005 |
| WO | WO 2005-051302 A2 | 6/2005 |
| WO | WO 2005-082891 A1 | 9/2005 |
| WO | WO 2005-121142 A1 | 12/2005 |
| WO | WO 2006-011466 A1 | 2/2006 |
| WO | WO 2006-018188 A2 | 2/2006 |
| WO | WO 2006-024034 A1 | 3/2006 |
| WO | WO 2006-024836 A | 3/2006 |
| WO | WO 2006-029862 A1 | 3/2006 |
| WO | WO 2006-045514 A1 | 5/2006 |
| WO | WO 2006-056427 A1 | 6/2006 |
| WO | WO 2006-058752 A1 | 6/2006 |
| WO | WO 2006-133417 A1 | 12/2006 |
| WO | WO 2007-014011 A2 | 2/2007 |
| WO | WO 2007-025090 A2 | 3/2007 |
| WO | WO 2007-044084 A2 | 4/2007 |
| WO | WO 2007-044515 A1 | 4/2007 |
| WO | WO 2007-071951 A1 | 6/2007 |
| WO | WO 2007-096259 A1 | 8/2007 |
| WO | WO 2007-121269 A2 | 10/2007 |
| WO | WO 2007-121481 A2 | 10/2007 |
| WO | WO 2007-123936 A1 | 11/2007 |
| WO | WO 2007-123939 A2 | 11/2007 |
| WO | WO 2008-020203 A | 2/2008 |
| WO | WO 2008-021389 A2 | 2/2008 |
| WO | WO 2008-024724 A1 | 2/2008 |
| WO | WO 2008-024725 A1 | 2/2008 |
| WO | WO 2008-028141 A | 3/2008 |
| WO | WO 2008-055236 A2 | 5/2008 |
| WO | WO 2008-067481 A1 | 6/2008 |
| WO | WO 2008-076415 A1 | 6/2008 |
| WO | WO 2008-120004 A1 | 10/2008 |
| WO | WO-2009018238 A1 * | 2/2009 ........... A61K 31/352 |
| WO | WO 2010-068738 A1 | 6/2010 |
| WO | WO 2011/047238 A1 | 4/2011 |
| ZA | 98-05726 | 6/1998 |
| ZA | 98-05728 | 6/1998 |
| ZA | 2001-005219 | 6/2001 |
| ZA | 2001-005224 | 6/2001 |

OTHER PUBLICATIONS

Banerjee, A. et al., "Diverse Toll-like receptors utilize Tpl2 to activate extracellular signal-regulated kinase (ERK) in hemopoietic cells," Proc Natl Acad Sci , vol. 103, Feb. 28, 2006, pp. 3274-3279.
Barbie, D. A. et al., "Systematic RNA interference reveals that oncogenic KRAS-driven cancers require TBK1," Nature, vol. 462, Nov. 5, 2009, pp. 108-112.
Beroukhim, R. et al., "The landscape of somatic copy-number alteration across human cancers," Nature, vol. 463, Feb. 18, 2010, pp. 899-905.

(56) References Cited

OTHER PUBLICATIONS

Birge, R. B. et al., "Crk and CrkL adaptor proteins: networks for physiological and pathological signaling," Cell Communication Signaling, vol. 7:13, 2009, 23 pages.
Boehm, J. S. et al. "Integrative Genomic Approaches Identify *IKBKE* as a Breast Cancer Oncogene," Cell, vol. 129, Jun. 15, 2007, pp. 1065-1079.
Chong, H. et al., "Regulation of Raf through Phosphorylation and N Terminus-C Terminus Interaction," J Biol Chem, vol. 278, No. 38, Issue of Sep. 19, 2003, pp. 36269-36276.
Daub, H. et al., "Strategies to Overcome Resistance to Targeted Protein Kinase Inhibitors," Nature Reviews, Drug Discovery, vol. 3, Dec. 2004, pp. 1001-1010.
Davies, H. et al., "Mutations of the *BRAF* gene in human cancer," Nature, vol. 417, Jun. 27, 2002, pp. 949-954.
Dougherty, M. K. et al., "Regulation of Raf-1 by Direct Feedback Phosphorylation," Molecular Cell, vol. 17, Jan. 21, 2005, pp. 215-224.
Dumaz, N. et al. "In Melanoma, *RAS* Mutations Are Accompanied by Switching Signaling from BRAF to CRAF and Disrupted Cyclic AMP Signaling," Cancer Research, vol. 66, 2006, pp. 9483-9491.
Emery, C. M. et al., "MEK1 mutations confer resistance to MEK and B-RAF inhibition," Proc. Natl Acad. Sci. USA, vol. 106, No. 48, Dec. 2009, pp. 20411-20416.
Engelman, J. A. et al., "*MET* Amplification Leads to Gefitinib Resistance in Lung Cancer by Activating ERBB3 Signaling," Science, vol. 316, 2007, pp. 1039-1043.
Flaherty, K. T. et al., Inhibition of Mutated, Activated BRAF in Metastatic Melanoma, N. Engl. J. Med., vol. 363, Aug. 2010, pp. 809-819.
Frémin et al.; "From basic research to clinical development of MEK½ inhibitors for cancer therapy"; Journal of Hematology & Oncology 3:8; pp. 1-11; Feb. 11, 2010.
George, D. et al., "Discovery of thienol[2,3-c]pyridines as potent COT inhibitors," Bioorganic & Medicinal Chemistry Letters, vol. 18, 2008, pp. 4952-4955.
Gorre, M. E. et al., "Clinical Resistance to STI-571 Cancer Therapy Caused by BCR-ABL Gene Mutation or Amplification," Science, vol. 293, 2001, pp. 876-880.
Hatzivassiliou, G. et al., "RAF inhibitors prime wild-type RAF to activate the MAPK pathway and enhance growth," Nature, vol. 464, Mar. 18, 2010, pp. 431-435.
Heidorn, S.J. et al., "Kinase-Dead BRAF and Oncogenic RAS Cooperate to Drive Tumor Progression through CRAF," Cell, vol. 140, 2010, pp. 209-221.
Heinrich, M. C. et al., "Molecular Correlates of Imatinib Resistance in Gastrointestinal Stromal Tumors," J. Clin. Oncol., vol. 24, No. 29, Oct. 2006, pp. 4764-4774.
Hirata, K. et al., "Inhibition of Tumor Progression Locus 2 Protein Kinase Suppresses Receptor Activator of Nuclear Factor-κB Ligand-Induced Osteoclastogenesis through Down-Regulation of the c-Fos and Nuclear Factor of Activated T Cells c1 genes," Biol. Pharm. Bull., vol. 33(1), Jan. 2010, pp. 133-137.
Hoeflich, K. P. et al., "Antitumor Efficacy of the Novel RAF Inhibitor GDC-0879 Is Predicted by BRAF $^{V600E}$ Mutational Status and Sustained Extracellular Signal-Regulated Kinase/Mitogen-Activated Protein Kinase Pathway Suppression," Cancer Res. 69, 2009, pp. 3042-3051.
Holz et al.; "A Human cDNA Expression Library in Yeast Enriched for Open Reading Frames"; Genome Research, vol. 11; Oct. 1, 2001; pp. 1730-1735.
Infante, J. R. et al., "Safety and efficacy results from the first-in-human study of the oral MEK ½ inhibitor GSK1120212," J. Clin. Oncol., vol. 28, No. 15 (suppl.), 2010, p. 2503 (Abstract).
Johannessen, Cory M. et al., "COT drives resistance to RAF inhibition through MAP kinase pathway reactivation," Research Letter, doi:10.1038/nature09627, 2010, 7 pages.
Jones, Steven JM et al., "Evolution of an adenocarcinoma in response to selection by targeted kinase inhibitors," Genome Biology, 2010, 11:R82, 12 pages.
Karasarides, M. et al. "B-RAF is a therapeutic target in melanoma," Oncogene 23, 2004, pp. 6292-6298.
Karreth, F.A. et al., "C-Raf Inhibits MAPK Activation and Transformation by B-Raf$^{V600E}$," Molecular Cell, vol. 36, Nov. 13, 2009, pp. 477-486.
Lee, K. M. et al., "Tpl2 Is a Key Mediator of Arsenite-Induced Signal Transduction," Cancer Research, vol. 69, 2009, pp. 8043-8049.
Lundberg, A. S. et al. "Immortalization and transformation of primary human airway epithelial cells by gene transfer," Oncogene, vol. 21, 2002, pp. 4577-4586.
McDermott, U. et al., "Identification of genotype-correlated sensitivity to selective kinase inhibitors by using high-throughput tumor cell line profiling," Proc. National Acad. Sci. USA, vol. 104, No. 50, 2007, pp. 19936-19941.
McKay, M.M. et al., "Integrating signals from RTKs to ERK/MAPK," Oncogene, vol. 26, 2007, pp. 3113-3121.
Molhoek, Kerrington R. et al., "Synergistic inhibition of human melanoma proliferation by combination treatment with B-Raf inhibitor BAY43-9006 and mTOR inhibitor Rapamycin," Journal of Translational Medicine, vol. 3:39, 2005, 11 pages.
Montagut, C. et al., "Elevated CRAF as a Potential Mechanism of Acquired Resistance to BRAF Inhibition in Melanoma," Cancer Research, vol. 68, 2008, pp. 4853-4861.
Nazarian, Ramin et al., "Melanomas acquire resistance to B-RAF(V600E) inhibition by RTK or N-RAS upregulation," Research Letter, doi:10.1038/nature09626, 2010, 7 pages.
Poulikakos, P.I. et al., "RAF inhibitors transactivate RAF dimers and ERK signaling in cells with wild-type BRAF," Nature, vol. 464, Mar. 18, 2010, pp. 427-430.
Salmeron, A. et al., "Activation of MEK-1 and SEK-1 by Tpl-2 proto-oncoprotein, a novel MAP kinase kinase kinase," EMBO J, vol. 15, No. 4, 1996, pp. 817-826.
Schwartz, G. K. et al., A phase 1 study of XL281, a selective oral RAF kinase inhibitor, in patients (Pts) with advanced solid tumors, J. Clin. Oncol., vol. 27, No. 15S (suppl.), 2009, p. 3513 (Abstract).
Solit, D. B. et al., "BRAF mutation predicts sensitivity to MEK inhibition," Nature, vol. 439, 2006, pp. 358-362.
Tap, William D. et al., "Pharmacodynamic Characterization of the Efficacy Signals Due to Selective BRAF Inhibition with PLX4032 in Malignant Melanoma," Neoplasia, vol. 12, No. 8, Aug. 2010, pp. 637-649.
Tsai, J. et al., "Discovery of a selective inhibitor of oncogenic B-Raf kinase with potent antimelanoma activity," Proc. Natl Acad. Sci., vol. 105, No. 8, 2008, pp. 3041-3046.
Wan, P. T. et al., "Mechanism of Activation of the RAF-ERK Signaling Pathway by Oncogenic Mutations of B-RAF," Cell, vol. 116, 2004, pp. 855-867.
Wellbrock, C. et al., "$^{V559E}$B-RAF is an Oncogene Melanocytes," Cancer Research, vol. 64, 2004, pp. 2338-2342.
Yang et al.; "AZD6244 (ARRY-142886) enhances the therapeutic efficacy of sorafenib in mouse models of gastric cancer"; Mol Cancer Ther 8(9); pp. 2537-2545; Sep. 1, 2009.
International Search Report for International Application No. PCT/US2011/027689, dated May 27, 2011, 4 pages.
International Preliminary Report on Patentability for International Application No. PCT/US2011/027689, dated Sep. 11, 2012, 8 pages.
Bittinger, et al.; "Abstract #1987: In vitro and in vivo validation of MAP3K8/COT as a promising cancer target"; Cancer Research, vol. 69, No. 9; May 2009; 4 pages.
GenBank Accession No. AY309013; "*Homo sapiens* mitogen-activated protein kinase kinase kinase 8 (MAP3K8) gene, complete cds"; Aug. 19, 2003; 17 pages.

\* cited by examiner

Secondary Screen

| A375 | | | | SKMEL28 | | | |
|---|---|---|---|---|---|---|---|
| Gene | GI50 (µM) | Fold Change | Rank | Gene | GI50 (µM) | Fold Change | Rank |
| - | 0.1528 | 0.91 | (-) | - | 0.4751 | 0.4791 | (-) |
| MEK1 | 0.1671 | 1 | (+) | MEK1 | 1.0 | 1 | (+) |
| MEK DD | 4.8 | 28 | 1 | MEK DD | 8.29 | 8.29 | 1 |
| MAP3K8 | >100.0 | >600 | 2 | MAP3K8 | >100.0 | >100 | 2 |
| RAF1 | >100.0 | >600 | 3 | RAF1 | >100.0 | >100 | 3 |
| CRKL | >10.0 | >60 | 4 | CRKL | 9.70 | 9.7 | 4 |
| FGR | >10.0 | >60 | 5 | FGR | 5.0 | 5 | 5 |
| PRKCE | 4.41 | 26 | 6 | PRKCH | 2.26 | 2.26 | 6 |
| PRKCH | 4.14 | 25 | 7 | PRKCE | 1.91 | 1.91 | 7 |
| ERBB2 | 1.33 | 8 | 8 | AXL | 1.18 | 1.18 | 8 |
| AXL | 1.00 | 6 | 9 | ERBB2 | 1.00 | 1.00 | 9 |
| PAK3 | 0.4934 | 3 |  | PAK3 | 0.9041 | 0.9041 |  |

FIG. 1D

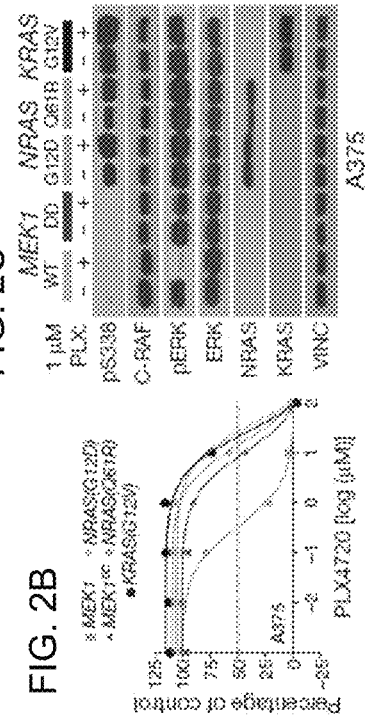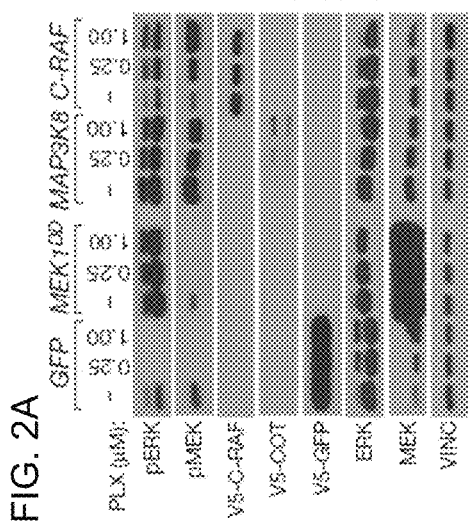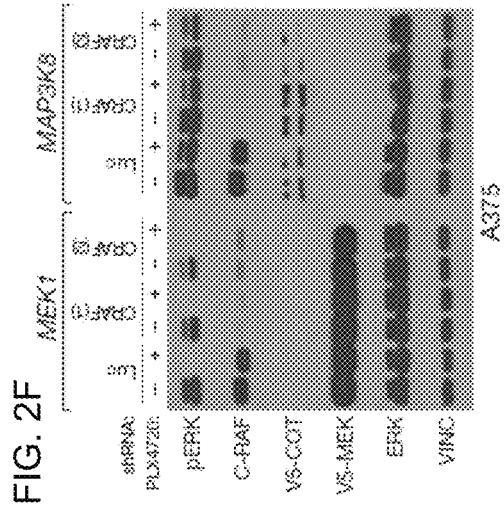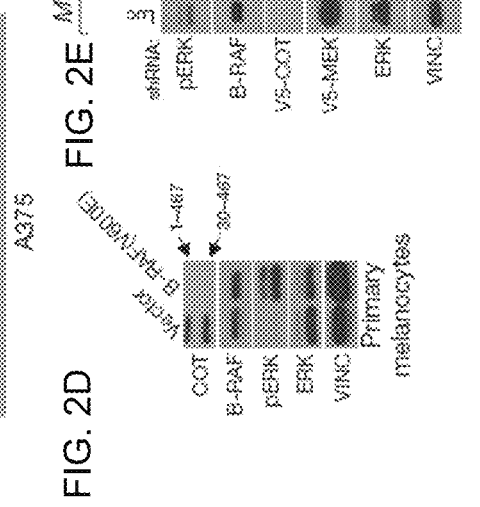

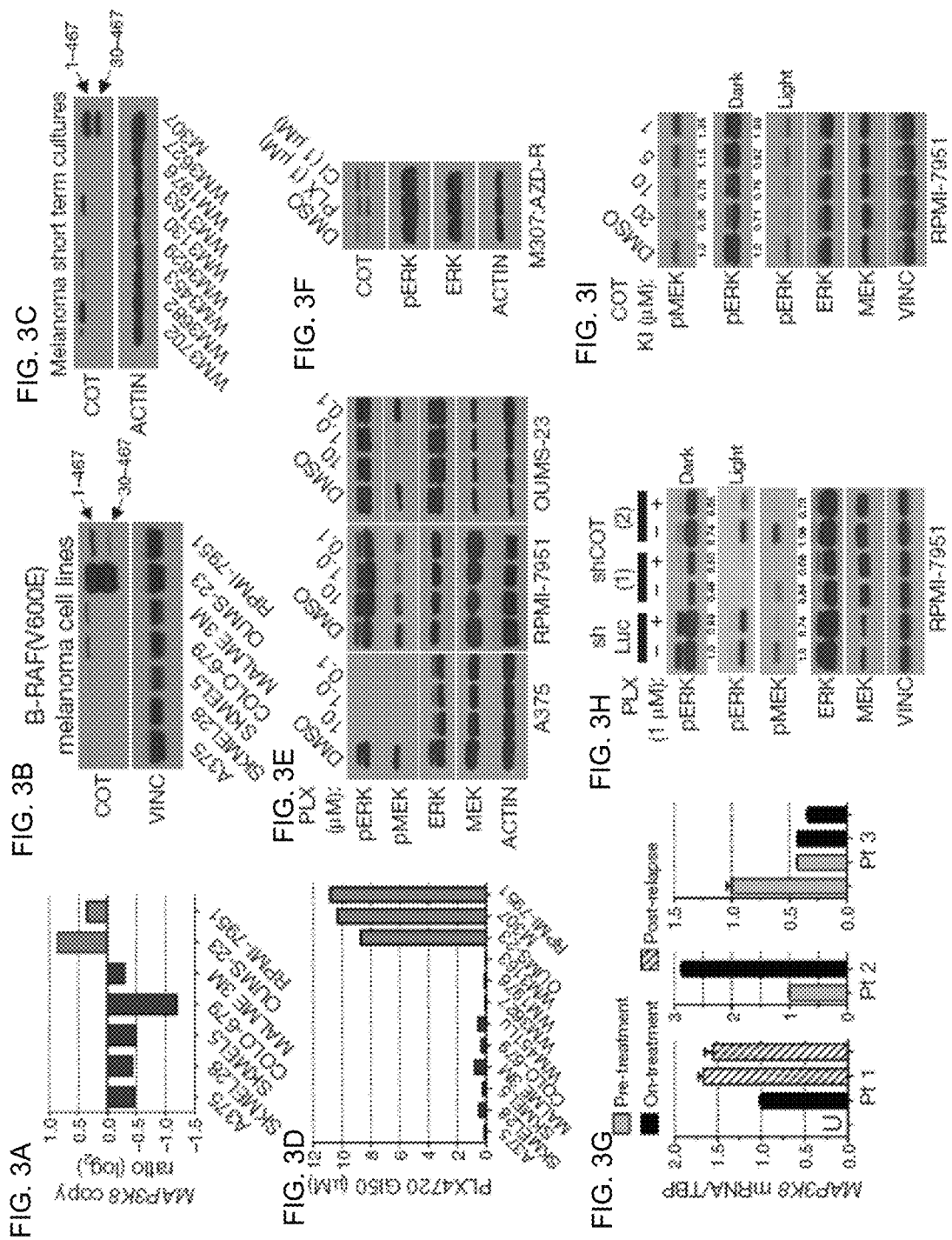

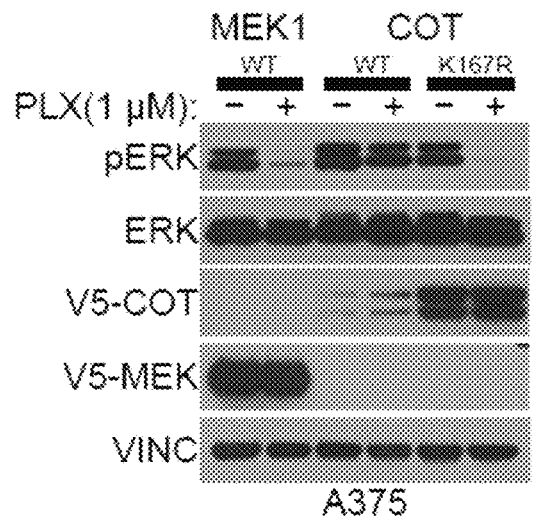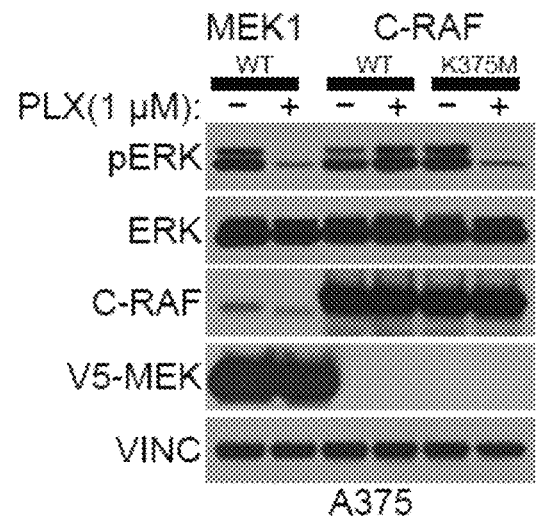
FIG. 11A
FIG. 11B
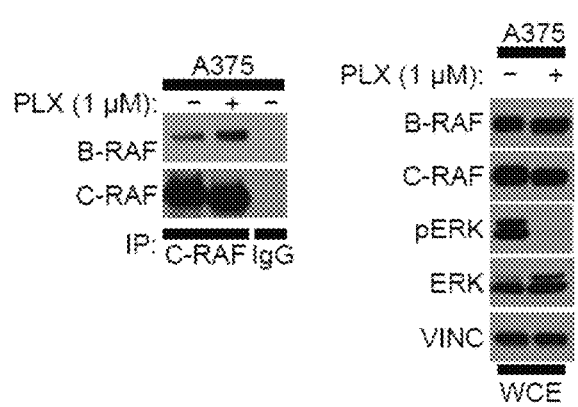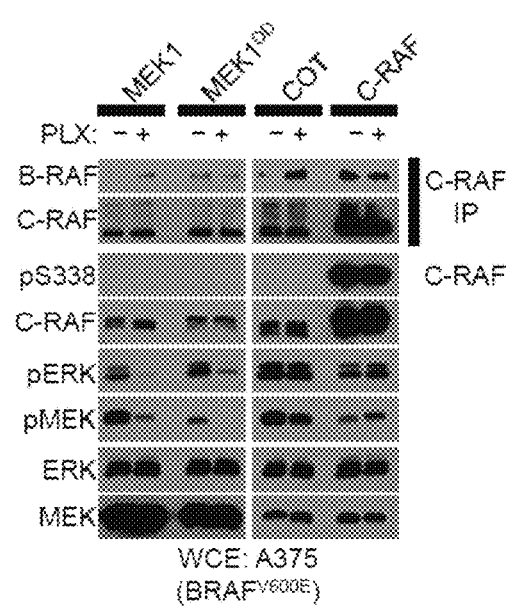
FIG. 13A
FIG. 13B

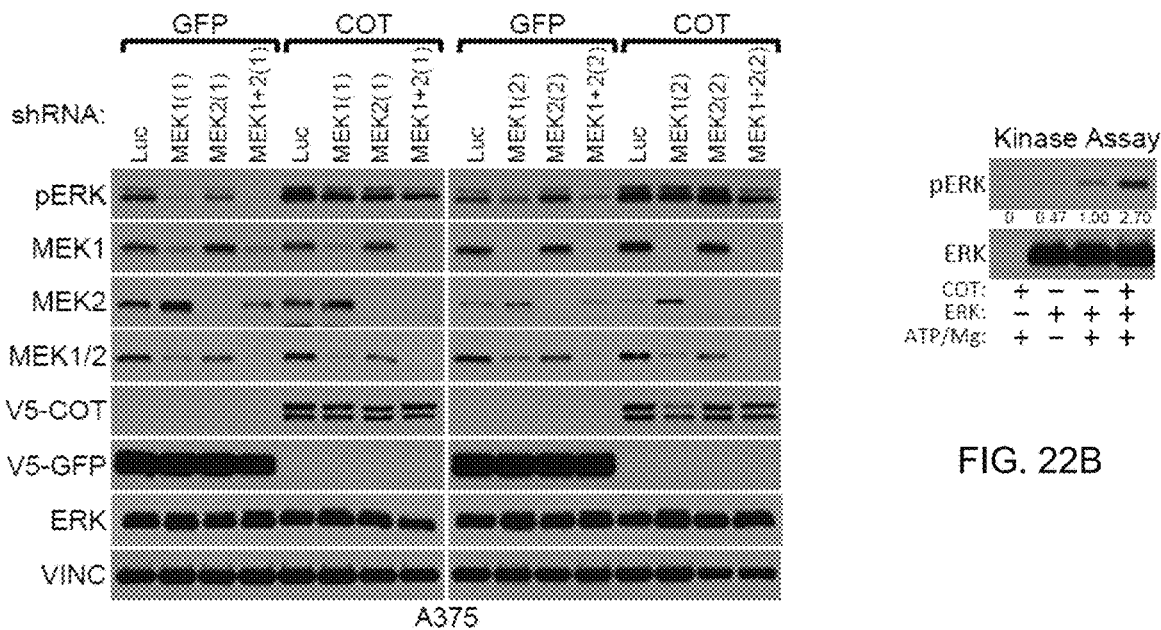
FIG. 22A
FIG. 22B
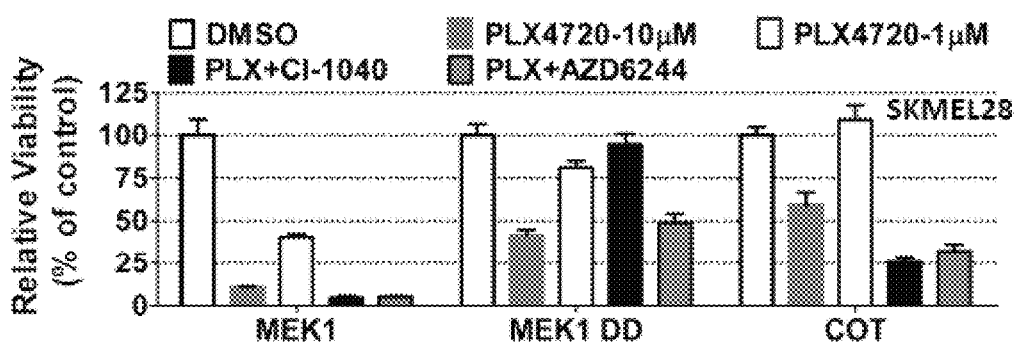
FIG. 23

| Cell line name | BRAF mutational status | PLX4720 sensitivity | Fold sensitivity (rel. to A375) |
|---|---|---|---|
| UACC-62 | V600E | 0.17563626 | 0.836 |
| A-375 | V600E | 0.20279495 | 1.000 |
| SK-MEL-5 | V600E | 0.21298543 | 1.050 |
| MEL-HO | V600E | 0.25853974 | 1.2759 |
| Malme-3M | V600E | 0.2763343 | 1.393 |
| K029AX | V600E, V600D | 0.34965807 | 1.724 |
| IGR-37 | V600E | 0.4014446 | 1.930 |
| COLO-679 | V600E | 0.4499202 | 2.219 |
| UACC-257 | V600E | 0.6370857 | 3.142 |
| A2058 | V600E | 0.69852145 | 3.445 |
| G-361 | V600E | 0.92426234 | 4.658 |
| VYM-115 | V600E | 1.0702046 | 5.277 |
| WM-266-4 | V600E | 1.2778535 | 6.301 |
| LOX IMVI | V600E | 1.3171776 | 6.435 |
| C32 | V600E | 1.6075206 | 7.927 |
| Hs 294T | V600E | 2.3284001 | 11.482 |
| IGR-39 | V600E | 2.5938814 | 12.791 |
| Hs 695T | V600E | 2.851969 | 14.063 |
| SK-MEL-24 | V600E | 8 | 39.449 |
| RFMI-7951 | V600E | 8 | 39.449 |

FIG. 28A

| Cell line name | BRAF mutational status | AZD6244 sensitivity | Fold sensitivity (rel. to A375) |
|---|---|---|---|
| UACC-62 | V600E | 0.0243956 | 0.120 |
| Malme-3M | V600E | 0.0524783 | 0.259 |
| COLO-679 | V600E | 0.0718501 | 0.354 |
| SK-MEL-5 | V600E | 0.0748871 | 0.369 |
| MEL-HO | V600E | 0.0807846 | 0.398 |
| A375 | V600E, V600D | 0.0814318 | 0.402 |
| WM-268-4 | V600E | 0.1294149 | 0.638 |
| UACC-57 | V600E | 0.146748 | 0.724 |
| K029AX | V600E | 0.1516892 | 0.748 |
| IGR-37 | V600E | 0.1655719 | 0.816 |
| WM-115 | V600E | 0.1673957 | 0.825 |
| LOX IMVI7 | V600E | 0.1721772 | 0.849 |
| G-361 | V600E | 0.3210547 | 1.583 |
| Hs 294T | V600E | 0.3424192 | 1.688 |
| A2058 | V600E | 0.3465513 | 1.709 |
| Hs 695T | V600E | 0.5186367 | 2.557 |
| SK-MEL-24 | V600E | 0.6827971 | 3.367 |
| RFMI-7951 | V600E | 0.8942384 | 4.410 |
| G32 | V600E | 0.9828201 | 4.846 |
| IGR-39 | V600E | 2.6921816 | 13.275 |

FIG. 28B

SEQUENCE LISTING

<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: synthetic forward COT primer

<400> SEQUENCE: 1
caagtgaaga gccagcagtt t                                          21

<210> SEQ ID NO 2
<211> LENGTH: 22
<212> TYPE: DNA
<213> ORGANISM: Artificial Sequence
<220> FEATURE:
<223> OTHER INFORMATION: synthetic reverse COT primer

<400> SEQUENCE: 2
gcaagcaaat cctccacagt tc                                         22

<210> SEQ ID NO 3
<211> LENGTH: 22
<212> TYPE: DNA
<213> ORGANISM: Artificial Sequence
<220> FEATURE:
<223> OTHER INFORMATION: synthetic forward TBP primer

<400> SEQUENCE: 3
cccgaaacgc cgaatataat cc                                         22

<210> SEQ ID NO 4
<211> LENGTH: 22
<212> TYPE: DNA
<213> ORGANISM: Artificial Sequence
<220> FEATURE:
<223> OTHER INFORMATION: synthetic reverse TBP primer

<400> SEQUENCE: 4
gactgttctt cactcttggc tc                                         22

```
<210> SEQ ID NO 5
<211> LENGTH: 19
<212> TYPE: DNA
<213> ORGANISM: Artificial Sequence
<220> FEATURE:
<223> OTHER INFORMATION: synthetic forward GAPDH primer

<400> SEQUENCE: 5
catcatctct gccccctct                                                     19

<210> SEQ ID NO 6
<211> LENGTH: 20
<212> TYPE: DNA
<213> ORGANISM: Artificial Sequence
<220> FEATURE:
<223> OTHER INFORMATION: synthetic reverse GAPDH primer

<400> SEQUENCE: 6
ggtgctaagc agttggtggt                                                    20

<210> SEQ ID NO 7
<211> LENGTH: 21
<212> TYPE: DNA
<213> ORGANISM: Artificial Sequence
<220> FEATURE:
<223> OTHER INFORMATION: synthetic DNA construct for shLuc shRNA

<400> SEQUENCE: 7
cttcgaaatg tccgttcggt t                                                  21

<210> SEQ ID NO 8
<211> LENGTH: 21
<212> TYPE: DNA
<213> ORGANISM: Artificial Sequence
<220> FEATURE:
<223> OTHER INFORMATION: synthetic DNA construct for shBRAF(1) shRNA

<400> SEQUENCE: 8
cttcgaaatg tccgttcggt t                                                  21

<210> SEQ ID NO 9
<211> LENGTH: 21
<212> TYPE: DNA
<213> ORGANISM: Artificial Sequence
<220> FEATURE:
<223> OTHER INFORMATION: synthetic DNA construct for shBRAF(2) shRNA

<400> SEQUENCE: 9
gctggtttcc aaacagagga t                                                  21

<210> SEQ ID NO 10
<211> LENGTH: 21
<212> TYPE: DNA
<213> ORGANISM: Artificial Sequence
<220> FEATURE:
<223> OTHER INFORMATION: synthetic DNA construct for shCRAF(1) shRNA

<400> SEQUENCE: 10
cggagatgtt gcagtaaaga t                                                  21

<210> SEQ ID NO 11
<211> LENGTH: 21
<212> TYPE: DNA
<213> ORGANISM: Artificial Sequence
<220> FEATURE:
<223> OTHER INFORMATION: synthetic DNA construct for shCRAF(2) shRNA
```

```
<400> SEQUENCE: 11
gagacatgaa atccaacaat a                                               21

<210> SEQ ID NO 12
<211> LENGTH: 21
<212> TYPE: DNA
<213> ORGANISM: Artificial Sequence
<220> FEATURE:
<223> OTHER INFORMATION: synthetic DNA construct for shMEK1(1) shRNA

<400> SEQUENCE: 12
gattacatag tcaacgagcc t                                               21

<210> SEQ ID NO 13
<211> LENGTH: 21
<212> TYPE: DNA
<213> ORGANISM: Artificial Sequence
<220> FEATURE:
<223> OTHER INFORMATION: synthetic DNA construct for shMEK1(2) shRNA

<400> SEQUENCE: 13
gcttctatgg tgcgttctac a                                               21

<210> SEQ ID NO 14
<211> LENGTH: 21
<212> TYPE: DNA
<213> ORGANISM: Artificial Sequence
<220> FEATURE:
<223> OTHER INFORMATION: synthetic DNA construct for shMEK2(1) shRNA

<400> SEQUENCE: 14
tggactatat tgtgaacgag c                                               21

<210> SEQ ID NO 15
<211> LENGTH: 21
<212> TYPE: DNA
<213> ORGANISM: Artificial Sequence
<220> FEATURE:
<223> OTHER INFORMATION: synthetic DNA construct for shMEK2(2) shRNA

<400> SEQUENCE: 15
ccaacatcct cgtgaactct a                                               21

<210> SEQ ID NO 16
<211> LENGTH: 21
<212> TYPE: DNA
<213> ORGANISM: Artificial Sequence
<220> FEATURE:
<223> OTHER INFORMATION: synthetic DNA construct for shCOT(1) shRNA

<400> SEQUENCE: 16
caagagccgc agacctacta a                                               21

<210> SEQ ID NO 17
<211> LENGTH: 21
<212> TYPE: DNA
<213> ORGANISM: Artificial Sequence
<220> FEATURE:
<223> OTHER INFORMATION: synthetic DNA construct for shCOT(2) shRNA

<400> SEQUENCE: 17
gatgagaatg tgacctttaa g                                               21
```

METHODS OF DIAGNOSING AND TREATING CANCER IN PATIENTS HAVING OR DEVELOPING RESISTANCE TO A FIRST CANCER THERAPY

RELATED APPLICATIONS

This application is a division of U.S. application Ser. No. 13/583,056, filed Sep. 6, 2012, which claims the benefit under 35 U.S.C. § 371 of International Application No. PCT/US2011/027689, filed Mar. 9, 2011, which claims the benefit of the filing date under 35 U.S.C. § 119(e) of the following Provisional U.S. Patent Application Ser. No. 61/312,193, filed Mar. 9, 2010; 61/312,519, filed Mar. 10, 2010; 61/326,021, filed Apr. 20, 2010; and 61/415,569, filed Nov. 19, 2010, all of which are hereby incorporated by reference in their entirety.

FEDERALLY SPONSORED RESEARCH OR DEVELOPMENT

This invention was made with government support under federal grant numbers K08 CA115927 and 1DP2OD002750 awarded by National Institutes of Health. The government has certain rights in the invention.

BACKGROUND

Oncogenic mutations in the serine/threonine kinase B-RAF (also known as BRAF) are found in 50-70% of malignant melanomas. (Davies, H. et al., *Nature* 417, 949-954 (2002).) Pre-clinical studies have demonstrated that the B-RAF(V600E) mutation predicts a dependency on the mitogen-activated protein kinase (MAPK) signalling cascade in melanoma (Hoeflich, K. P. et al., *Cancer Res.* 69, 3042-3051 (2009); McDermott, U. et al., *Proc. Natl Acad. Sci. USA* 104, 19936-19941 (2007); Solit, D. B. et al. BRAF mutation predicts sensitivity to MEK inhibition. *Nature* 439, 358-362 (2006); Wan, P. T. et al., *Cell* 116, 855-867 (2004); Wellbrock, C. et al., *Cancer Res.* 64, 2338-2342 (2004))—an observation that has been validated by the success of RAF or MEK inhibitors in clinical trials (Flaherty, K. T. et al., *N. Engl. J. Med.* 363, 809-819 (2010); Infante, J. R. et al., *J. Clin. Oncol.* 28 (suppl.), 2503 (2010); Schwartz, G. K. et al., *J. Clin. Oncol.* 27 (suppl.), 3513 (2009).) However, clinical responses to targeted anticancer therapeutics are frequently confounded by de novo or acquired resistance. (Engelman, J. A. et al., *Science* 316, 1039-1043 (2007); Gorre, M. E. et al., *Science* 293, 876-880 (2001); Heinrich, M. C. et al., *J. Clin. Oncol.* 24, 4764-4774 (2006); Daub, H., Specht, K. & Ullrich, A. *Nature Rev. Drug Discov.* 3, 1001-1010 (2004).) Accordingly, there remains a need for new methods for identification of resistance mechanisms in a manner that elucidates "druggable" targets for effective long-term treatment strategies, for new methods of identifying patients that are likely to benefit from the treatment strategies, and for methods of treating patients with the effective long-term treatment strategies.

BRIEF SUMMARY

The present invention relates to the development of resistance to therapeutic agents in the treatment of cancer and identification of targets that confer resistance to treatment of cancer. The present invention also relates to identification of parallel drug targets for facilitating an effective long-term treatment strategy and to identifying patients that would benefit from such treatment.

Accordingly, in one aspect, a method of identifying a subject having cancer who is likely to benefit from treatment with a combination therapy with a RAF inhibitor and a second inhibitor is provided. The method includes assaying a gene copy number, a mRNA or a protein level or phosphorylation of one or more kinase targets selected from the group consisting of MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3) in cancer cells obtained from the subject. The method further includes comparing the gene copy number, the mRNA or the protein level or the phosphorylation with a gene copy number, a mRNA or a protein level or phosphorylation of the target kinase in cells obtained from a subject without the cancer and correlating increased gene copy number or an alteration in mRNA expression or protein overexpression or phosphorylation of the target kinase in the cancer cells relative to the cells from the subject without the cancer with the subject having the cancer who is likely to benefit from treatment with the combination therapy.

In another aspect, a method of treating cancer in a subject in need thereof is provided. The method includes administering to the subject an effective amount of a RAF inhibitor and an effective amount of a second inhibitor, wherein the second inhibitor is a MEK inhibitor or a TPL2/COT inhibitor.

In another aspect, a method of identifying a kinase target that confers resistance to a first inhibitor is provided. The method includes culturing cells having sensitivity to the first inhibitor and expressing a plurality of kinase ORF clones in the cell cultures, each cell culture expressing a different kinase ORF clone. The method further includes exposing each cell culture to the inhibitor and identifying cell cultures having greater viability than a control cell culture after exposure to the inhibitor to identify the kinase ORF clone that confers resistance to the first inhibitor.

BRIEF DESCRIPTION OF THE DRAWINGS

FIGS. 1A-1D illustrate an ORF-based functional screen which identified COT and C-RAF kinases as drivers of resistance to B-RAF inhibition. (a) Schematic overview of the CCSB/Broad Institute Kinase ORF collection. Kinase classification and number of kinases per classification are noted; (b) A375 cells expressing the CCSB/Broad Institute Kinase ORF collection were assayed for relative viability in 1 μM PLX4720 and normalized to constitutively active MEK1 (MEK1DD). Nine ORFs (circles) scored 2 standard deviations (dashed line, 58.64%) from the mean of all ORFs (dashed line, 44.26%); (c) Indicated ORFs were expressed in 5 B-RAF$^{V600E}$ cell lines and treated with DMSO or 1 μM PLX4720. Viability (relative to DMSO) was quantified after 4 days. Error bars represent standard deviation between replicates (n=6); (d) Secondary screen in A375 and SKMEL28 prioritizes the top 9 candidate ORFs across a multipoint PLX4720 concentration scale.

FIGS. 2A-2F illustrate resistance to B-RAF inhibition via MAPK pathway activation. (a) Indicated ORFs were expressed in A375. Levels of phosphorylated MEK and ERK were assayed following 18 h. treatment with DMSO (−) or PLX4720 (concentration noted); (b) Proliferation of A375 expressing indicated ORFs. Error bars represent standard deviation between replicates (n=6). (c) C-RAF (S338) and ERK phosphorylation in lysates from A375 expressing indicated ORFs. (d) COT expression in lysates from immortalized primary melanocytes expressing BRAFV600E or empty vector. COT mRNA has an internal start codon (30M) resulting in two protein products of different lengths; amino acids 1-467 or 30-467, noted with arrows. (e) COT and ERK phosphorylation in lysates from A375 expressing indicated ORFs following shRNA-mediated B-RAF depletion (shBRAF) relative to control shRNA (shLuc). (f) ERK phosphorylation in lysates from A375 expressing indicated ORFs following shRNA-mediated C-RAF depletion (sh-CRAF) or control shRNA (shLuc), following 18 h. treatment with DMSO (−) or 1 µM PLX4720 (+).

FIGS. 3A-3K illustrate COT expression predicts resistance to B-RAF inhibition in cancer cell lines. (a) MAP3K8/COT copy number; red bars: COT amplification, blue bars: non-amplified COT; (b) COT expression in B-RAF$^{V600E}$ cell lines and (c) short-term cultures; (d) PLX4720 GI50 in B-RAF$^{V600E}$ cell lines. Colors as in (a); (e) MEK and ERK phosphorylation following treatment with DMSO or PLX4720 (concentration indicated); (f) ERK phosphorylation in M307 lysates (AZD-R; AZD6244-resistant) treated with DMSO or 1 µM PLX4720 (PLX) or CI-1040 (CI); (g) COT mRNA expression (QRT/PCR) in patient/lesion-matched PLX4032-treated metastatic melanoma tissue samples. Pts. 1 and 3 had multiple biopsies from the same lesion. Error bars represent SEM (n=3) U; undetermined/undetectable; (h) ERK and MEK phosphorylation in RPMI-7951 following shRNA-mediated COT depletion (shCOT) versus control (shLuc) and treatment with DMSO (−) or 1 µM PLX4720 (+). ERK and MEK phosphorylation are quantified; (i) ERK and MEK phosphorylation in RPMI-7951 following 1 h. treatment with a small molecule COT kinase inhibitor. ERK and MEK phosphorylation are quantified. (j) PLX4720 sensitivity curves in a panel of BRAF$^{V600E}$ cell lines. OUMS-23 and M307 represent cell lines with COT expression/amplification and all others represent cell lines with undetectable/unaltered COT; (k) Selective expression of COT and corresponding MAPK pathway activation in a metastatic subcutaneous malignant melanoma with acquired resistance to PLX4032 (* denotes a background band, MET-MM (PLX-R); metastatic malignant melanoma, PLX4032-resistant).

FIGS. 11A-11B illustrate that the kinase activity of COT and C-RAF is required for sustained ERK phosphorylation in the context of PLX4720 treatment. Immunoblot analysis of A375 expressing ectopic (a) MEK1, wild type COT or kinase inactive COT (COT$^{K167R}$) or (b) MEK1, wild type C-RAF or kinase inactive C-RAF (C-RAF$^{K375M}$) treated with 1 µM PLX4720 for 18 h.

FIGS. 13A-13B illustrate that B-RAF associates with immunoprecipitated C-RAF in A375 following 18 hr. treatment with 1 μM PLX4720 (+) or DMSO (−), (a). WCE; whole cell extract controls. Ectopically expressed C-RAF constitutively associates with B-RAF and is phosphorylated at S338, consistent with membrane localization and activation. MEK1, MEK$^{DD}$ and COT-expressing A375 show no evidence of C-RAF activation, (b).

FIGS. 18A-18C illustrate MAP3K8/COT alterations in the cancer cell line OUMS-23. (a) RMA signal of a MAP3K8/COT probe (noted) from mRNA microarray analysis. OUMS-23 is one of the top 2% (of 765 cell lines) expressing COT mRNA. (b) COT mRNA expression in a panel of B-RAF$^{V600E}$-mutant cell lines. (c) Endogenous COT protein expression in OUMS-23 relative to ectopically expressed COT in A375 and SKMEL28 cell lines, as determined via immunoblot analysis of the indicated cells.

FIGS. 22A-22B illustrate that COT can activate ERK via MEK-independent and MEK-dependent mechanisms. (a) Immunoblot analysis of ERK phosphorylation in lysates from A375 following expression of GFP or COT and subsequent lentiviral shRNA-mediated MEK1, MEK2 or MEK1 and MEK2 (MEK1+2) depletion, relative to control shRNA (shLuc). Left and right panels represent two different pairs of MEK1 and MEK2 shRNA constructs. (b) Immunoblot analysis of recombinant, inactive ERK phosphorylation (Thr202/Tyr204) by recombinant COT in an in vitro kinase assay.

FIG. 23 illustrates that combinatorial MAPK pathway inhibition effectively suppresses proliferation in SKMEL28. Viability (relative to DMSO) of SKMEL28 ectopically expressing MEK1, MEK1$^{DD}$ or COT and treated with DMSO, PLX4720 (concentration indicated), PLX4720 (1 μM) and CI-1040 (1 μM) or PLX4720 (1 μM) and AZD6244 (1 μM). Error bars represent the standard deviation between replicates.

FIGS. 28A-28B illustrate the insensitivity to MAPK pathway inhibition corresponds with MAP3K8/COT copy number gains in a subset of skin cancer cell lines. A panel of 20 B-RAF$^{V600E}$-mutant cell lines and their sensitivity to (a) the B-RAF inhibitor PLX4720 and (b) the MEK inhibitor AZD6244 is shown.

DETAILED DESCRIPTION OF THE INVENTION

Figure 1A:
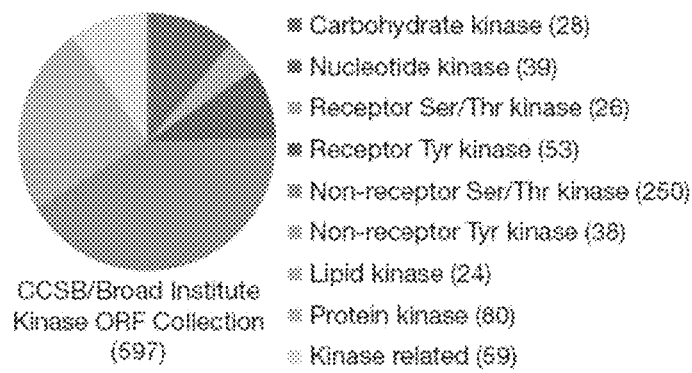

The present invention relates to the development of resistance to therapeutic agents in the treatment of cancer and identification of targets that confer resistance to treatment of cancer. The present invention also relates to identification of parallel drug targets for facilitating an effective long-term treatment strategy and to identifying patients that would benefit from such treatment. In some embodiments, the present invention relates to kinases and in particular to MAP kinase pathway components.

The practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

The mitogen-activated protein kinase (MAPK) cascade is a critical intracellular signaling pathway that regulates signal transduction in response to diverse extracellular stimuli, including growth factors, cytokines, and proto-oncogenes. Activation of this pathway results in transcription factor activation and alterations in gene expression, which ultimately lead to changes in cellular functions including cell proliferation, cell cycle regulation, cell survival, angiogenesis and cell migration. Classical MAPK signaling is initiated by receptor tyrosine kinases at the cell surface, however many other cell surface molecules are capable of activating the MAPK cascade, including integrins, heterotrimeric G-proteins, and cytokine receptors.

Ligand binding to a cell surface receptor, e.g., a receptor tyrosine kinase, typically results in phosphorylation of the receptor. The adaptor protein Grb2 associates with the phosphorylated intracellular domain of the activated receptor, and this association recruits guanine nucleotide exchange factors including SOS-I and CDC25 to the cell membrane. These guanine nucleotide exchange factors interact with and activate the GTPase Ras. Common Ras isoforms include K-Ras, N-Ras, H-Ras and others. Following Ras activation, the serine/threonine kinase Raf (e.g., A-Raf, B-Raf or Raf-1) is recruited to the cell membrane through interaction with Ras. Raf is then phosphorylated. Raf directly activates MEKI and MEK2 by phosphorylation of two serine residues at positions 217 and 221. Following activation, MEKI and MEK2 phosphorylate tyrosine (Tyr-185) and threonine (Thr-183) residues in serine/threonine kinases ErkI and Erk2, resulting in Erk activation. Activated Erk regulates many targets in the cytosol and also translocates to the nucleus, where it phosphorylates a number of transcription factors regulating gene expression. Erk kinase has numerous targets, including Elk-I, c-EtsI, c-Ets2, p90RSKI, MNKI, MNK2, MSKI, MSK2 and TOB. While the foregoing pathway is a classical representation of MAPK signaling, there is considerable cross talk between the MAPK pathway and other signaling cascades.

Aberrations in MAPK signaling have a significant role in cancer biology. Altered expression of Ras is common in many cancers, and activating mutations in Ras have also been identified. Such mutations are found in up to 30% of all cancers, and are especially common in pancreatic (90%) and colon (50%) carcinomas. In addition, activating Raf mutations have been identified in melanoma and ovarian cancer. The most common mutation, $BRAF^{V600E}$, results in constitutive activation of the downstream MAP kinase pathway and is required for melanoma cell proliferation, soft agar growth, and tumor xenograft formation. Based on the defined role of MAPK over-activation in human cancers, targeting components of the MAPK pathway with specific inhibitors is a promising approach to cancer therapy. However, patients may have innate resistance or acquire resistance to these promising therapies. Identification of target kinases, diagnostic and/or prognostic markers and treatment therapies for these patients with innate or acquired resistance are described below.

High Throughput Functional Screening Assay

In some aspects, the present invention relates to methods of identifying targets capable of driving resistance to clinically efficacious therapies using a high throughput screening assay. In some embodiments, the method may include an open reading frame (ORF)-based functional screen for kinases that drive resistance to therapeutic agents. The method may include providing a cell line with a kinase known to have an oncogenic mutation. A library of kinase ORFs may be individually expressed in the cell line so that a plurality of clones each expressing a different ORF from the library may be further evaluated. Each clone may be (1) exposed to an inhibitor of the known kinase in the cell line and (2) monitored for growth changes based on the expression of the ORF in the cell line without the inhibitor. Any clones having a growth effect from the ORF expression alone, either positive or negative growth, are eliminated. The remaining clones each expressing a different kinase are then compared for viability between a control and a treated clone and normalized to a positive control. Increased cell viability after treatment with the inhibitor identifies ORFs that confer resistance and therefore identifies kinase targets for treatment with an additional inhibitor. In some embodiments, clones scoring above two standard deviations from the normalized mean may be target kinases indicating treatment with an additional inhibitor is beneficial to the subject.

Figure 5:
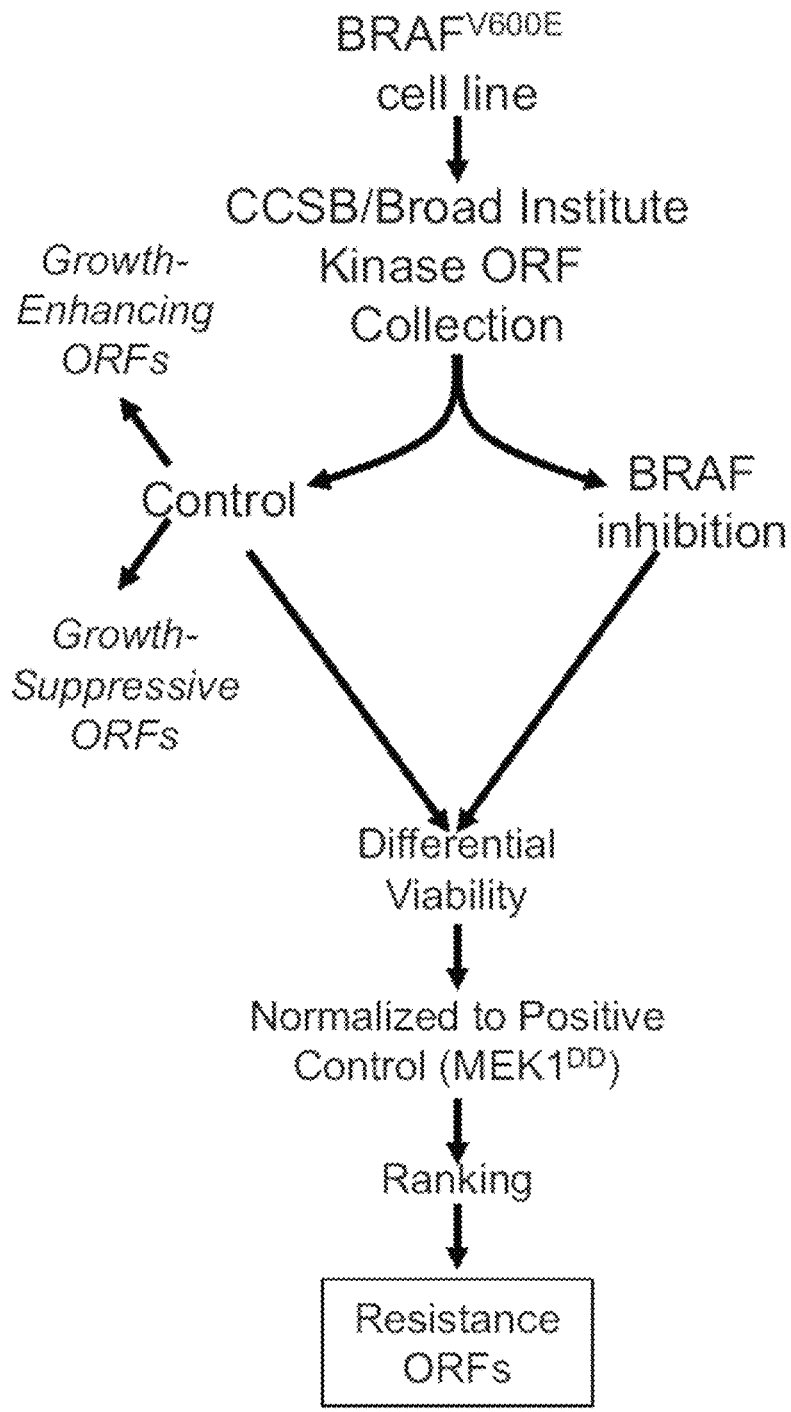
FIG. 5 illustrates a schematic outline of an ORF-based functional screen for kinases that drive resistance to B-RAF inhibition. The B-RAF$^{V600E}$ cell line A375 was lentivirally transduced with the 597 kinases in the CCSB/Broad Institute Kinase ORF Collection. ORFs having a positive or negative effect on proliferation in control-treated A375 were identified and removed from final analysis. Resistance-promoting ORFs were identified by generating a differential viability ratio between B-RAF inhibited (PLX4720-treated) and control-treated cells. Differential viability was normalized to a constitutively active MEK1 allele, MEK1$^{DD}$; an assay specific positive control.

By way of non-limiting example, a schematic of a high throughput functional screening assay for kinases that drive resistance to B-RAF inhibition is shown in FIG. 5. A collection of ~600 cloned and sequence validated ORFs were assembled, accounting for ~75% of all annotated kinases (Center for Cancer Systems Biology (CCSB)/Broad Institute Kinase ORF Collection, FIGS. 1a, 1b, Table 3). This publically available collection can be rapidly transferred into a variety of expression vectors for various end-applications. Any type of expression vector known to one skilled in the art may be used to express the Kinase ORF collection. By way of non-limiting example, a selectable, epitope-tagged, lentiviral expression vector capable of producing high titer virus and robust ORF expression in mammalian cells may be created to express the kinase collection, (pLX-BLAST-V5, FIG. 6a).

Figure 1B:
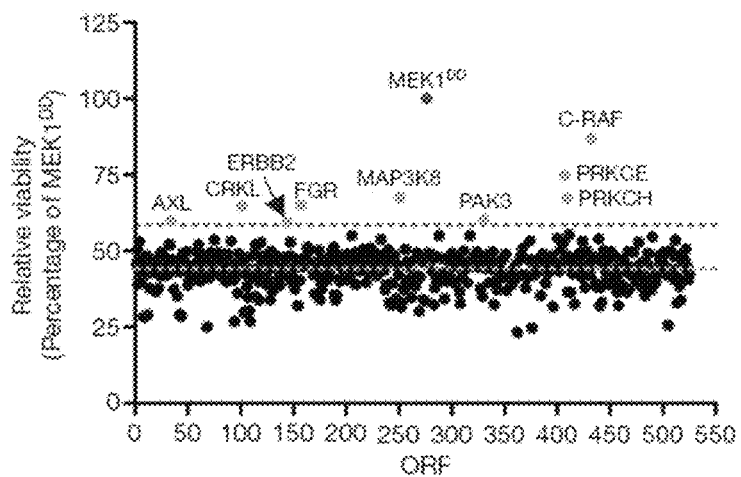
Figure 6C:
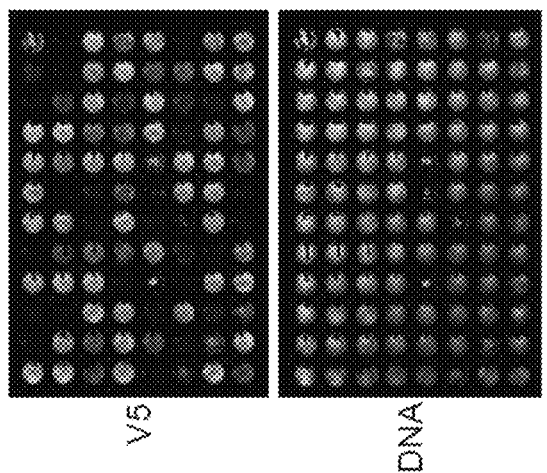
FIGS. 6A-6C illustrate that the CCSB/Broad Institute Kinase ORF Collection is well expressed via high titer lentivirus. (a), schematic of the pLX-BLAST-V5 lentiviral expression vector used for all ORF-screens and subsequent validation. (b) GFP-tagged ORFs representing a broad size range were lentivirally expressed in Jurkat cells and the percentage of GFP-expressing cells/ORF (e.g., infected cells) quantified, demonstrating high viral titer across a range of ORF sizes. (c), expression of 96 random ORFs detected via LiCor with antibodies against the V5-epitope tag, relative to cellular DNA. Expression was detectable in 83% of the wells.
Figure 6B:
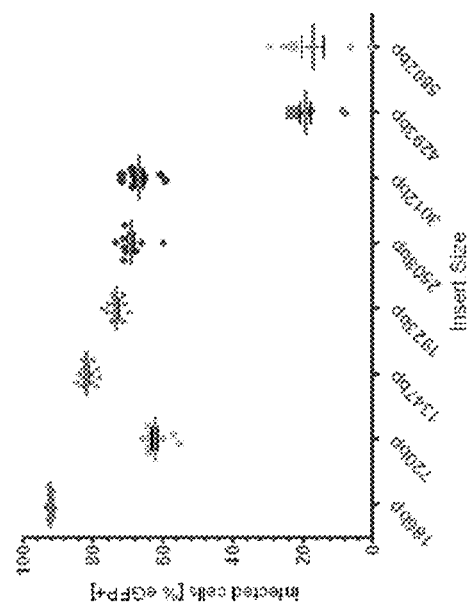
Figure 6A:
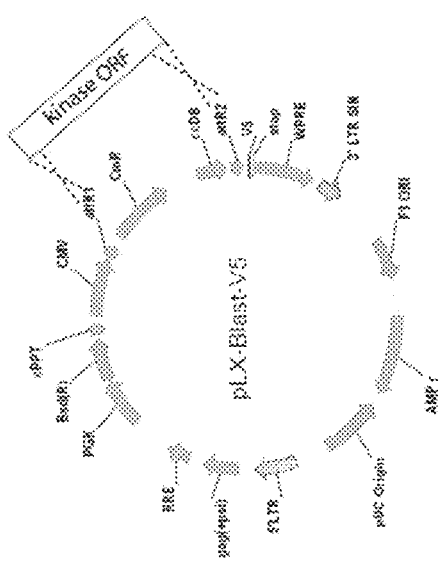

To identify kinases capable of circumventing RAF inhibition, the arrayed kinase ORF collection may be stably expressed in A375, a B-RAF$^{V600E}$ malignant melanoma cell line that is sensitive to the RAF kinase inhibitor PLX4720 (FIGS. 1a, 1b and 6c, Table 3). Clones of ORF expressing cells treated with 1 µM PLX4720 are screened for viability relative to untreated cells and normalized to an assay-specific positive control, MEK1$^{S218/222D}$ (MEK1$^{DD}$) (Table 4). ORFs that affected baseline viability or proliferation are removed from the analysis. Clones scoring above two standard deviations from the normalized mean may be further evaluated to identify a resistance conferring target kinase for a second inhibitor. In some embodiments, the gene encoding the target kinase may be MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3). In some embodiments, the gene encoding the target kinase may be a MAPK pathway activator. In some embodiments, the gene encoding the target kinase may be a MAP3 kinase that directly phosphorylates and activates MEK. In some embodiments, the gene encoding the target kinase may encode an adapter protein that is amplified and phosphorylated in melanoma.

In other embodiments, the ORF collection may be stably expressed in a cell line having a different mutation in B-RAF, for example, another mutation at about amino acid position 600 such as V600K, V600D, and V600R. Additional B-RAF mutations include the mutations described in Davies et al. Nature, 417, 949-954, 2002, Table 1. Cell lines may be used that are sensitive to other RAF kinase inhibitors including, but not limited to, PLX4032; GDC-0879; RAF265; sorafenib; SB590855 and/or ZM 336372. In some embodiments, the ORF collection may be stably expressed in a cell line having a sensitivity to a MEK inhibitor. Non-limiting examples of MEK inhibitors include, AZD6244; CI-1040; PD184352; PD318088, PD98059, PD334581, RDEA119, 6-Methoxy-7-(3-morpholin-4-yl-propoxy)-4-(4-phenoxy-phenylamino)-quinoline-3-carbonitrile and 4-[3-Chloro-4-(1-methyl-1H-imidazol-2-ylsulfanyl)-phenylamino]-6-methoxy-7-(3-morpholin-4-yl-propoxy)-quinoline-3-carbonitrile. Additional RAF and MEK inhibitors are described below. By way of non-limiting example, exemplary RAF inhibitors are shown in Table 1 and exemplary MEK inhibitors are shown in Table 2.

TABLE 1

Exemplary RAF Inhibitors

| Name | CAS No. | Structure |
|---|---|---|
| 1 RAF265 | 927880-90- | 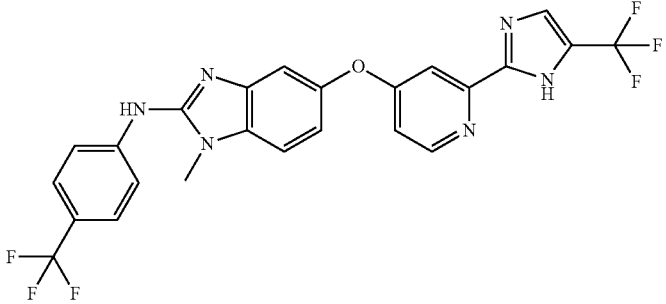 [SMILES: Cn1c(Nc2ccc(C(F)(F)F)cc2)nc2cc(Oc3ccnc(-c4ncc(C(F)(F)F)[nH]4)c3)ccc21] |
| 2 Sorafenib Tosylate Nexavar Bay 43-9006 | 475207-59-1 | 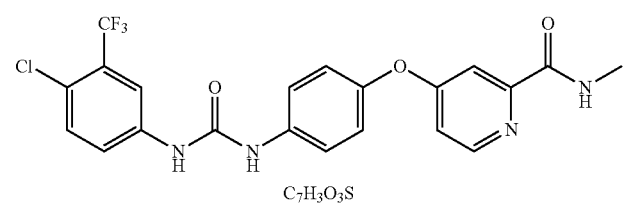 |
| Sorafenib 4-[4-[[4-chloro-3-(trifluoromethyl)phenyl]carbamoyl-amino]phenoxy]-N-methyl-pyridine-2-carboxamide | 284461-73-0 | 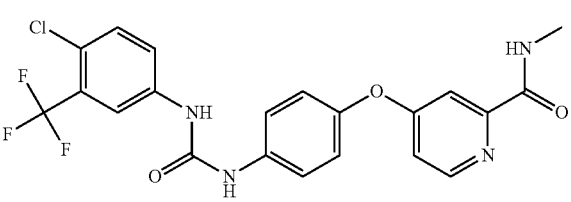 [SMILES: CNC(=O)c1cc(Oc2ccc(NC(=O)Nc3ccc(Cl)c(C(F)(F)F)c3)cc2)ccn1] |
| 3 SB590885 | | 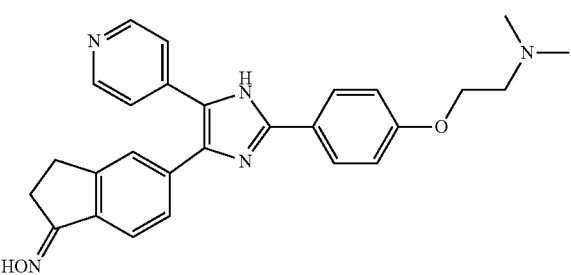 |

TABLE 1-continued

Exemplary RAF Inhibitors

| Name | CAS No. | Structure |
|---|---|---|
| 4 PLX4720 | 918505-84-7 | 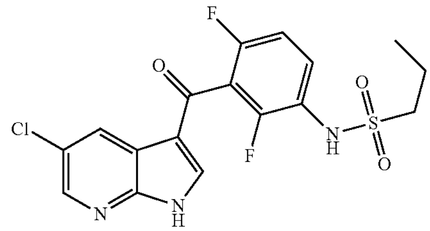 [SMILES: CCCS(=O)(=O)Nc1ccc(F)c(C(=O)c2c[nH]c3ncc(Cl)cc23)c1F] |
| 5 PLX4032 | 1029872-54-5 | 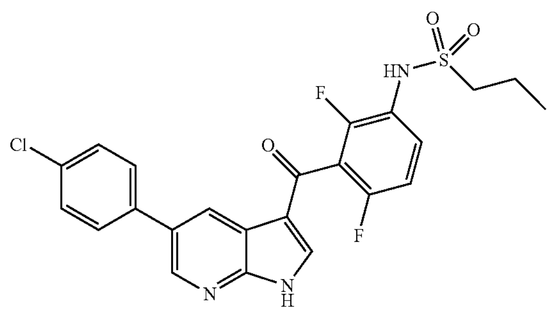 [SMILES: CCCS(=O)(=O)Nc1ccc(F)c(C(=O)c2c[nH]c3ncc(-c4ccc(Cl)cc4)cc23)c1F] |
| 6 GDC-0879 | 905281-76-7 | 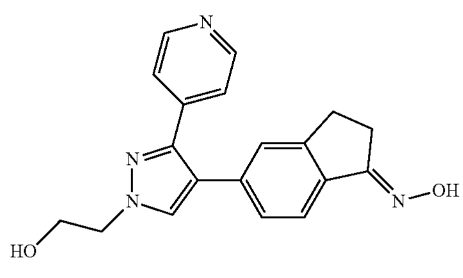 [SMILES: OCCn1cc(-c2ccc3c(c2)CC/C3=N\O)c(-c2ccncc2)n1] |
| 7 ZM 336372 | 208260-29-1 | 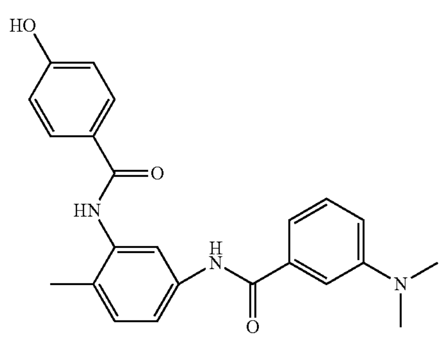 [SMILES: Cc1ccc(NC(=O)c2cccc(N(C)C)c2)cc1NC(=O)c1ccc(O)cc1] |

TABLE 2
| | Exemplary MEK Inhibitors | |
|---|---|---|
| Name | CAS No. | Structure |
| 1 CI-1040/PD184352 | 212631-79-3 | 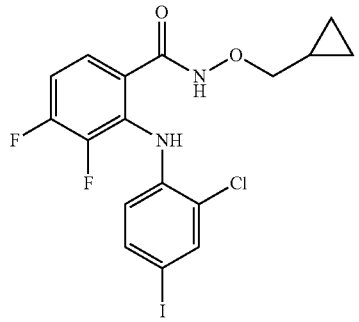 [SMILES: O=C(NOCC1CC1)c1ccc(F)c(F)c1Nc1ccc(I)cc1Cl] |
| 2 AZD6244 | 606143-52-6 | 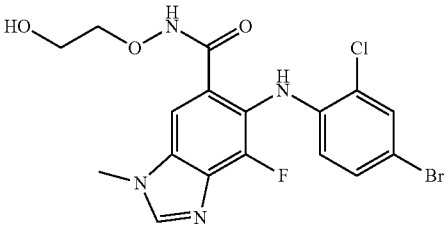 [SMILES: Cn1cnc2c(F)c(Nc3ccc(Br)cc3Cl)c(C(=O)NOCCO)cc21] |
| 3 PD318088 | 391210-00-7 | 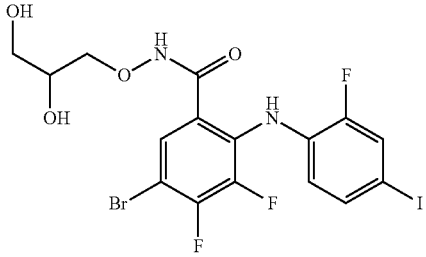 [SMILES: O=C(NOCC(O)CO)c1cc(Br)c(F)c(F)c1Nc1ccc(I)cc1F] |
| 4 PD98059 | 167869-21-8 | 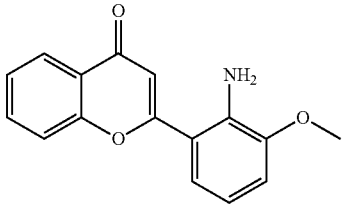 [SMILES: COc1cccc(-c2cc(=O)c3ccccc3o2)c1N] |
| 5 PD334581 | | 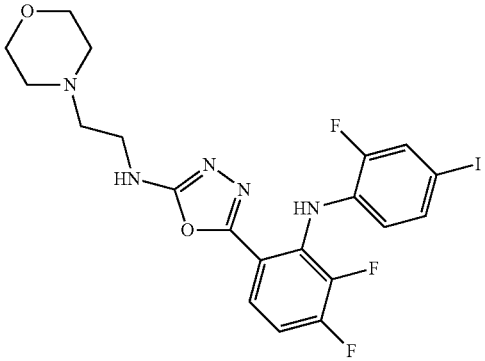 [SMILES: Fc1cc(I)ccc1Nc1c(-c2nnc(NCCN3CCOCC3)o2)ccc(F)c1F] |

TABLE 2-continued

Exemplary MEK Inhibitors

| Name | CAS No. | Structure |
|---|---|---|
| 6 RDEA119<br>N-[3,4-difluoro-2-[(2-fluoro-4-iodophenyl)amino]-6-methoxyphenyl]-1-[(2R)-2,3-dihydroxypropyl]-Cyclopropanesulfonamide | 923032-38-6 | |
| 7 6-Methoxy-7-(3-morpholin-4-yl-propoxy)-4-(4-phenoxy-phenylamino)-quinoline-3-carbonitrile | | 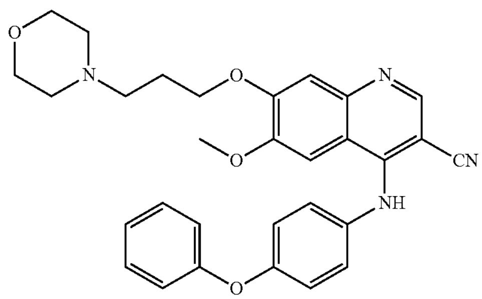 [SMILES: COc1cc2c(Nc3ccc(Oc4ccccc4)cc3)c(C#N)cnc2cc1OCCCN1CCOCC1] |
| 8 4-[3-Chloro-4-(1-methyl-1H-imidazol-2-ylsulfanyl)-phenylamino]-6-methoxy-7-(3-morpholin-4-yl-propoxy)-quinoline-3-carbonitrile | | 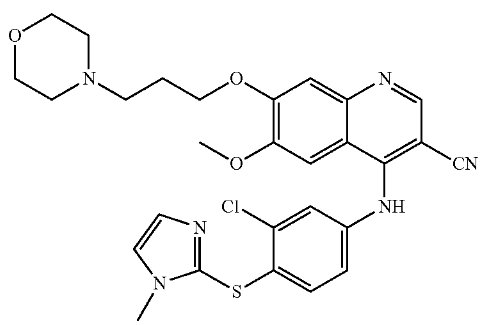 [SMILES: COc1cc2c(Nc3ccc(Sc4nccn4C)c(Cl)c3)c(C#N)cnc2cc1OCCCN1CCOCC1] |

Diagnostic/Prognostic Markers for Innate and Acquired Resistance to Targeted Therapies In some aspects, the present invention relates to methods of detecting the presence of one or more diagnostic or prognostic markers in a sample (e.g. a biological sample from a cancer patient). A variety of screening methods known to one of skill in the art may be used to detect the presence of the marker in the sample including DNA, RNA and protein detection. The techniques described below can be used to determine the presence or absence of a kinase target in a sample obtained from a patient. In some embodiments, the patient may have innate or acquired resistance to kinase targeted therapies, including B-RAF inhibitors or MEK inhibitors. For example, the patient may have an innate or acquired resistance to B-RAF inhibitors PLX4720 and/or PLX4032. In some embodiments, the patient may have innate or acquired resistance to MEK inhibitor AZD6244. Identification of one or more kinase targets markers in a patient assists the physician in determining a treatment protocol for the patient. For example, in a patient having one or more kinase target markers, the physician may treat the patient with a combination therapy as described in more detail below.

In some embodiments, the kinase target may include, but is not limited to, MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3). The marker may be an increase in the gene copy number, an increase in protein expression, phosphorylation of one or more MAP kinase pathway members, a change in mRNA expression and the like, for the kinase target.

By way of non-limiting example, in a patient having an oncogenic mutation in B-RAF, identification of an activated target kinase can be useful for characterizing a treatment protocol for the patient. For example, in a patient having a B-RAF$^{V600E}$ mutation, treatment with a RAF inhibitor alone may indicate that the patient is at relatively high risk of acquiring resistance to the treatment after a period of time. In a patient having an oncogenic mutation, identification of an activated kinase target in that patient may indicate inclusion of a second inhibitor in the treatment protocol.

Identification of an activated kinase target may include analysis of a gene copy number and identification of an increase in copy number of a target kinase. For example, a copy number gain in MAP3K8 is indicative of a patient having innate resistance or developing acquired resistance, in particular if the patient also has a B-RAF$^{V600E}$ mutation.

In some embodiments, identification of an activated kinase target may include an analysis of phosphorylation of a kinase target and/or a member of the MAP kinase pathway. For example, phosphorylation of C-RAF at S338 is indicative of a patient having innate resistance or developing acquired resistance, in particular if the patient also has a B-RAF$^{V600E}$ mutation. In some embodiments, identification of an increase in MEK/ERK phosphorylation may be indicative of a patient having innate resistance or developing acquired resistance. Increased COT protein expression in patients having a B-RAF$^{V600E}$ mutation may predict resistance to RAF inhibition and MEK inhibition.

Identification of an activated kinase target may include an analysis of mRNA expression of a kinase target. For example, an increase in COT mRNA expression following initial treatment with a first kinase inhibitor is indicative of a patient having or developing resistance. In some embodiments, the first kinase inhibitor may be a RAF inhibitor or a MEK inhibitor.

Methods of Treatment

In various embodiments, the invention provides methods for treatment of a patient having cancer. The methods generally comprise administration of a first inhibitor and a second inhibitor. One inhibitor may be a RAF inhibitor. The RAF inhibitor may be a pan-RAF inhibitor or a selective RAF inhibitor. Pan-RAF inhibitors include but are not limited to RAF265, sorafenib, or SB590885. In some embodiments, the RAF inhibitor is a B-RAF inhibitor. In some embodiments, the selective RAF inhibitor is PLX4720, PLX4032, or GDC-0879-A. One inhibitor may be a MEK inhibitor (see Table 2 illustrating exemplary MEK inhibitors). One inhibitor may be a COT inhibitor. By way of non-limiting example, the COT inhibitor may be a shRNA inhibitor as described below or a small molecule COT inhibitor, 4-(3-chloro-4-fluorophenylamino)-6-(pyridin-3-yl-methylamino)-3-cyano-[1,7]-naphthyridine (EMD; TPL2 inhibitor I; catalogue number 616373, PubChem ID: 9549300) Inhibitors of the present invention inhibit one or more of the kinase targets including MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3) or other MAP kinase pathway targets.

In some embodiments, a combination therapy for cancer is provided, comprising an effective amount of a RAF inhibitor and an effective amount of a MAP3K8 (TPL2/COT) inhibitor. Also provided herein is a combination therapy for cancer, comprising an effective amount of a RAF inhibitor and an effective amount of a MEK inhibitor. Other combination therapies include an effective amount of a RAF inhibitor and an effective amount of a second inhibitor targeting the gene, mRNA or protein encoded by one or more of the following: MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3). The combination therapy is suitable for treatment of a patient wherein the cancer contains B-RAF mutant cells and in particular, B-RAF$^{V600E}$ mutant cells. The present invention further provides a combination therapy for cancer, comprising an effective amount of a RAF inhibitor and an effective amount of a MEK inhibitor, wherein the subject with the cancer contains cells with altered MAP3K8 (TPL2/COT) expression or gene copy number. In some embodiments, the MEK inhibitor is CI-1040/PD184352 or AZD6244.

As a non-limiting example, the MEK inhibitor provided herein can be CI-1040, AZD6244, PD318088, PD98059, PD334581, RDEA119, 6-Methoxy-7-(3-morpholin-4-yl-propoxy)-4-(4-phenoxy-phenylamino)-quinoline-3-carbonitrile or 4-[3-Chloro-4-(1-methyl-1H-imidazol-2-ylsulfanyl)-phenylamino]-6-methoxy-7-(3-morpholin-4-yl-propoxy)-quinoline-3-carbonitrile, Roche compound RG7420, or combinations thereof. Additional MEK inhibitors known in the art may also be used.

In exemplary embodiments of the foregoing aspects, the RAF inhibitor provided herein is PLX4720, PLX4032, BAY 43-9006 (Sorafenib), ZM 336372, RAF 265, AAL-881, LBT-613, or CJS352 (NVP-AAL881-NX (hereafter referred to as AAL881) and NVP-LBT613-AG-8 (LBT613) are isoquinoline compounds (Novartis, Cambridge, Mass.). Additional exemplary RAF inhibitors useful for combination therapy include pan-RAF inhibitors, inhibitors of B-RAF, inhibitors of A-RAF, and inhibitors of RAF-1. In exemplary embodiments RAF inhibitors useful for combination therapy include PLX4720, PLX4032, BAY 43-9006 (Sorafenib), ZM 336372, RAF 265, AAL-881, LBT-613, and CJS352. Exemplary RAF inhibitors further include the compounds set forth in PCT Publication No. WO/2008/028141, the entire contents of which are incorporated herein by reference. Exemplary RAF inhibitors additionally include the quinazolinone derivatives described in PCT Publication No. WO/2006/024836, and the pyridinylquinazolinamine derivatives described in PCT Publication No. WO/2008/020203, the entire contents of which are incorporated herein by reference.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination therapy of the invention includes both the free base of the compounds, and all pharmaceutically acceptable salts of the compounds. A preferred salt is the hydrochloride salt.

The term "pharmaceutically acceptable salts" includes derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, and nitric; other acceptable inorganic salts include metal salts such as sodium salt, potassium salt, and cesium salt; and alkaline earth metal salts, such as calcium salt and magnesium salt; and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC(CH_2)_nCOOH$ where n is 0-4; organic amine salts such as triethylamine salt, pyridine salt, picoline salt, ethanolamine salt, triethanolamine salt, dicyclohexylamine salt, N,N'-dibenzylethylenediamine salt; and amino acid salts such as arginate, asparginate, and glutamate, and combinations comprising one or more of the foregoing salts.

An "effective amount" of a combination of agents (e.g., MEK and RAF inhibitors, or RAF and COT inhibitors, or RAF and an inhibitor targeting MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3)) is an amount sufficient to provide an observable improvement over the baseline clinically observable signs and symptoms of the disorder treated with the combination.

The pharmaceutical products can be administrated by oral or other forms, e.g., rectally or by parenteral injection. "Oral dosage form" is meant to include a unit dosage form prescribed or intended for oral administration. An oral dosage form may or may not comprise a plurality of subunits such as, for example, microcapsules or microtablets, packaged for administration in a single dose.

The pharmaceutical products can be released in various forms. "Releasable form" is meant to include instant release, immediate-release, controlled-release, and sustained-release forms.

"Instant-release" is meant to include a dosage form designed to ensure rapid dissolution of the active agent by modifying the normal crystal form of the active agent to obtain a more rapid dissolution.

"Immediate-release" is meant to include a conventional or non-modified release form in which greater than or equal to about 50% or more preferably about 75% of the active agents is released within two hours of administration, preferably within one hour of administration.

"Sustained-release" or "extended-release" includes the release of active agents at such a rate that blood (e.g., plasma) levels are maintained within a therapeutic range but below toxic levels for at least about 8 hours, preferably at least about 12 hours, more preferably about 24 hours after administration at steady-state. The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The term "treat", "treated," "treating" or "treatment" is used herein to mean to relieve, reduce or alleviate at least one symptom of a disease in a subject. For example, treatment can be diminishment of one or several symptoms of a disorder or complete eradication of a disorder, such as cancer. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the disease is associated with a cancer.

The term "subject" or "patient" is intended to include animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

As specified above, in one aspect, the instant invention provides a drug combination useful for treating, preventing, arresting, delaying the onset of and/or reducing the risk of developing, or reversing at least one symptom of cancer, in a subject comprising administering to the subject a combination therapy, comprising an effective amount of a RAF inhibitor and an effective amount of a MAP3K8 (TPL2/COT) inhibitor, or an effective amount of a RAF inhibitor and an effective amount of MEK inhibitor or an effective amount of a RAF inhibitor and an effective amount of a second inhibitor targeting MAP3K8 (TPL2/COT), RAF1 (CRAF), CRKL(CrkL), FGR (Fgr), PRKCE (Prkce), PRKCH (Prkch), ERBB2 (ErbB2), AXL (Axl), or PAK3 (Pak3). Preferably, these inhibitors are administered at therapeutically effective dosages which, when combined, provide a beneficial effect. The administration may be simultaneous or sequential.

The term "cancer" is used herein to mean a broad spectrum of tumors, including all solid tumors and hematological malignancies. Examples of such tumors include but are not limited to leukemias, lymphomas, myelomas, carcinomas, metastatic carcinomas, sarcomas, adenomas, nervous system cancers and geritourinary cancers. In exemplary embodiments, the foregoing methods are useful in treating adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor.

In particular, the cancer may be associated with a mutation in the B-RAF gene. These cancers include melanoma, breast cancer, colorectal cancers, glioma, lung cancer, ovarian cancer, sarcoma and thyroid cancer.

In a particular embodiment, the therapeutic combination provided herein is effective for the treatment of moderate to severe cancer in a subject.

Dosages

The optimal dose of the combination of agents for treatment of cancer can be determined empirically for each subject using known methods and will depend upon a variety of factors, including the activity of the agents; the age, body weight, general health, gender and diet of the subject; the time and route of administration; and other medications the subject is taking. Optimal dosages may be established using routine testing and procedures that are well known in the art.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above and is readily determined by one having skill in the art.

Generally, therapeutically effective doses of the compounds of this invention for a patient, when used for the indicated analgesic effects, will range from about 0.0001 to about 1000 mg per kilogram of body weight per day, more preferably from about 0.01 to about 50 mg per kg per day.

If desired, the effective daily dose of the active compound may be administered as two, three, four, five, six or more sub-doses administered separately at appropriate intervals throughout the day, optionally, in unit dosage forms.

Pharmaceutical Formulations and Routes of Administration

Provided herein are pharmaceutical formulations comprising a combination of agents for the treatment of cancer, e.g., melanoma. The pharmaceutical formulations may additionally comprise a carrier or excipient, stabilizer, flavoring agent, and/or coloring agent.

Provided herein are pharmaceutical formulations comprising combination of agents which can be, for example, a combination of two types of agents: (1) a RAF inhibitor and/or pharmacologically active metabolites, salts, solvates and racemates of the inhibitor and (2) a MAP3K8 (TPL2/COT) inhibitor and/or pharmacologically active metabolites, salts, solvates and racemates of the COT inhibitor. In another embodiment the combination of agents may be provided for a subject comprising BRAF mutant cells or comprising cells over expressing MAP3K8 (TPL2/COT) and include: (1) a RAF inhibitor and/or pharmacologically active metabolites, salts, solvates and racemates of the inhibitor and (2) a MEK inhibitor and/or pharmacologically active metabolites, salts, solvates and racemates of the MEK inhibitor.

The combination of agents may be administered using a variety of routes of administration known to those skilled in the art. The combination of agents may be administered to humans and other animals orally, parenterally, sublingually, by aerosolization or inhalation spray, rectally, intracisternally, intravaginally, intraperitoneally, bucally, or topically in dosage unit formulations containing conventional non-toxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono or di glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 □m. □ Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1 5 □m. □ Predominantly in this application means that at least 70% but preferably more than 90% of all generated aerosol particles are within 1 5 □m range. □ A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDESTREAM nebulizers (Medic Aid Ltd., West Sussex, England), PARI LC and PARI LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono or multi lamellar hydrated liquid crystals that are dispersed in an aqueous medium. Any non toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

EXAMPLES

Figure 1C:
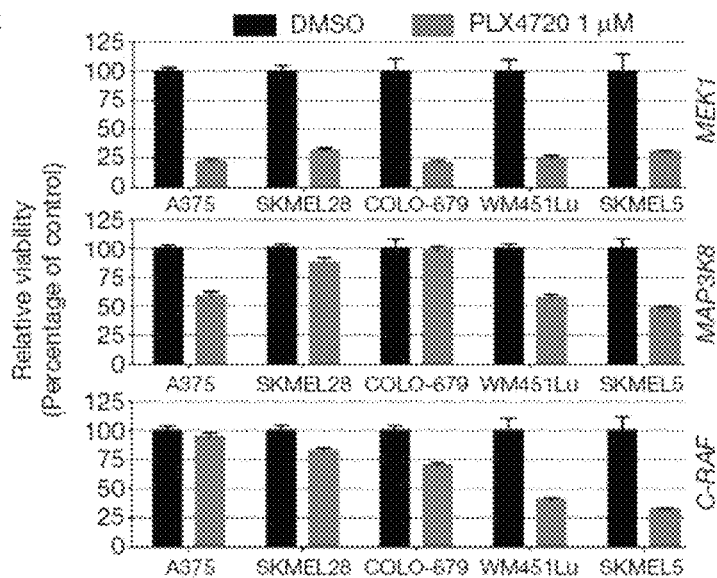
Figure 7:
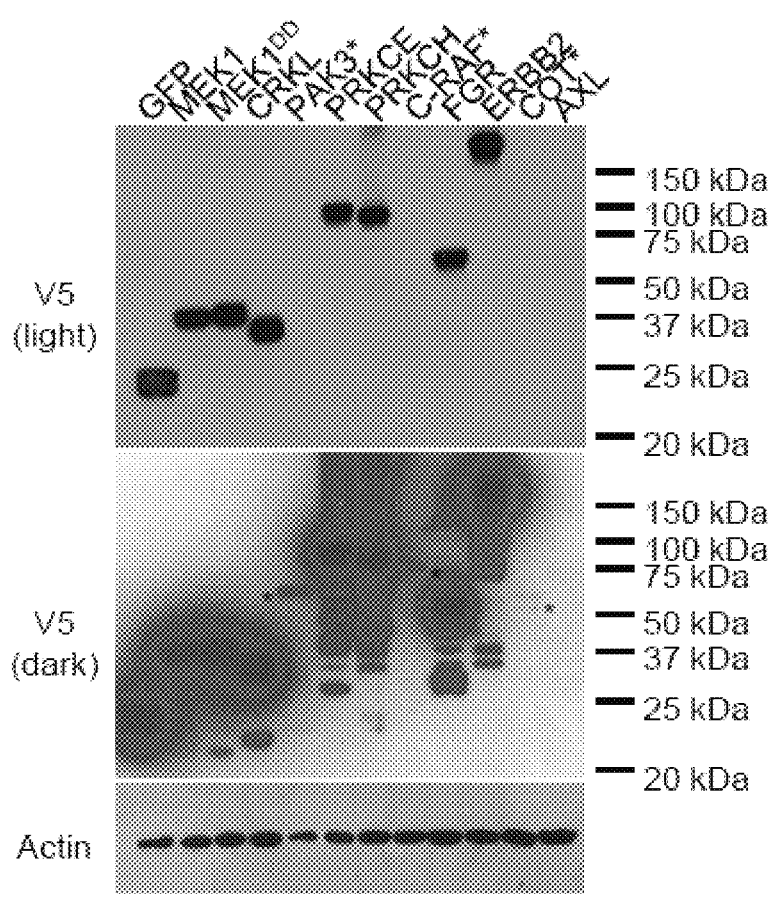
FIG. 7 illustrates the expression of candidate resistance ORFs. 293T were transiently transfected with pLX-BLAST-V5-ORF (indicated) and expression detected using an anti-V5-HRP antibody. The AXL clone is 'closed' and has a stop codon preceding the V5 tag. See FIG. 12 for verification of expression; (*) on dark-exposure indicate the expression of three ORFs not visible in the lighter exposure.
Figure 8:
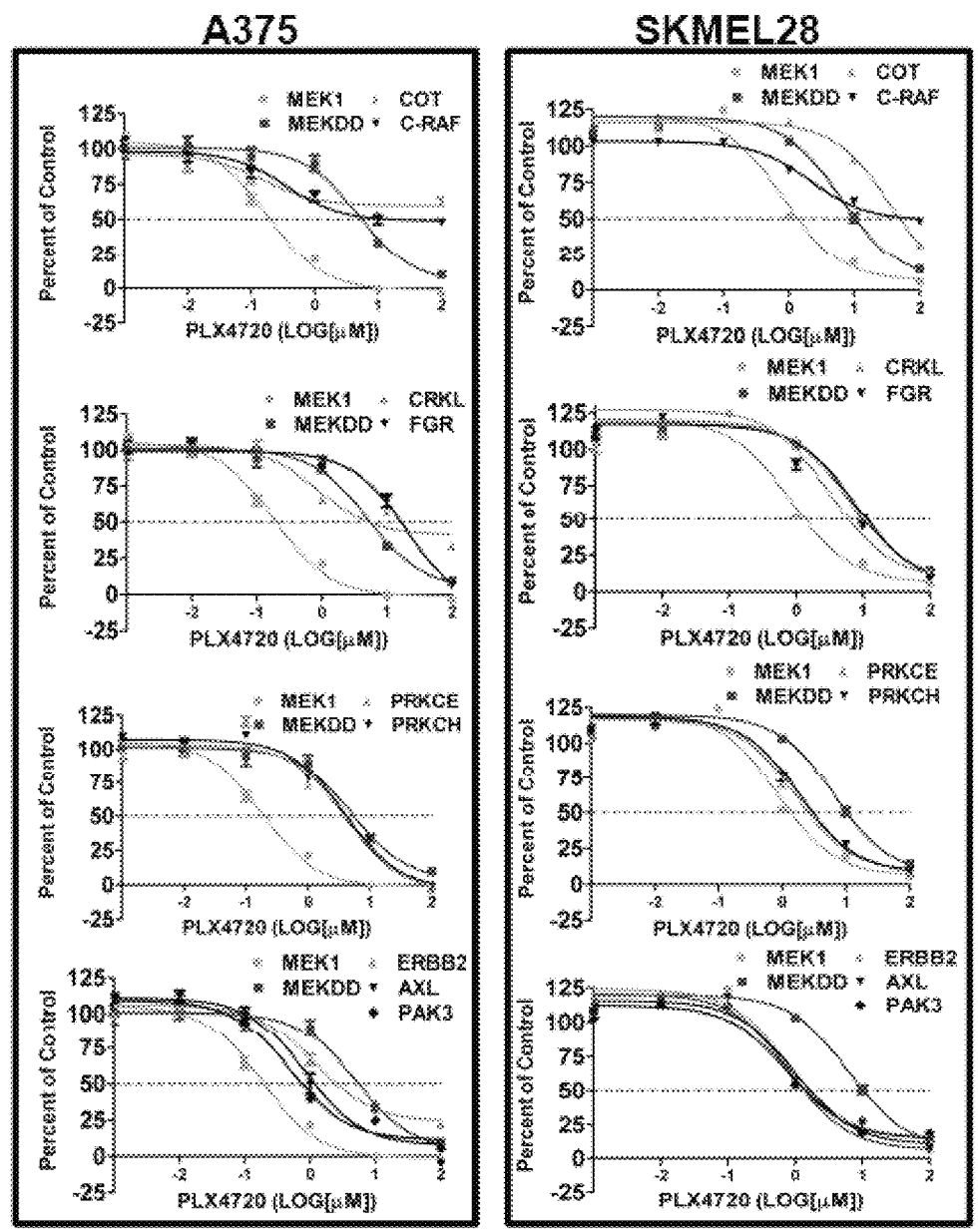
FIG. 8 illustrates that a secondary screen prioritizes the top 9 candidate B-RAF inhibitor resistance ORFs. The top nine ORFs scoring in the primary screen were expressed in A375 or SKMEL28 and a GI$_{50}$ from an 8-point PLX4720 concentration range.
Figures 9A, 9B:
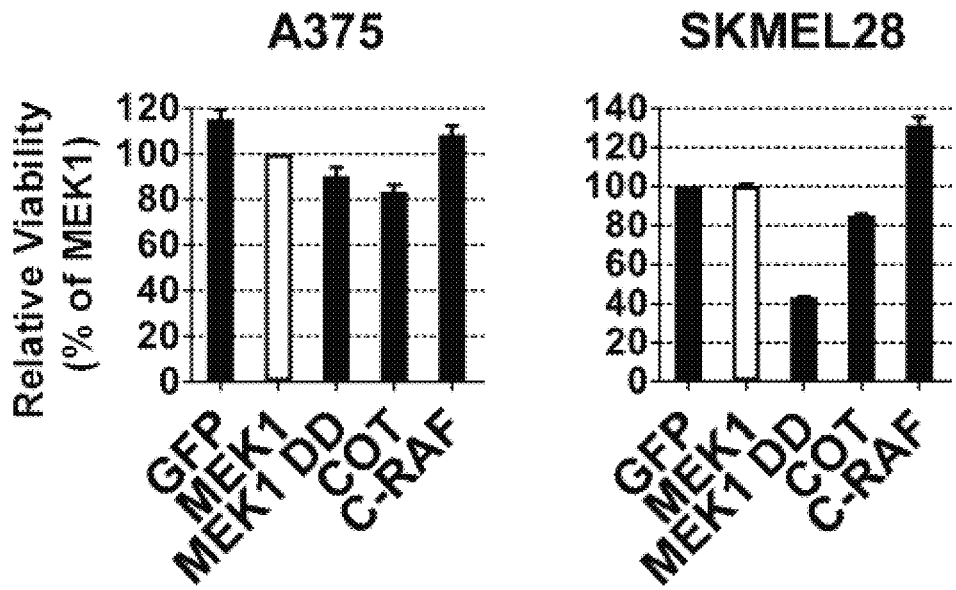
FIGS. 9A-9B illustrate the effects of ORF expression on proliferation in B-RAF$^{V600E}$ cell lines. Proliferation, relative to MEK1, in (a) A375 or (b) SKMEL28 expressing indicated ORFs after 7 days of growth.

Example 1: An ORF-Based Functional Screen Identifies Specific Kinases as Drivers of Resistance to B-RAF Inhibition To identify kinases capable of circumventing RAF inhibition, 597 sequence-validated kinase ORF clones representing ~75% of annotated kinases (Center for Cancer Systems Biology (CCSB)/Broad Institute Kinase ORF Collection) were assembled and stably expressed in A375, a B-RAF$^{V600E}$ malignant melanoma cell line that is sensitive to the RAF kinase inhibitor PLX4720 (Tsai, J. et al. *Proc. Natl Acad. Sci. USA* 105, 3041-3046 (2008)) (FIG. 1a, 1b, Table 3, FIG. 6c). ORF expressing cells treated with 1 µM PLX4720 were screened for viability relative to untreated cells and normalized to an assay-specific positive control, MEK1$^{S218/222D}$ (MEK1$^{DD}$) (Emery, C. M. et al. *Proc. Natl Acad. Sci. USA* 106, 20411-20416 (2009).) (Table 4 and summarized in FIG. 5). Nine ORFs conferred resistance at levels exceeding two standard deviations from the mean (FIG. 1b and Table 4) and were selected for follow-up analysis (FIG. 7). Three of nine candidate ORFs were receptor tyrosine kinases, underscoring the potential of this class of kinases to engage resistance pathways. Resistance effects were validated and prioritized across a multi-point PLX4720 drug concentration scale in the B-RAF$^{V600E}$ cell lines A375 and SKMEL28. The Ser/Thr MAP kinase kinase kinases (MAP3Ks) MAP3K8 (COT/Tpl2) and RAF1 (C-RAF) emerged as top candidates from both cell lines; these ORFs shifted the PLX4720 GI$_{50}$ by 10-600 fold without affecting viability (Table 5 and FIGS. 8 and 9). CRKL, an ORF that shifted the PLX4720 GI$_{50}$ to a lesser extent (9.7 fold in SKMEL28 cells; FIG. 8), encodes an adapter protein phosphorylated by tyrosine kinases such as BCR-ABL (Birge, R. B. et al., *Cell Commun Signal* 7, 13 (2009)), but lacks intrinsic kinase activity. COT and C-RAF reduced sensitivity to PLX4720 in multiple B-RAF$^{V600E}$ cell lines (FIG. 1c) confirming the ability of these kinases to mediate resistance to RAF inhibition. A secondary screen in A375 and SKMEL28 prioritizes the top 9 candidate ORFs across a multipoint PLX4720 concentration scale (FIG. 1d).

Interestingly, the top two validated kinases are both Ser/Thr MAP kinase kinase kinases (MAP3Ks) known to activate MEK/ERK signaling in several contexts. Like B-RAF, C-RAF is a MAP3K in the canonical MAPK cascade (McKay, M. M. and Morrison, D. K. *Oncogene* 26, 3113-3121 (2007)) that was previously implicated in resistance associated with stepwise selection in vitro using a pan-RAF inhibitor (Montagut, C. et al. *Cancer Res* 68, 4853-4861 (2008)). COT (the protein product of the human MAP3K8 gene) is best characterized as the MAP3K (Salmeron, A. et al. *EMBO J* 15, 817-826 (1996)) downstream of NFKB signaling in inflammatory cells (Banerjee, A. et al., *Proc Natl Acad Sci U.S.A.* 103, 3274-3279 (2006)); however, its functional importance in human cancer has not previously been elucidated.

Example 2: Resistance to B-RAF Inhibition Via MAPK Pathway Activation

Figure 10:
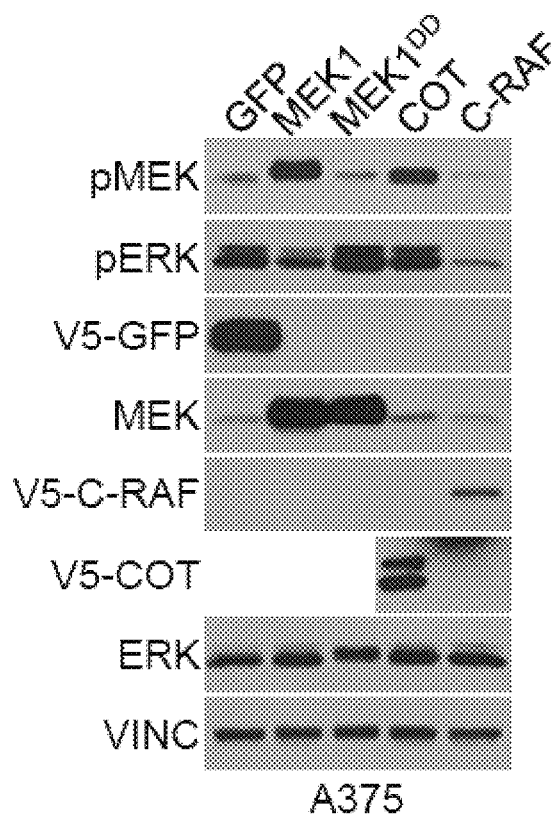
FIG. 10 illustrates that ectopic expression of constitutively active MEK1 (MEK1$^{DD}$) and COT lead to increased pMEK/pERK in A375, whereas C-RAF reduces pMEK/pERK levels. Lysates from A375 ectopically expressing GFP, MEK1, MEK$^{DD}$, COT or C-RAF were analyzed via immunoblot for levels of pERK and pMEK. GFP and MEK1 (lanes 1-3) were separated from COT/C-RAF (lanes 4-5) to prevent residual V5-MEK1 signal from overwhelming that of COT and C-RAF, which are expressed at much lower levels.
Figure 12:
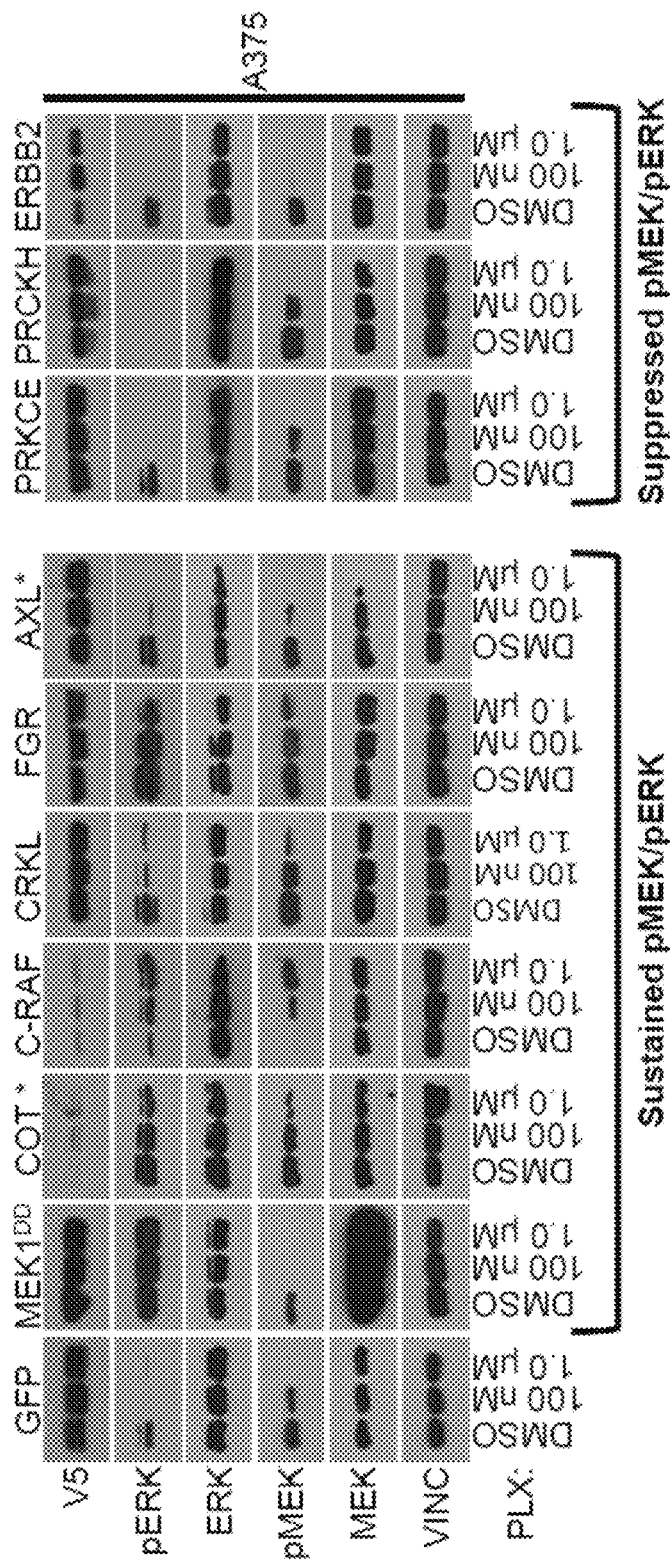
FIG. 12 illustrates the effects of ORF expression on MAPK signaling in the context of the B-RAF inhibitor PLX4720. MAPK pathway activation was assessed by immunoblot analysis of pERK and pMEK in A375 expressing the indicated ORFs in the presence of PLX4720 (18 h., concentration indicated). (*) indicates the use of an antibody directed against the expressed ORF, not the V5 epitope. AXL was cloned without the V5 tag.

Whether the overexpression of these genes was sufficient to activate the MAPK pathway was also tested. At baseline, COT expression increased ERK phosphorylation in a manner comparable to MEK1$^{DD}$, consistent with MAP kinase pathway activation (FIGS. 2a and 10). Overexpression of wild-type COT or C-RAF resulted in constitutive phosphorylation of ERK and MEK in the presence of PLX4720, whereas kinase-dead derivatives had no effect (FIGS. 2a and 11). Thus, COT and C-RAF drive resistance to RAF inhibition predominantly through re-activation of MAPK signaling. Notably, of the nine candidate ORFs from the initial screen, a subset (3) did not show persistent ERK/MEK phosphorylation following RAF inhibition, suggesting MAPK pathway-independent alteration of drug sensitivity (FIG. 12).

Example 3: C-RAF Activation and Heterodimerization with B-RAF

Figure 14A:
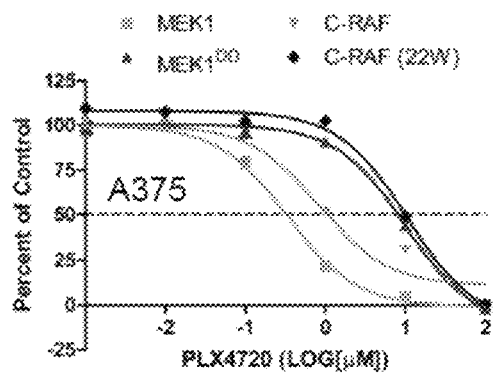
FIGS. 14A-14B illustrate that Retroviral expression of a wild-type C-RAF or a high-activity truncation mutant of C-RAF (C-RAF(22W)) renders A375 resistant to the B-inhibitor PLX4720 (a) and leads to sustained pERK levels in the context of PLX4720 treatment (1 μM, 18 h.), (b). C-RAF expression levels achieved with retroviruses are significantly lower than with lentiviral-based systems, resulting in a lower GI$_{50}$ than that achieved with lentiviral C-RAF.
Figure 14B:
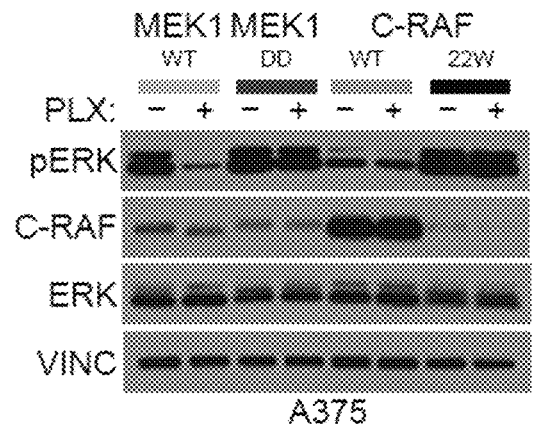

C-RAF activation and heterodimerization with B-RAF constitute critical components of the cellular response to B-RAF inhibition. In A375 cells, endogenous C-RAF: B-RAF heterodimers were measurable and inducible following treatment with PLX4720 (FIG. 13). However, endogenous C-RAF phosphorylation at S338—an event required for C-RAF activation—remained low (FIG. 13). In contrast, ectopically expressed C-RAF was phosphorylated on S338 (FIG. 13) and its PLX4720 resistance phenotype was associated with sustained MEK/ERK activation (FIGS. 2a and 13). Moreover, ectopic expression of a high-activity C-RAF truncation mutant (C-RAF(W22)) was more effective than wild-type C-RAF in mediating PLX4720 resistance and ERK activation (FIG. 14), further indicating that elevated C-RAF activity directs resistance to this agent. Consistent with this model, oncogenic alleles of NRAS and KRAS conferred PLX4720 resistance in A375 cells (FIG. 2b) and yielded sustained C-RAF(S338) and ERK phosphorylation in the context of drug treatment (FIG. 2c). Thus, although genetic alterations that engender C-RAF activation (e.g., oncogenic RAS mutations) tend to show mutual exclusivity with B-RAF$^{V600E}$ mutation, such co-occurring events are favored in the context of acquired resistance to B-RAF inhibition.

Example 4: Investigation of COT Expression in Melanoma

While C-RAF has been linked previously to melanoma and MAPK pathway dependencies (Montagut, C. et al. 2008; Karreth, F. A., DeNicola, G. M. et al., 2009; Dumaz, N. et al. *Cancer Res* 66, 9483-9491 (2006); Hatzivassiliou, G. et al. *Nature* (2010); Heidorn, S. J. et al., *Cell* 140, 209-221 (2010); Poulikakos, P. I. et al., *Nature* (2010)), COT has not been described as a melanoma-associated kinase.

Figure 15A:
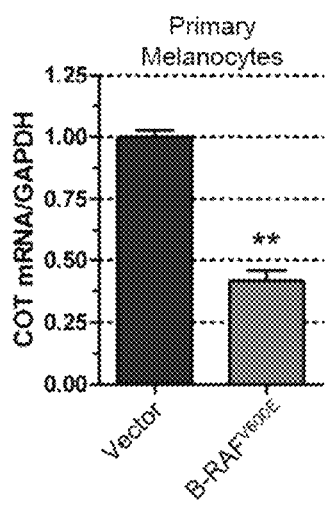
FIGS. 15A-15B illustrate the effects of B-RAF$^{V600E}$ on COT mRNA (a) Quantitative RT/PCR of COT mRNA expression relative to GAPDH mRNA expression in transformed primary melanocytes expressing wild-type B-RAF (vector) or B-RAF$^{V600E}$. COT expression was normalized to that of vector-expressing primary melanocytes. (**) Significant, p 0.05 (Student's two-tailed, paired T-Test). Endogenous COT mRNA is undetectable in PLX4720-sensitive A375 and ectopically expressed COT mRNA levels are unaffected by 1 μM PLX4720 treatment. A375 expressing GFP or COT were treated for 18 h. with 1 μM PLX4720. Reverse-transcribed mRNA was analyzed for GAPDH-normalized COT expression, relative to GFP-expressing, DMSO treated, A375. (*) Not significant, p>0.05 (Student's two-tailed, paired T-Test). Error bars represent SEM.
Figure 15B:
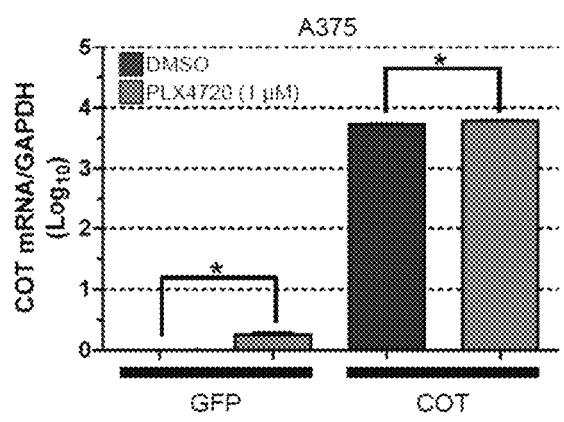
Figure 16:
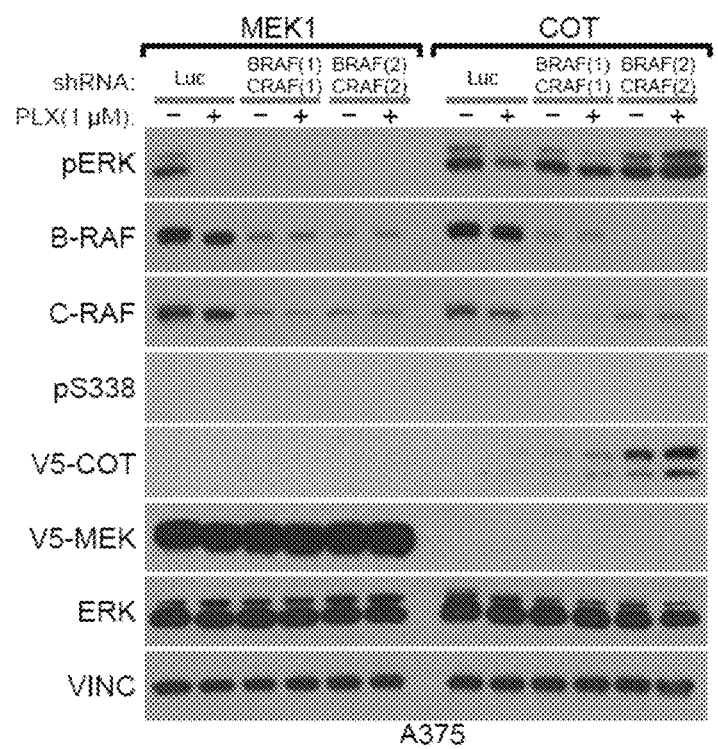
FIG. 16 illustrates that B- and C-RAF protein levels are not required for COT-mediated ERK phosphorylation. A375 expressing ectopic MEK1 (control) or COT were sequentially infected with lentivirus expressing shRNAs targeting B-RAF, C-RAF or control shRNA (shLuc) and assayed for expression of the indicated proteins in the presence (+) or absence (−) of 1 μM PLX4720, 18 h.

The role of COT in melanoma was investigated, and its expression in human melanocytes was examined. Primary immortalized melanocytes (B-RAF wild-type) expressed COT (FIG. 2d), although ectopic B-RAF$^{V600E}$ expression reduced COT mRNA levels (FIG. 15) and rendered COT protein undetectable (FIG. 2d). Conversely, whereas ectopically expressed COT was only weakly detectable in A375 cells (FIGS. 2a, 2e), shRNA-mediated depletion of endogenous B-RAF$^{V600E}$ caused an increase in COT protein levels that correlated with the extent of B-RAF knockdown (FIG. 2e). Moreover, treatment of COT-expressing A375 cells with PLX4720 led to a dose-dependent increase in COT protein (FIG. 2a) without affecting ectopic COT mRNA levels (FIG. 15). Oncogenic B-RAF antagonizes COT expression largely through altered protein stability (FIGS. 2a, d, e, and 15), and B-RAF inhibition potentiates the outgrowth of COT-expressing cells during the course of treatment. Notably, neither C-RAF nor B-RAF alone or in combination was required for ERK phosphorylation in the context of COT expression, even in the presence of PLX4720 (FIGS. 2e, 2f and FIG. 16). As shown, COT expression is sufficient to induce MAP kinase pathway activation in a RAF-independent manner.

Figure 3J:
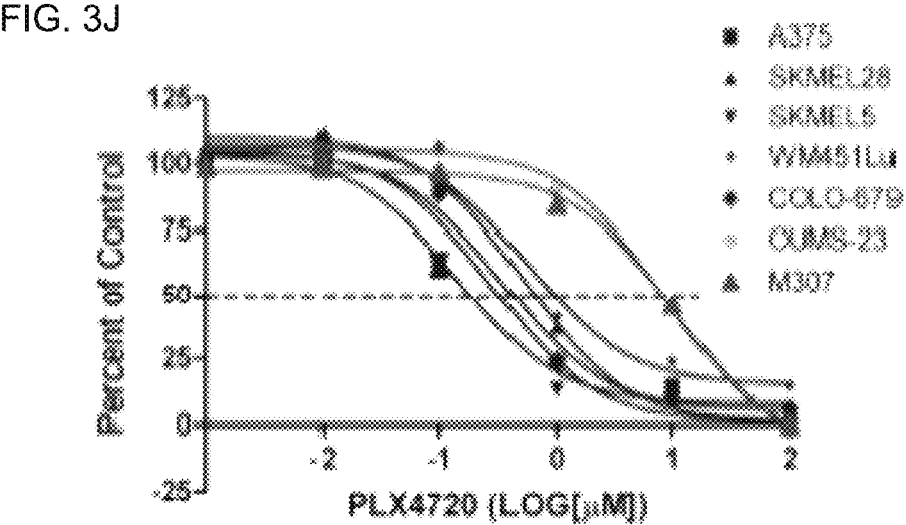
Figure 3K:
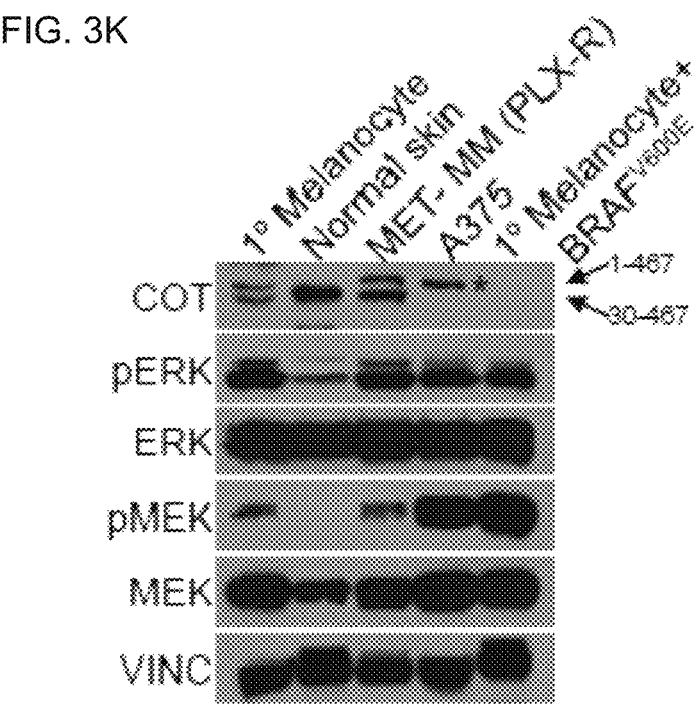
Figure 17:
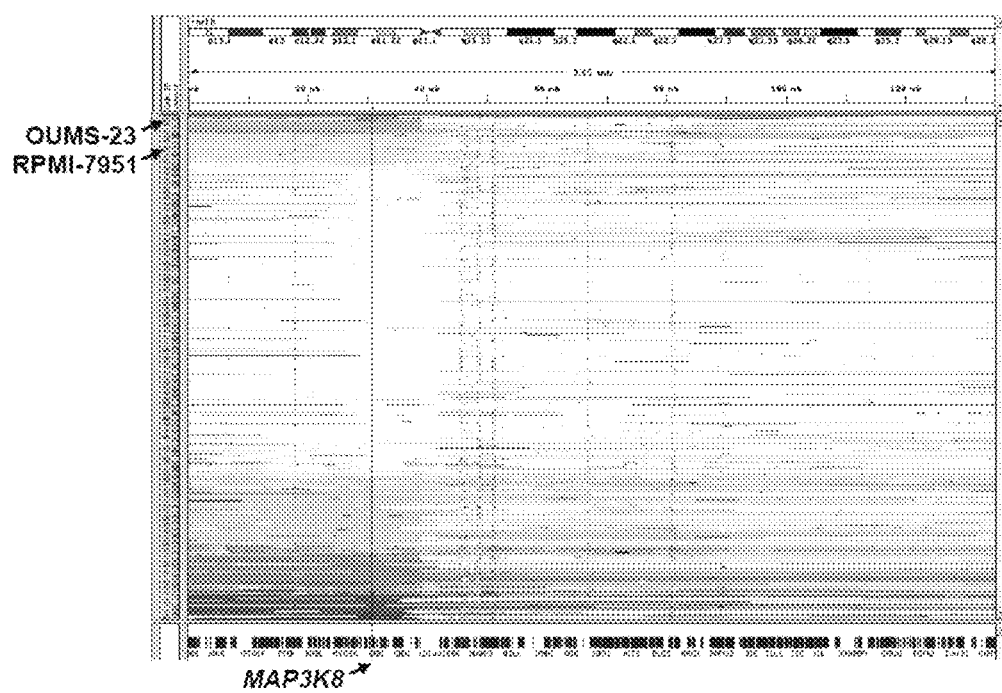
FIG. 17 illustrates SNP analysis of 752 cell lines reveals copy number alterations in MAP3K8/COT. Of the 752 cell lines hat had undergone copy number analysis, 534 had also undergone mutation profiling. Thirty-eight (7.1%) of mutation-profiled cells harbor the B-RAF$^{V600E}$ mutation. Two cell lines (OUMS-23, RPMI-7951, indicated) harbor the B-RAF$^{V600E}$ mutation along with copy number gain in MAP3K8/COT.
Figure 18B:
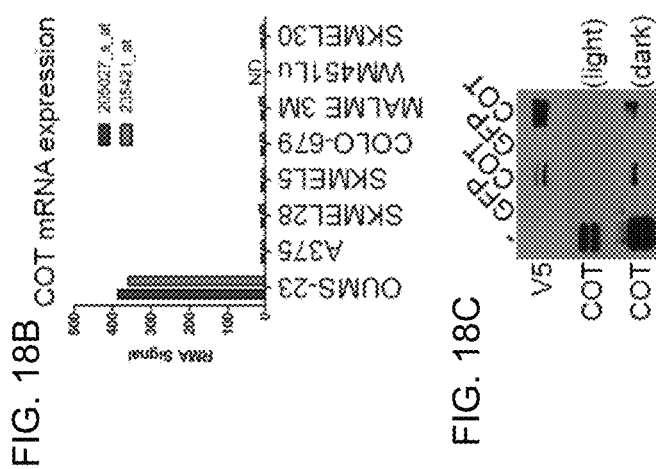
Figure 18A:
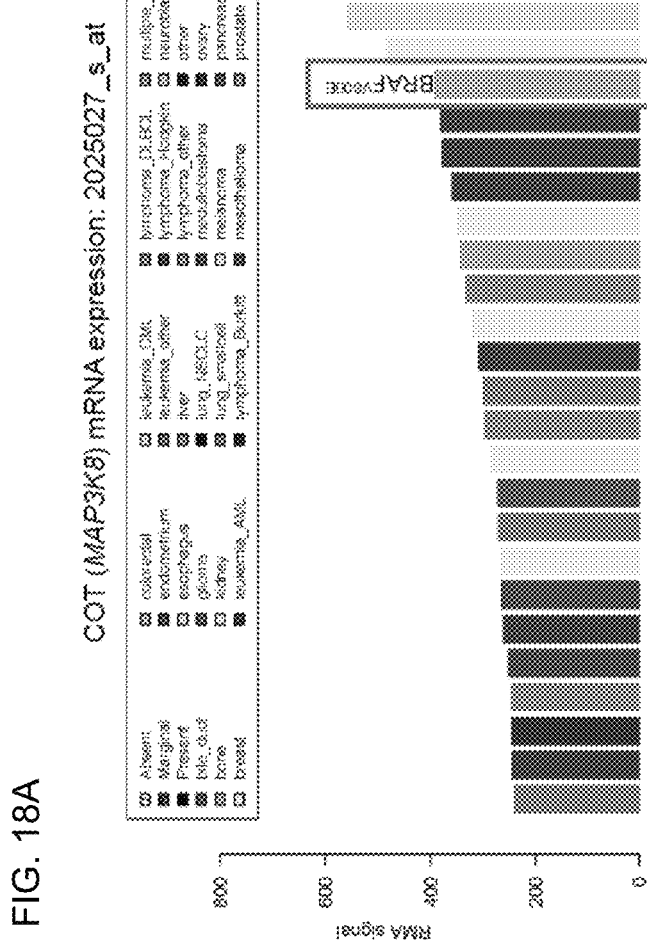

Example 5: COT Expression Predicts Resistance to B-RAF Inhibition in Cancer Cell Lines Whether cell lines expressing elevated COT in a B-RAF$^{V600E}$ background exhibit de novo resistance to PLX4720 treatment was tested. To identify such instances, a panel of cell lines was screened for evidence of MAP3K8/COT copy number gains coincident with the B-RAF$^{V600E}$ mutation. Of 534 cell lines that had undergone copy number analysis and mutation profiling, 38 cell lines (7.1%) contained the B-RAF$^{V600E}$ mutation. Within this subgroup, two cell lines—OUMS-23 (colon cancer) and RPMI-7951 (melanoma)—also showed evidence of chromosomal copy gains spanning the MAP3K8/COT locus (FIGS. 3a and 17) and robust COT protein expression (FIGS. 3b and 18). A panel of melanoma short-term cultures was also screened for COT protein expression. One of these lines expressed COT: M307, a short-term culture derived from a B-RAF$^{V600E}$ tumor that developed resistance to allosteric MEK inhibition following initial disease stabilization (FIG. 3c). All three cell lines were refractory to PLX4720 treatment, exhibiting GI$_{50}$ values in the range of 8-10 μM (FIG. 3d) and showing sustained ERK phosphorylation in the context of B-RAF inhibition (FIGS. 3e, 3f). OUMS-23 and RPMI-7951 are MAPK pathway inhibitor-naïve cell lines; thus, these results demonstrate that COT confers de novo resistance to RAF inhibition (a phenomenon observed in ~10% of B-RAF$^{V600E}$ melanomas).

Example 6: COT Expression in Patients Treated with a RAF Inhibitor

Figure 19B:
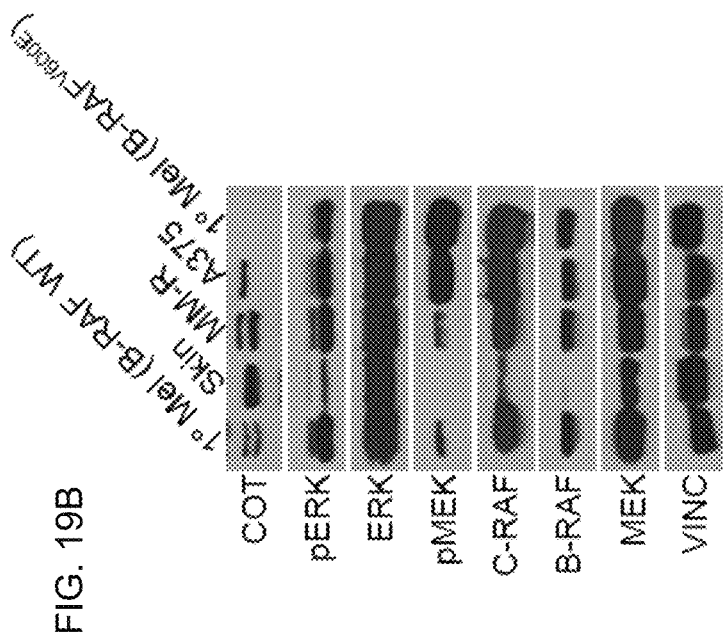
FIGS. 19A-19B illustrate that COT mRNA and protein are expressed in B RAF-inhibitor resistant cell lines and tissue. (a) RT/PCR analysis of GAPDH normalized COT mRNA expression in a panel of cell lines, short term cultures and tissue from relapsed, PLX4032-treated, malignant melanoma (MM-R). Corresponding protein expression for cell lines and short term cultures are shown in FIGS. 3b and 3c, respectively. (b) Western blot analysis of lysates from primary melanocytes (1° Mel(B-RAF WT)), patient matched normal skin (Skin) and metastatic malignant melanoma (MM-R; COT mRNA shown in panel a), A375 cells and primary melanocytes expressing B-RAF$^{V600E}$ (1° Mel (B-RAFV600E)).
Figure 19A:
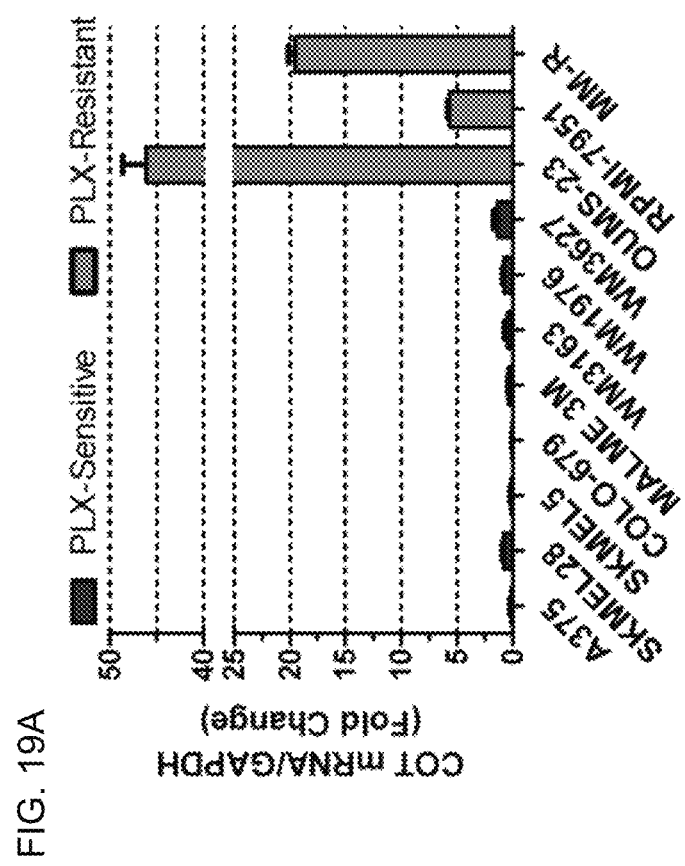

COT expression in the context of resistance to the clinical RAF inhibitor PLX4032 was examined by obtaining biopsy material from 3 patients with metastatic, B-RAF$^{V600E}$ melanoma. Each case consisted of frozen, lesion-matched biopsy material obtained prior to and during treatment ("pre-treatment" and "on-treatment"; FIG. 3g, Table 6); additionally, one sample contained two independent biopsy specimens from the same relapsing tumor site ("post-relapse"; FIG. 3g). Consistent with the experimental models presented above, quantitative real-time RT-PCR (qRT/PCR) analysis revealed increased COT mRNA expression concurrent with PLX4032 treatment in 2 of 3 cases. COT mRNA levels were further increased in a relapsing specimen relative to its pre-treatment and on-treatment counterparts (FIG. 3g, Patient #1). An additional, unmatched relapsed malignant melanoma biopsy showed elevated COT mRNA expression comparable to levels observed in RAF inhibitor-resistant, COT-amplified cell lines (FIG. 19). This specimen also exhibited robust MAPK pathway activation and elevated expression of B-RAF, C-RAF and COT relative to matched normal skin or B-RAF$^{V600E}$ cell lines (FIG. 19). Sequencing studies of this tumor revealed no additional mutations in BRAF, NRAS or KRAS (data not shown). These analyses provided clinical evidence that COT-dependent mechanisms are operant in PLX4032-resistant malignant melanomas.

Example 7: COT Regulation of MEK/ERK Phosphorylation

Whether COT actively regulates MEK/ERK phosphorylation in B-RAF$^{V600E}$ cells that harbor naturally elevated COT expression was tested by introducing shRNA constructs targeting COT into RPMI-7951 cells. Depletion of COT suppressed RPMI-7951 viability (FIG. 20) and decreased ERK phosphorylation (FIG. 3h); thus, targeting COT kinase activity suppresses MEK/ERK phosphorylation in cancer cells with COT overexpression or amplification. Additionally, the targeting COT kinase activity in the presence of a B-RAF inhibitor (PLX4720) suppresses MEK/IRK phosphorylation (FIG. 3h). Treatment of RPMI-7951 cells with a small molecule COT kinase inhibitor (Wyeth, Abbot compound ID 9549300) (George, D. et al., *Bioorg. Med. Chem. Lett.* 18, 4952-4955 (2008); Hirata, K. et al., *Biol. Pharm. Bull.* 33, 133-137 (2010); Lee, K. M. et al., *Cancer Res.* 69, 8043-8049 (2009)) resulted in dose-dependent suppression of MEK and ERK phosphorylation, providing additional evidence that COT contributes to MEK/ERK activation in these cells (FIG. 3i).

Figure 4B:
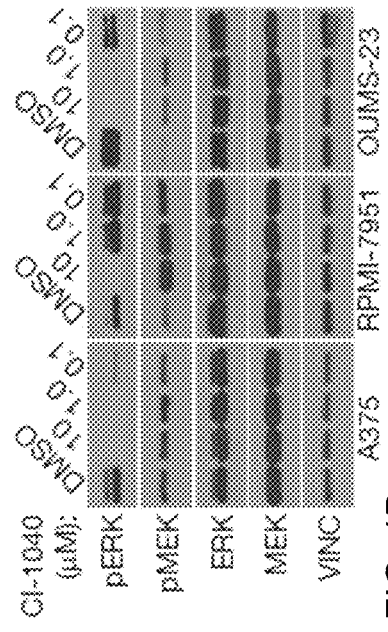
FIGS. 4A-4I illustrate COT-expressing B-RAFV600E cell lines exhibit resistance to allosteric MEK inhibitors. (a) CI-1040 GI50 in a panel of B-RAF$^{V600E}$ cell lines; (b) MEK and ERK phosphorylation in lysates from indicated cell lines treated with DMSO or CI-1040 (concentration noted); (c) Fold change (relative to MEK1) GI50 of A375 ectopically expressing the indicated ORFs for PLX4720, RAF265, CI-1040 and AZD6244; (d) ERK phosphorylation in A375 expressing indicated ORFs following treatment with DMSO or 1 µM of PLX4720, RAF265, CI-1040 or AZD6244; (e) Viability of A375 expressing the indicated ORFs and treated with DMSO, PLX4720 (concentration indicated) and PLX4720 in combination with CI-1040 or AZD6244 (all 1 µM). Error bars represent the standard deviation (n=6); (f) ERK phosphorylation in A375 expressing indicated ORFs following treatment with DMSO, PLX4720 (1 µM) or PLX4720 in combination with CI-1040 or AZD6244 (all 1 µM); (g) Cell lines with aberrant MAP3K8/COT copy number/expression are insensitive to the allosteric MEK inhibitor CI-1040 or (h) AZD6244; (i) A schematic outlining the formation of MAP3K complexes in response to B-RAF inhibition in B-RAF$^{V600E}$-mutant cell lines. PLX4720 positions C-RAF in a signaling-competent complex (upper right panel) that is activated by oncogenic events upstream of C-RAF (lower right panel), subsequently driving resistance. In the context of COT expression, COT/RAF-containing complexes are sufficient to activate the MAPK pathway and mediate resistance (lower left panel).
Figure 4D:
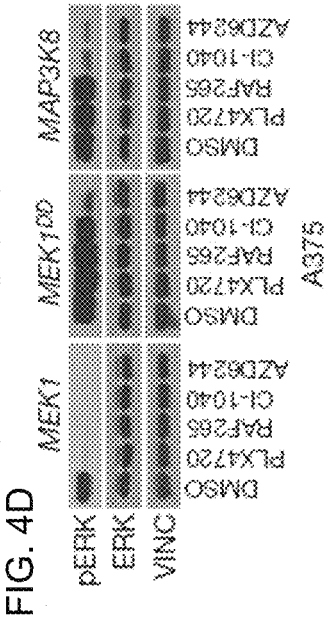
Figure 4F:
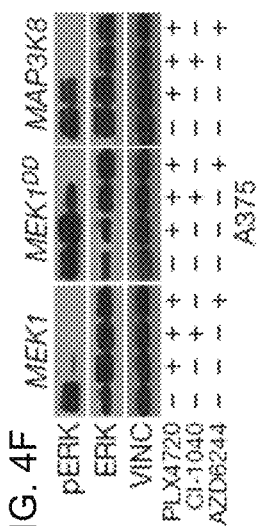
Figure 4A:
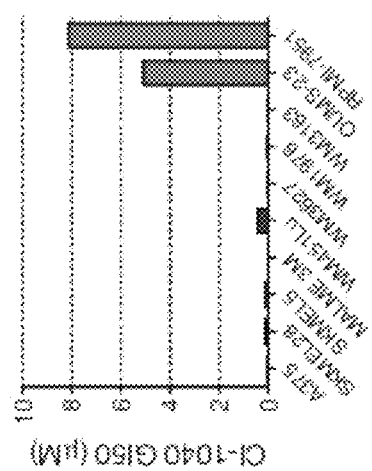
Figure 4C:
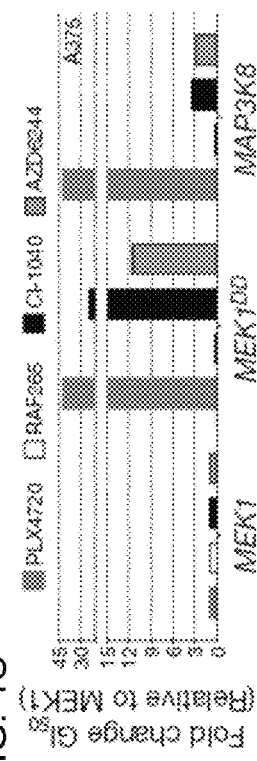
Figure 21:
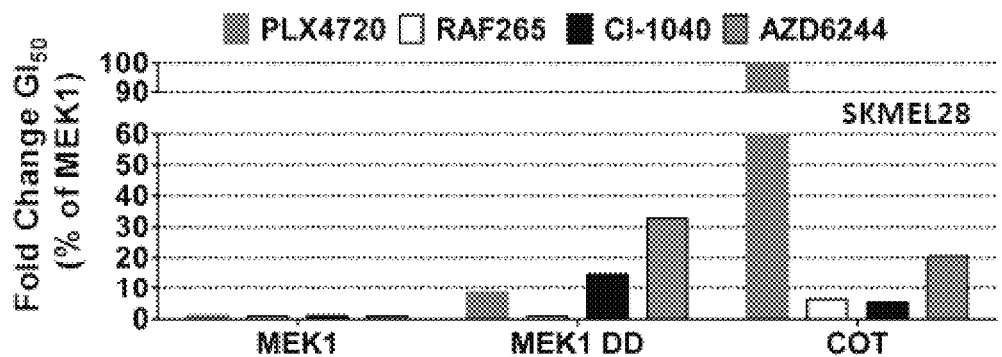
FIG. 21 illustrates effects of ORF expression on the GI$_{50}$ of a panel of MAPK pathway inhibitors in SKMEL28. The half-maximal growth-inhibitory concentration (GI$_{50}$) of SKMEL28 ectopically expressing MEK1, MEK1$^{DD}$ or COT was determined for the RAF inhibitors PLX4720 and RAF265 and the MEK1/2 inhibitors CI-1040 and AZD6244. The change in GI$_{50}$ for MEK1$^{DD}$ and COT (relative to MEK1) was determined for each compound.
Figure 24:
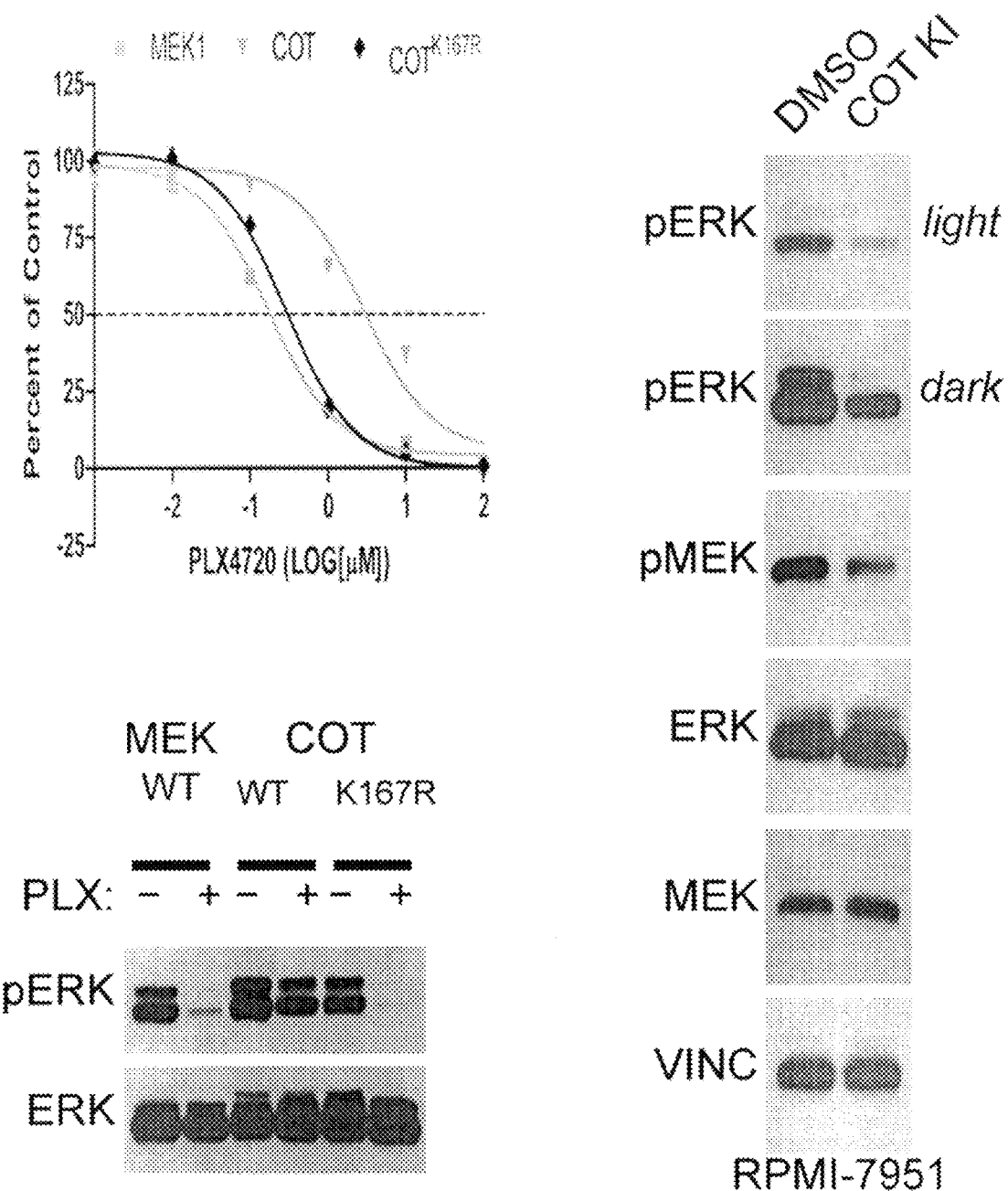
FIG. 24 illustrates that COT over expression is sufficient to render melanoma cancer cells with the B-RAF$^{V600E}$ mutation resistant to B-RAF inhibition.
Figure 25A:
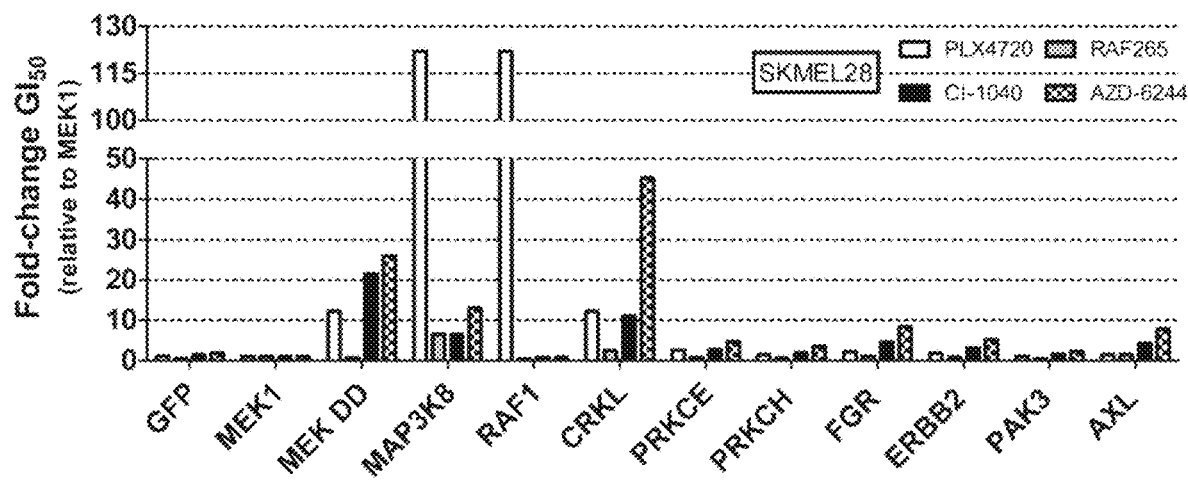
FIGS. 25A-25B illustrate the top nine ORFs scoring in the primary screen were expressed in (a) SKEL28 of (b) A375 and aGI50 is shown for 4 MAPK pathway inhibitors (PLX4720, RAF265, CI-1040, AZD-6244).
Figure 25B:
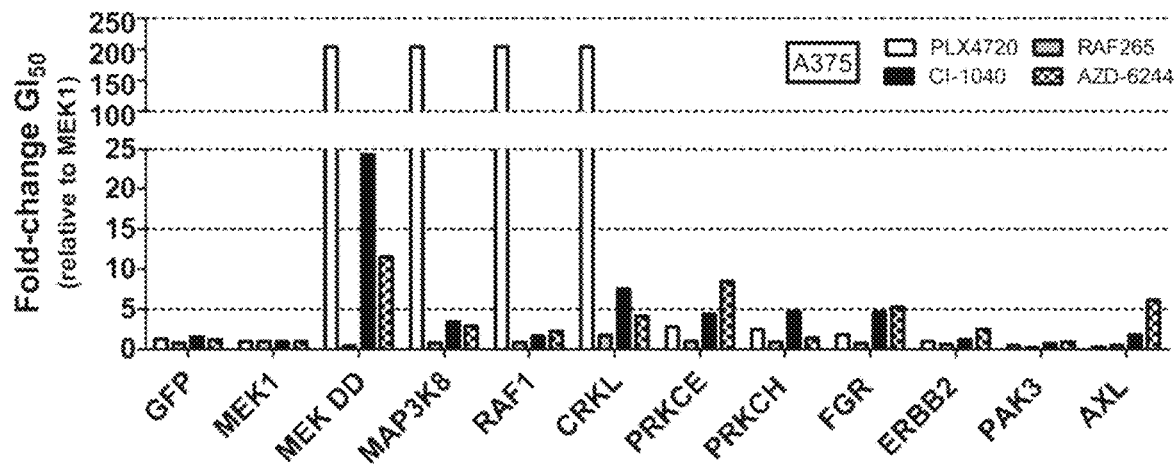
Figure 26:
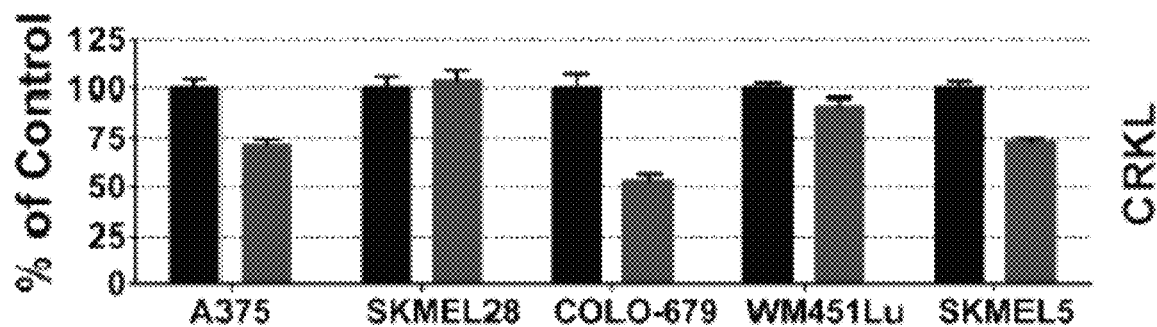
FIG. 26 illustrates that CRKL expression modifies sensitivity to the selective B-RAF inhibitor PLX4720 in a panel of B-RAFv600E cell lines.
Figure 27:
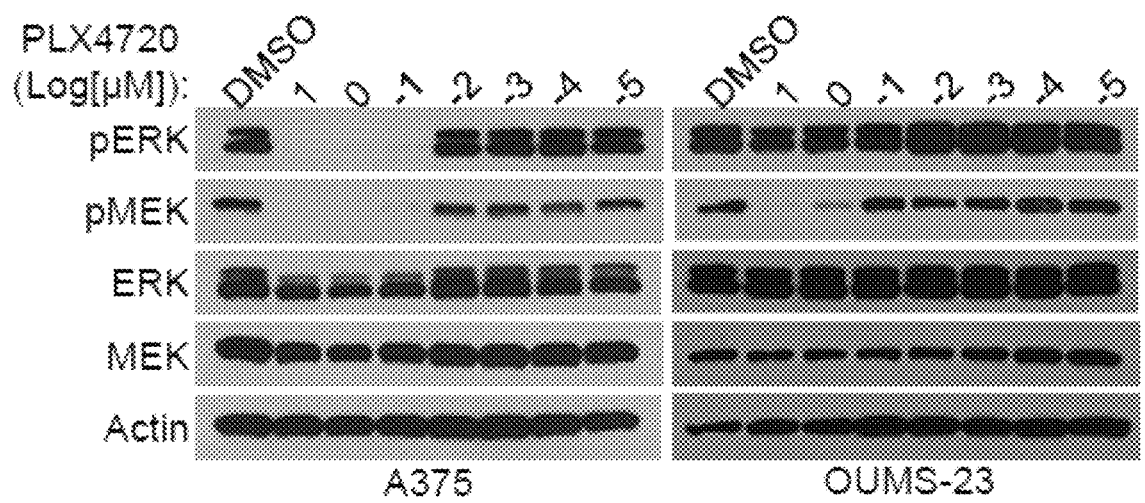
FIG. 27 illustrates the MAP3K8/COT-amplified/B-RAF$^{V600E}$-mutant cancer cell line OUMS-23 shows constitutive phosphorylation of ERK/MEK across a dose range of PLX4720.

Example 8: COT-Expressing B-RAF$^{V600E}$ Cell Lines Exhibit Resistance to Allosteric MEK Inhibitors Whether COT-expressing cancer cells remain sensitive to MAPK pathway inhibition at a target downstream of COT or RAF was analyzed. The OUMS-23 and RPMI-7951 cell lines were queried for sensitivity to the MEK1/2 inhibitor CI-1040. Both cell lines were refractory to MEK inhibition (FIG. 4a) and displayed sustained ERK phosphorylation even at 1 μM CI-1040 (FIG. 4b). Ectopic COT expression in A375 and SKMEL28 cells also conferred decreased sensitivity to the MEK inhibitors CI-1040 and AZD6244, suggesting that COT expression alone was sufficient to induce this phenotype (FIGS. 4c, 4d and 21). Similar to results observed with pharmacological MEK inhibitors, MEK1/2 knockdown only modestly suppressed COT-mediated ERK phosphorylation in A375 cells (FIG. 22). These data demonstrate that COT activates ERK through MEK-independent and MEK-dependent mechanisms. Furthermore, an in vitro kinase assay using recombinant COT and ERK1 was performed, and it was demonstrated that recombinant COT induced pThr202/Tyr204 phosphorylation of ERK1 in vitro (FIG. 22). Thus, COT expression potentiates ERK activation in a MEK-independent manner.

Example 9: Combinatorial MAPK Pathway Inhibition to Suppress Cell Proliferation

Figure 4E:
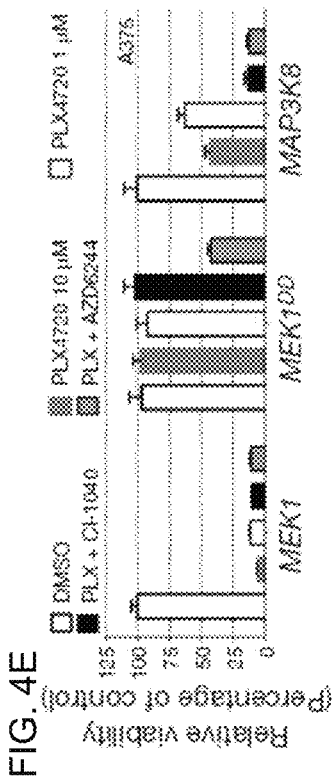
Figure 4G:
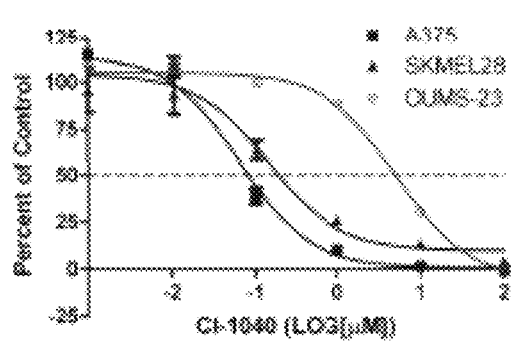
Figure 4H:
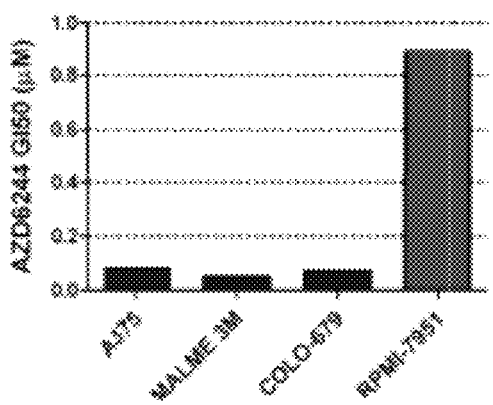
Figure 4I:
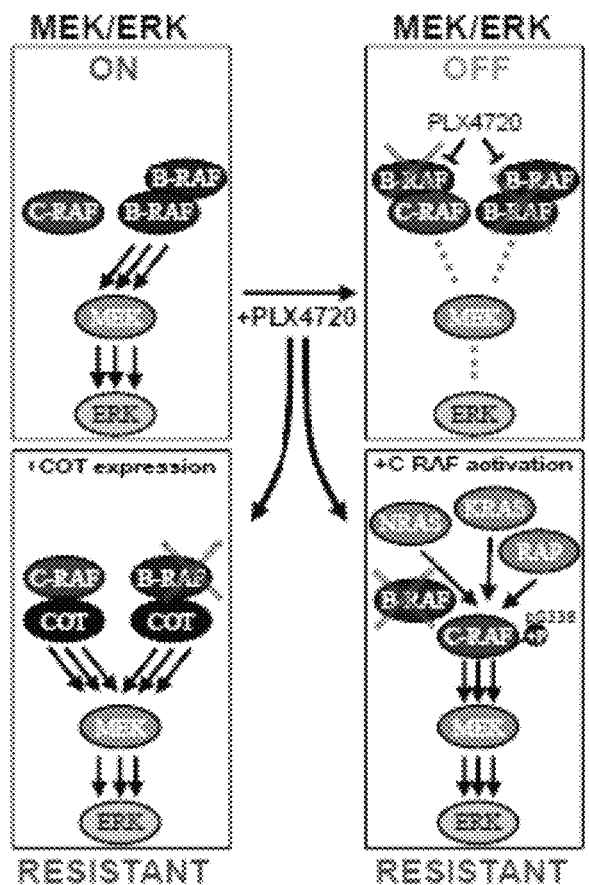

The use of RAF and MEK inhibitors in combination can override resistance to single-agents as shown in FIG. 23. It was tested whether the combined RAF/MEK inhibition might circumvent COT-driven resistance. In the setting of ectopic COT expression, exposure to AZD6244 or CI-1040 in combination with PLX470 (1 μM each) reduced cell growth and pERK expression more effectively than did single-agent PLX4720, even at concentrations of 10 μM (FIGS. 4e, 4f and 23). These data underscore the importance of this pathway in B-RAF$^{V600E}$ tumor cells and demonstrate that dual B-RAF/MEK inhibition helps circumvent resistance to RAF inhibitors.

Methods

Center for Cancer Systems Biology (CCSB)/Broad Institute Kinase Open Reading Frame Collection A library of 597 kinase ORFs in pDONR-223 Entry vectors (Invitrogen) was assembled. Individual clones were end-sequenced using vector-specific primers in both directions. Clones with substantial deviations from reported sequences were discarded. Entry clones and sequences are available via Addgene (http://www.addgene.org/human_kinases). Kinase ORFs were assembled from multiple sources; 337 kinases were isolated as single clones from the ORFeome 5.1 collection (http://horfdb.dfci.harvard.edu), 183 kinases were cloned from normal human tissue RNA (Ambion) by reverse transcription and subsequent PCR amplification to add Gateway sequences (Invitrogen), 64 kinases were cloned from templates provided by the Harvard Institute of Proteomics (HIP), and 13 kinases were cloned into the Gateway system from templates obtained from collaborating laboratories. The Gateway-compatible lentiviral vector pLX-Blast-V5 was created from the pLKO.1 backbone. LR Clonase enzymatic recombination reactions were performed to introduce the 597 kinases into pLX-Blast-V5 according to the manufacturer's protocol (Invitrogen).

High Throughput ORF Screening

A375 melanoma cells were plated in 384-well microtiter plates (500 cells per well). The following day, cells were spin-infected with the lentivirally-packaged kinase ORF library in the presence of 8 ug/ml polybrene. 48 hours post-infection, media was replaced with standard growth media (2 replicates), media containing 1 μM PLX4720 (2 replicates, 2 time points) or media containing 10 ug/ml blasticidin (2 replicates). After four days and 6 days, cell growth was assayed using Cell Titer-Glo (Promega) according to manufacturer instructions. The entire experiment was performed twice.

Identification of Candidate Resistance ORFs

Raw luminescence values were imported into Microsoft Excel. Infection efficiency was determined by the percentage of duplicate-averaged raw luminescence in blasticidin selected cells relative to non-selected cells. ORFs with an infection efficiency of less than 0.70 were excluded from further analysis along with any ORF having a standard deviation of >15,000 raw luminescence units between duplicates. To identify ORFs whose expression affects proliferation, we compared the duplicate-averaged raw luminescence of individual ORFs against the average and standard deviation of all control-treated cells via the z-score, or standard score, below, $$Z = \frac{x - \mu}{\sigma}$$

where x=average raw luminescence of a given ORF, μ=the mean raw luminescence of all ORFs and σ=the standard deviation of the raw luminescence of all wells. Any individual ORF with a z-score>+2 or <−2 was annotated as affecting proliferation and removed from final analysis. Differential proliferation was determined by the percentage of duplicate-averaged raw luminescence values in PLX4720 (1 µM) treated cells relative to untreated cells. Subsequently, differential proliferation was normalized to the positive control for PLX4720 resistance, MEK1$^{S218/222D}$ (MEK1$^{DD}$), with MEK1$^{DD}$ differential proliferation=1.0. MEK1$^{DD}$ normalized differential proliferation for each individual ORF was averaged across two duplicate experiments, with two time points for each experiment (day 4 and day 6). A z-score was then generated, as described above for average MEK1$^{DD}$ normalized differential proliferation. ORFs with a z-score of >2 were considered hits and were followed up in the secondary screen.

ORF and shRNA Expression

ORFs were expressed from pLX-Blast-V5 (lentiviral) or pWZL-Blast, pBABE-Puro or pBABE-zeocin (retroviral) expression plasmids. For lentiviral transduction, 293T cells were transfected with 1 µg of pLX-Blast-V5-ORF or pLKO.1-shRNA, 900 ng Δ8.9 (gag, pol) and 100 ng VSV-G using 6 µl Fugene6 transfection reagent (Roche). Viral supernatant was harvested 72 h post-transfection. Mammalian cells were infected at a 1:10-1:20 dilution of virus in 6-well plates in the presence of 5 µg/ml polybrene and centrifuged at 2250 RPM for 1 h at 37° C. Twenty-four hours after infection blasticidin (pLX-Blast-V5, 10 µg/ml) or puro (pLKO.1, 0.75 µg/ml) was added and cells were selected for 48 hrs. For retrovirus production, 293T were transfected with 1 µg of retroviral plasmid-ORF, 1 µg pCL-AMPHO and 100 ng VSV-G, as described above. Cells were infected with retrovirus containing supernatant at a 1:2 dilution in 5 µg/ml polybrene overnight, followed by media change to growth medium. Infection was repeated once more (twice total), followed by selection, above.

Secondary Screen

A375 (1.5×10$^3$) and SKMEL28 cells (3×10$^3$) were seeded in 96-well plates for 18 h. ORF-expressing lentivirus was added at a 1:10 dilution in the presence of 8 µg/ml polybrene, and centrifuged at 2250 RPM and 37° C. for 1 h. Following centrifugation, virus-containing media was changed to normal growth media and allowed to incubate for 18 h. Twenty-four hours after infection, DMSO (1:1000) or 10×PLX4720 (in DMSO) was added to a final concentration of 100, 10, 1, 0.1, 0.01, 0.001, 0.0001 or 0.00001 µM. Cell viability was assayed using WST-1 (Roche), per manufacturer recommendation, 4 days after the addition of PLX4720.

Cell Lines and Reagents

A375, SKMEL28, SKMEL30, COLO-679, WM451lu, SKMEL5, Malme 3M, SKMEL30, WM3627, WM1976, WM3163, WM3130, WM3629, WM3453, WM3682 and WM3702 were all grown in RPMI (Cellgro), 10% FBS and 1% penicillin/streptomycin. M307 was grown in RPMI (Cellgro), 10% FBS and 1% penicillin/streptomycin supplemented with 1 mM sodium pyruvate. 293T and OUMS-23 were grown in DMEM (Cellgro), 10% FBS and 1% penicillin/streptomycin. RPMI-7951 cells (ATCC) were grown in MEM (Cellgro), 10% FBS and 1% penicillin/streptomycin. Wild-type primary melanocytes were grown in HAM's F10 (Cellgro), 10% FBS and 1% penicillin/streptomycin. B-RAF$^{V600E}$-expressing primary melanocytes were grown in TIVA media [Ham's F-10 (Cellgro), 7% FBS, 1% penicillin/streptomycin, 2 mM glutamine (Cellgro), 100 uM IBMX, 50 ng/ml TPA, 1 mM dbcAMP (Sigma) and 1 µM sodium vanadate]. CI-1040 (PubChem ID: 6918454) was purchased from Shanghai Lechen International Trading Co., AZD6244 (PubChem ID: 10127622) from Selleck Chemicals, and PLX4720 (PubChem ID: 24180719) from Symansis. RAF265 (PubChem ID: 11656518) was a generous gift from Novartis Pharma AG. Unless otherwise indicated, all drug treatments were for 16 h. Activated alleles of NRAS and KRAS have been previously described.

(Boehm, J. S. et al. Cell 129, 1065-1079 (2007); Lundberg, A. S. et al. Oncogene 21, 4577-4586 (2002)).

Pharmacologic Growth Inhibition Assays

Cultured cells were seeded into 96-well plates (3,000 cells per well) for all melanoma cell lines; 1,500 cells were seeded for A375. Twenty-four hours after seeding, serial dilutions of the relevant compound were prepared in DMSO added to cells, yielding final drug concentrations ranging from 100 µM to 1×105 µM, with the final volume of DMSO not exceeding 1%. Cells were incubated for 96 h following addition of drug. Cell viability was measured using the WST1 viability assay (Roche). Viability was calculated as a percentage of control (untreated cells) after background subtraction. A minimum of six replicates were performed for each cell line and drug combination. Data from growth-inhibition assays were modeled using a nonlinear regression curve fit with a sigmoid dose-response. These curves were displayed and GI50 generated using GraphPad Prism 5 for Windows (GraphPad). Sigmoid-response curves that crossed the 50% inhibition point at or above 10 µM have GI50 values annotated as >10 µM. For single-dose studies, the identical protocol was followed, using a single dose of indicated drug (1 µM unless otherwise noted).

Immunoblots and Immunoprecipitations

Cells were washed twice with ice-cold PBS and lysed with 1% NP-40 buffer [150 mM NaCl, 50 mM Tris pH 7.5, 2 mM EDTA pH 8, 25 mM NaF and 1% NP-40] containing 2× protease inhibitors (Roche) and 1× Phosphatase Inhibitor Cocktails I and II (CalBioChem). Lysates were quantified (Bradford assay), normalized, reduced, denatured (95° C.) and resolved by SDS gel electrophoresis on 10% Tris/Glycine gels (Invitrogen). Protein was transferred to PVDF membranes and probed with primary antibodies recognizing pERK1/2 (T202/Y204), pMEK1/2 (S217/221), MEK1/2, MEK1, MEK2, C-RAF (rabbit host), pC-RAF (pS338) (Cell Signaling Technology; 1:1,000), V5-HRP (Invitrogen; (1:5,000), COT (1:500), B-RAF (1:2,000), Actin (1:1,000), Actin-HRP (1:1,000; Santa Cruz)), C-RAF (mouse host; 1:1,000; BD Transduction Labs), Vinculin (Sigma; 1:20,000), AXL (1:500; R&D Systems). After incubation with the appropriate secondary antibody (anti-rabbit, anti-mouse IgG, HRP-linked; 1:1,000 dilution, Cell Signaling Technology or anti-goat IgG, HRP-linked; 1:1,000 dilution; Santa Cruz), proteins were detected using chemiluminescence (Pierce). Immunoprecipitations were performed overnight at 4° C. in 1% NP-40 lysis buffer, as described above, at a concentration of 1 µg/µl total protein using an antibody recognizing C-RAF (1:50; Cell Signaling Technology). Antibody: antigen complexes were bound to Protein A agarose (25 µL, 50% slurry; Pierce) for 2 hrs. at 4° C. Beads were centrifuged and washed three times in lysis buffer and eluted and denatured (95° C.) in 2× reduced sample buffer (Invitrogen). Immunoblots were performed as above. Phospho-protein quantification was performed using NIH Image J.

Lysates from tumor and matched normal skin were generated by mechanical homogenization of tissue in RIPA [50 mM Tris (pH 7.4), 150 mM NaCl, 1 mM EDTA, 0.1% SDS, 1.0% NaDOC, 1.0% Triton X-100, 25 mM NaF, 1 mM NA3VO4] containing protease and phosphatase inhibitors, as above. Subsequent normalization and immunoblots were performed as above.

Biopsied Melanoma Tumour Material

Biopsied tumor material consisted of discarded and de-identified tissue that was obtained with informed consent and characterized under protocol 02-017 (paired samples, Massachusetts General Hospital) and 07-087 (unpaired sample, Dana-Farber Cancer Institute). For paired specimens, 'on-treatment' samples were collected 10-14 days after initiation of PLX4032 treatment (Table 6).

Inhibition of COT Kinase Activity

Adherent RPMI-7951 cells were washed twice with 1×PBS and incubated overnight in serum-free growth media. Subsequently, 4-(3-Chloro-4-fluorophenylamino)-6-(pyridin-3-yl-methylamino)-3-cyano-[1,7]-naphthyridine (EMD; TPL2 inhibitor I; Cat #: 616373, PubChem ID: 9549300), suspended in DMSO at the indicated concentration, was added to cells for 1 hour, after which protein extracts were made as described above.

Quantitative RT-PCR mRNA was extracted from cell lines and fresh-frozen tumors using the RNeasy kit (Qiagen). Total mRNA was used for subsequent reverse transcription using the SuperScript III First-Strand Synthesis SuperMix (Invitrogen) for cell lines and unpaired tumor samples, and the SuperScript VILO cDNA synthesis kit (Invitrogen) for paired frozen tumor samples. 5 μl of the RT reaction was used for quantitative PCR using SYBR Green PCR Master Mix and gene-specific primers, in triplicate, using an ABI 7300 Real Time PCR System. Primers used for detection are as follows:

| Primer | Sequence | SEQ.ID. NO. |
|---|---|---|
| COT forward | CAAGTGAAGAGCCAGCAGTTT | SEQ. ID.NO: 1 |
| COT reverse | GCAAGCAAATCCTCCACAGTTC | SEQ. ID.NO: 2 |
| TBP forward | CCCGAAACGCCGAATATAATCC | SEQ. ID.NO: 3 |
| TBP reverse | GACTGTTCTTCACTCTTGGCTC | SEQ. ID.NO: 4 |
| GAPDH forward | CATCATCTCTGCCCCCTCT | SEQ. ID.NO: 5 |
| GAPDH reverse | GGTGCTAAGCAGTTGGTGGT | SEQ. ID.NO: 6 |

In Vitro Kinase Assay

In vitro kinase assays were performed as previously described using 1 μg each of COT (amino acids 30-397, R&D Systems) and inactive ERK1 (Millipore).

Cellular Viability Assays

Adherent RPMI-7951 cells were infected with virus expressing shRNAs against COT or Luciferase as described above. Following selection, cells were plated (1.5×10$^5$ cells/well) onto a 24-well plate in quadruplicate. Viable cells were counted via trypan blue exclusion using a VI-CELL Cell Viability Analyzer, per manufacturer's specifications. Quadruplicate cell counts were averaged and normalized relative to that of the control shRNA.

The Cancer Cell Line Encyclopedia (CCLE)

The Cancer Cell Line Encyclopedia (CCLE) project is a collaboration between the Broad Institute, the Novartis Institutes for Biomedical Research (NIBR) and the Genomics Institute of the Novartis Research Foundation (GNF) to conduct a detailed genetic and pharmacologic characterization of a large panel of human cancer models, to develop integrated computational analyses that link distinct pharmacologic vulnerabilities to genomic patterns and to translate cell line integrative genomics into cancer patient stratification. Chromosomal copy number and gene expression data used for this study are available online at http://www.broadinstitute.org/cgi-bin/cancer/datasets.cgi.

Expression Profiling of Cancer Cell Lines

Oligonucleotide microarray analysis was carried out using the GeneChip Human Genome U133 Plus 2.0 Affymetrix expression array (Affymetrix). Samples were converted to labeled, fragmented, cRNA following the Affymetrix protocol for use on the expression microarray.

shRNA Constructs Used (pLKO.1)

The DNA sequences for preparing the shRNA constructs used were as follows:

| shRNA | TRC Identifier | NM No. | Sequence | SEQ. ID. NO. |
|---|---|---|---|---|
| shLuc | TRCN0000072243 | NA | CTTCGAAATGTCCGTTCGGTT | SEQ. ID. NO. 7 |
| shBRAF(1) | TRCN0000006289 | NM_004333.2-1106s1c1 | CTTCGAAATGTCCGTTCGGTT | SEQ. ID. NO. 8 |
| shBRAF(2) | TRCN0000006291 | NM_004333.2-2267s1c1 | GCTGGTTTCCAAACAGAGGAT | SEQ. ID. NO. 9 |
| shCRAF(1) | TRCN0000001066 | NM_002880.x-1236s1c1 | CGGAGATGTTGCAGTAAAGAT | SEQ. ID. NO. 10 |
| shCRAF(2) | TRCN0000001068 | NM_02880.x-1529s1c1 | GAGACATGAAATCCAACAATA | SEQ. ID. NO. 11 |
| shMEK1(1) | TRCN0000002332 | NM_002755.x-1015s1c1 | GATTACATAGTCAACGAGCCT | SEQ. ID. NO. 12 |
| shMEK1(2) | TRCN0000002329 | NM_002755.x-455s1c1 | GCTTCTATGGTGCGTTCTACA | SEQ. ID. NO. 13 |
| shMEK2(1) | TRCN0000007007 | NM_030662.2-1219s1c1 | TGGACTATATTGTGAACGAGC | SEQ. ID. NO. 14 |

-continued

| shRNA | TRC Identifier | NM No. | Sequence | SEQ. ID. NO. |
|---|---|---|---|---|
| shMEK2(2) | TRCN 0000007005 | NM_030662.2-847s1c1 | CCAACATCCTCGTGAACTCTA | SEQ. ID. NO. 15 |
| shCOT(1) | TRCN 0000010013 | NM_005204.x-1826s1c1 | CAAGAGCCGCAGACCTACTAA | SEQ. ID. NO. 16 |
| shCOT(2) | TRCN 0000196518 | NM_005204.2-2809s1c1 | GATGAGAATGTGACCTTTAAG | SEQ. ID. NO. 17 |

The definitions and disclosures provided herein govern and supersede all others incorporated by reference. Although the invention herein has been described in connection with preferred embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

TABLE 3

CCSB/Broad Institute Kinase ORF Library description and ORF classification

| hGENE | GENE ID | DESCRIPTION | KINASE CLASS |
|---|---|---|---|
| AAK1 | 22848 | AP2 associated kinase 1 | protein kinase (NRS/TK) |
| ABL1 | 25 | v-abl Abelson murine leukemia viral oncogene homolog 1 | protein kinase (NRTK) |
| ABL2 | 27 | v-abl Abelson murine leukemia viral oncogene homolog 2 (arg, Abelson-related gene) | protein kinase (NRTK) |
| ACVR1 | 90 | activin A receptor, type I | protein kinase (RS/TK) |
| ACVR1B | 91 | activin A receptor, type IB | protein kinase (RS/TK) |
| ACVR1C | 130399 | activin A receptor, type IC | protein kinase (RS/TK) |
| ACVR2A | 92 | activin A receptor, type II | protein kinase (RS/TK) |
| ACVR2B | 93 | activin A receptor, type IIB | protein kinase (RS/TK) |
| ACVRL1 | 94 | activin A receptor type II-like 1 | protein kinase (RS/TK) |
| ADCK1 | 57143 | aarF domain containing kinase 1 | protein kinase |
| ADCK2 | 90956 | aarF domain containing kinase 2 | protein kinase |
| ADCK4 | 79934 | aarF domain containing kinase 4 | protein kinase |
| ADPGK | 83440 | ADP-dependent glucokinase | kinase related |
| ADRBK1 | 156 | adrenergic, beta, receptor kinase 1 | protein kinase (NRS/TK) |
| ADRBK2 | 157 | adrenergic, beta, receptor kinase 2 | protein kinase (NRS/TK) |
| AGK | 55750 | multiple substrate lipid kinase; MULK | kinase related |
| AK1 | 203 | adenylate kinase 1 | nucleotide kinase |
| AK2 | 204 | adenylate kinase 2 | nucleotide kinase |
| AK3 | 205 | adenylate kinase 3 | nucleotide kinase |
| AK3L1 | 50808 | adenylate kinase 3 like 1 | nucleotide kinase |
| AK7 | 122481 | adenylate kinase 7 | nucleotide kinase |
| AKT1 | 207 | v-akt murine thymoma viral oncogene homolog 1 | protein kinase (NRS/TK) |
| AKT3 | 10000 | v-akt murine thymoma viral oncogene homolog 3 (protein kinase B, gamma) | protein kinase (NRS/TK) |
| ALDH18A1 | 5832 | aldehyde dehydrogenase 18 family, member A1; ALDH18A1 | kinase related |
| ALK | 238 | anaplastic lymphoma kinase (Ki-1) | protein kinase (RTK) |
| ALPK1 | 80216 | alpha-kinase 1 | protein kinase (NRS/TK) |
| ALPK2 | 115701 | alpha-kinase 2 | protein kinase (NRS/TK) |
| ALS2CR7 | 65061 | amyotrophic lateral sclerosis 2 (juvenile) chromosome region, candidate 7 | protein kinase (NRS/TK) |
| AMHR2 | 269 | anti-Mullerian hormone receptor, type II | protein kinase (RS/TK) |
| ARAF | 369 | v-raf murine sarcoma 3611 viral oncogene homolog 1 | protein kinase (NRS/TK) |
| ARSG | 22901 | arylsulfatase G; ARSG | kinase related |
| ASCIZ | 23300 | ATM/ATR-Substrate Chk2-Interacting Zn2+-finger protein; ASCIZ | protein kinase (NRS/TK) |
| AURKA | 6790 | serine/threonine kinase 6 | protein kinase (NRS/TK) |
| AURKB | 9212 | aurora kinase B | protein kinase (NRS/TK) |
| AURKC | 6795 | aurora kinase C | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| AXL | 558 | AXL receptor tyrosine kinase | protein kinase (RTK) |
| BCKDK | 10295 | branched chain alpha-ketoacid dehydrogenase kinase | protein kinase |
| BLK | 640 | B lymphoid tyrosine kinase | protein kinase (NRTK) |
| BMP2K | 55589 | BMP2 inducible kinase | protein kinase (NRS/TK) |
| BMP2KL | 347359 | BMP2 inducible kinase-like | protein kinase (NRS/TK) |
| BMPR1A | 657 | bone morphogenetic protein receptor, type IA | protein kinase (RS/TK) |
| BMPR1B | 658 | bone morphogenetic protein receptor, type IB | protein kinase (RS/TK) |
| BMPR2 | 659 | bone morphogenetic protein receptor, type II (serine/threonine kinase) | protein kinase (RS/TK) |
| BMX | 660 | BMX non-receptor tyrosine kinase | protein kinase (NRTK) |
| BRAF | 673 | v-raf murine sarcoma viral oncogene homolog B1 | protein kinase (NRS/TK) |
| BRD3 | 8019 | bromodomain containing 3 | protein kinase (NRS/TK) |
| BRD4 | 23476 | bromodomain containing 4 | protein kinase (NRS/TK) |
| BRSK1 | 84446 | KIAA1811 protein | protein kinase (NRS/TK) |
| BRSK2 | 9024 | serine/threonine kinase 29 | protein kinase (NRS/TK) |
| BTK | 695 | Bruton agammaglobulinemia tyrosine kinase | protein kinase (NRTK) |
| BUB1 | 699 | BUB1 budding uninhibited by benzimidazoles 1 homolog (yeast) | protein kinase (NRS/TK) |
| BUB1B | 701 | BUB1 budding uninhibited by benzimidazoles 1 homolog beta (yeast) | protein kinase (NRS/TK) |
| C1orf57 | 84284 | chromosome 1 open reading frame 57; C1orf57 | kinase related |
| C9orf95 | 54981 | chromosome 9 open reading frame 95; C9orf95 | kinase related |
| C9orf98 | 158067 | chromosome 9 open reading frame 98; C9orf98 | nucleotide kinase |
| CABC1 | 56997 | chaperone, ABC1 activity of bc1 complex like (*S. pombe*) | protein kinase |
| CALM1 | 801 | calmodulin 1 (phosphorylase kinase, delta) | kinase related |
| CALM2 | 805 | calmodulin 2 (phosphorylase kinase, delta) | kinase related |
| CALM3 | 808 | calmodulin 3 (phosphorylase kinase, delta) | kinase related |
| CAMK1 | 8536 | calcium/calmodulin-dependent protein kinase I | protein kinase (NRS/TK) |
| CAMK1D | 57118 | calcium/calmodulin-dependent protein kinase ID | protein kinase (NRS/TK) |
| CAMK1G | 57172 | calcium/calmodulin-dependent protein kinase IG | protein kinase (NRS/TK) |
| CAMK2A | 815 | calcium/calmodulin-dependent protein kinase (CaM kinase) II alpha | protein kinase (NRS/TK) |
| CAMK2B | 816 | calcium/calmodulin-dependent protein kinase (CaM kinase) II beta | protein kinase (NRS/TK) |
| CAMK2D | 817 | calcium/calmodulin-dependent protein kinase (CaM kinase) II delta | protein kinase (NRS/TK) |
| CAMK2G | 818 | calcium/calmodulin-dependent protein kinase (CaM kinase) II gamma | protein kinase (NRS/TK) |
| CAMK4 | 814 | calcium/calmodulin-dependent protein kinase IV | protein kinase (NRS/TK) |
| CAMKK1 | 84254 | calcium/calmodulin-dependent protein kinase kinase 1, alpha | protein kinase (NRS/TK) |
| CAMKK2 | 10645 | calcium/calmodulin-dependent protein kinase kinase 2, beta | protein kinase (NRS/TK) |
| CAMKV | 79012 | hypothetical protein MGC8407 | protein kinase (NRS/TK) |
| CARD11 | 84433 | caspase recruitment domain family, member 11; CARD11 | nucleotide kinase |
| CARKL | 23729 | carbohydrate kinase-like | carbohydrate kinase |
| CASK | 8573 | calcium/calmodulin-dependent serine protein kinase (MAGUK family) | nucleotide kinase |
| CCL2 | 6347 | chemokine (C-C motif) ligand 2; CCL2 | protein kinase |
| CCL4 | 6351 | chemokine (C-C motif) ligand 4; CCL4 | protein kinase (RTK) |
| CCRK | 23552 | cell cycle related kinase | protein kinase (NRS/TK) |
| CD2 | 914 | CD2 antigen (p50), sheep red blood cell receptor; CD2 | protein kinase |
| CDC2 | 983 | cell division cycle 2, G1 to S and G2 to M | protein kinase (NRS/TK) |
| CDC2L1 | 984 | cell division cycle 2-like 1 (PITSLRE proteins) | protein kinase (NRS/TK) |
| CDC2L2 | 985 | cell division cycle 2-like 2 (PITSLRE proteins) | protein kinase (NRS/TK) |
| CDC2L6 | 23097 | cell division cycle 2-like 6 (CDK8-like) | protein kinase (NRS/TK) |
| CDC42BPG | 55561 | CDC42 binding protein kinase gamma (DMPK-like) | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| CDC7 | 8317 | CDC7 cell division cycle 7 (*S. cerevisiae*) | protein kinase (NRS/TK) |
| CDK10 | 8558 | cyclin-dependent kinase (CDC2-like) 10 | protein kinase (NRS/TK) |
| CDK2 | 1017 | cyclin-dependent kinase 2 | protein kinase (NRS/TK) |
| CDK3 | 1018 | cyclin-dependent kinase 3 | protein kinase (NRS/TK) |
| CDK4 | 1019 | cyclin-dependent kinase 4 | protein kinase (NRS/TK) |
| CDK5 | 1020 | cyclin-dependent kinase 5 | protein kinase (NRS/TK) |
| CDK5R1 | 8851 | cyclin-dependent kinase 5, regulatory subunit 1 (p35) | protein kinase (NRS/TK) |
| CDK6 | 1021 | cyclin-dependent kinase 6 | protein kinase (NRS/TK) |
| CDK7 | 1022 | cyclin-dependent kinase 7 (MO15 homolog, Xenopus laevis, cdk-activating kinase) | protein kinase (NRS/TK) |
| CDK8 | 1024 | cyclin-dependent kinase 8 | protein kinase (NRS/TK) |
| CDK9 | 1025 | cyclin-dependent kinase 9 (CDC2-related kinase) | protein kinase (NRS/TK) |
| CDKL1 | 8814 | cyclin-dependent kinase-like 1 (CDC2-related kinase) | protein kinase (NRS/TK) |
| CDKL2 | 8999 | cyclin-dependent kinase-like 2 (CDC2-related kinase) | protein kinase (NRS/TK) |
| CDKL3 | 51265 | cyclin-dependent kinase-like 3 | protein kinase (NRS/TK) |
| CDKL4 | 344387 | cyclin-dependent kinase-like 4 | protein kinase (NRS/TK) |
| CDKL5 | 6792 | cyclin-dependent kinase-like 5 | protein kinase (NRS/TK) |
| CHEK1 | 1111 | CHK1 checkpoint homolog (*S. pombe*) | protein kinase (NRS/TK) |
| CHEK2 | 11200 | CHK2 checkpoint homolog (*S. pombe*) | protein kinase (NRS/TK) |
| CHKA | 1119 | choline kinase alpha | kinase related |
| CIB1 | 10519 | calcium and integrin binding 1 (calmyrin); CIB1 | kinase related |
| CIB4 | 130106 | calcium and integrin binding family member 4; CIB4 | kinase related |
| CKB | 1152 | creatine kinase, brain | kinase related |
| CKM | 1158 | creatine kinase, muscle | kinase related |
| CKMT1A | 548596 | creatine kinase, mitochondrial 1A; CKMT1A | kinase related |
| CKMT2 | 1160 | creatine kinase, mitochondrial 2 (sarcomeric) | kinase related |
| CKS1B | 1163 | CDC28 protein kinase regulatory subunit 1B | protein kinase |
| CKS2 | 1164 | CDC28 protein kinase regulatory subunit 2 | protein kinase |
| CLK1 | 1195 | CDC-like kinase 1 | protein kinase (NRS/TK) |
| CLK2 | 1196 | CDC-like kinase 2 | protein kinase (NRS/TK) |
| CLK3 | 1198 | CDC-like kinase 3 | protein kinase (NRS/TK) |
| COASY | 80347 | Coenzyme A synthase; COASY | kinase related |
| COL4A3BP | 10087 | collagen, type IV, alpha 3 (Goodpasture antigen) binding protein; COL4A3BP | protein kinase |
| CRKL | 1399 | v-crk sarcoma virus CT10 oncogene homolog (avian)-like; CRKL | kinase related |
| CSF1R | 1436 | colony stimulating factor 1 receptor, formerly McDonough feline sarcoma viral (v-fms) oncogene homolog | protein kinase (RTK) |
| CSK | 1445 | c-src tyrosine kinase | protein kinase (NRTK) |
| CSNK1A1 | 1452 | casein kinase 1, alpha 1 | protein kinase (NRS/TK) |
| CSNK1A1L | 122011 | casein kinase 1, alpha 1-like | protein kinase (NRS/TK) |
| CSNK1D | 1453 | casein kinase 1, delta | protein kinase (NRS/TK) |
| CSNK1E | 1454 | casein kinase 1, epsilon | protein kinase (NRS/TK) |
| CSNK1G1 | 53944 | casein kinase 1, gamma 1 | protein kinase (NRS/TK) |
| CSNK1G2 | 1455 | casein kinase 1, gamma 2 | protein kinase (NRS/TK) |
| CSNK1G3 | 1456 | casein kinase 1, gamma 3 | protein kinase (NRS/TK) |
| CSNK2A1 | 1457 | casein kinase 2, alpha 1 polypeptide | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| CSNK2B | 1460 | casein kinase 2, beta polypeptide | protein kinase (NRS/TK) |
| DAK | 26007 | dihydroxyacetone kinase 2 homolog (*S. cerevisiae*); DAK | kinase related |
| DAPK1 | 1612 | death-associated protein kinase 1 | protein kinase (NRS/TK) |
| DAPK2 | 23604 | death-associated protein kinase 2 | protein kinase (NRS/TK) |
| DAPK3 | 1613 | death-associated protein kinase 3 | protein kinase (NRS/TK) |
| DCAKD | 79877 | dephospho-CoA kinase domain containing; DCAKD | kinase related |
| DCAMKL2 | 166614 | hypothetical protein MGC45428 | protein kinase (NRS/TK) |
| DCK | 1633 | deoxycytidine kinase | nucleotide kinase |
| DDR1 | 780 | discoidin domain receptor family, member 1 | protein kinase (RTK) |
| DDR2 | 4921 | discoidin domain receptor family, member 2 | protein kinase (RTK) |
| DGKA | 1606 | diacylglycerol kinase, alpha 80 kDa | kinase related |
| DGKB | 1607 | diacylglycerol kinase, beta 90 kDa | kinase related |
| DGKG | 1608 | diacylglycerol kinase, gamma 90 kDa | kinase related |
| DGKK | 139189 | diacylglycerol kinase, kappa; DGKK | kinase related |
| DGKZ | 8525 | diacylglycerol kinase, zeta 104 kDa | kinase related |
| DGUOK | 1716 | deoxyguanosine kinase | nucleotide kinase |
| DKFZp434B1231 | 91156 | eEF1A2 binding protein; DKFZp434B1231 | protein kinase (NRS/TK) |
| DKFZp761P0423 | 157285 | hypothetical protein DKFZp761P0423 | protein kinase (RS/TK) |
| DLG1 | 1739 | discs, large homolog 1 (*Drosophila*); DLG1 | nucleotide kinase |
| DLG3 | 1741 | discs, large homolog 3 (neuroendocrine-dlg, *Drosophila*); DLG3 | nucleotide kinase |
| DTYMK | 1841 | deoxythymidylate kinase (thymidylate kinase) | nucleotide kinase |
| DYRK1A | 1859 | dual-specificity tyrosine-(Y)-phosphorylation regulated kinase 1A | protein kinase (NRS/TK) |
| DYRK1B | 9149 | dual-specificity tyrosine-(Y)-phosphorylation regulated kinase 1B | protein kinase (NRS/TK) |
| DYRK2 | 8445 | dual-specificity tyrosine-(Y)-phosphorylation regulated kinase 2 | protein kinase (NRS/TK) |
| DYRK3 | 8444 | dual-specificity tyrosine-(Y)-phosphorylation regulated kinase 3 | protein kinase (NRS/TK) |
| DYRK4 | 8798 | dual-specificity tyrosine-(Y)-phosphorylation regulated kinase 4 | protein kinase (NRS/TK) |
| EEF2K | 29904 | eukaryotic elongation factor-2 kinase | protein kinase (NRS/TK) |
| EGFR | 1956 | epidermal growth factor receptor (erythroblastic leukemia viral (v-erb-b) oncogene homolog, avian) | protein kinase (RTK) |
| EIF2AK1 | 27102 | heme-regulated initiation factor 2-alpha kinase | protein kinase (NRS/TK) |
| EIF2AK4 | 415116 | serine/threonine-protein kinase pim-3 | protein kinase (RS/TK) |
| EPHA1 | 2041 | EPH receptor A1 | protein kinase (RTK) |
| EPHA2 | 1969 | EPH receptor A2 | protein kinase (RTK) |
| EPHA3 | 2042 | EPH receptor A3 | protein kinase (RTK) |
| EPHA4 | 2043 | EPH receptor A4 | protein kinase (RTK) |
| EPHA6 | 285220 | EPH receptor A6 | protein kinase (RTK) |
| EPHB1 | 2047 | EPH receptor B1 | protein kinase (RTK) |
| EPHB4 | 2050 | EPH receptor B4 | protein kinase (RTK) |
| EPHB6 | 2051 | EPH receptor B6 | protein kinase (RTK) |
| ERBB2 | 2064 | v-erb-b2 erythroblastic leukemia viral oncogene homolog 2, neuro/glioblastoma derived oncogene homolog (avian) | protein kinase (RTK) |
| ERBB3 | 2065 | v-erb-b2 erythroblastic leukemia viral oncogene homolog 3 (avian) | protein kinase (RTK) |
| ERBB4 | 2066 | v-erb-a erythroblastic leukemia viral oncogene homolog 4 (avian) | protein kinase (RTK) |
| ERN1 | 2081 | endoplasmic reticulum to nucleus signalling 1 | protein kinase |
| ETNK1 | 55500 | ethanolamine kinase 1 | kinase related |
| ETNK2 | 55224 | ethanolamine kinase 2 | kinase related |
| EXOSC10 | 5394 | exosome component 10; EXOSC10 | protein kinase (NRS/TK) |
| FASTK | 10922 | FAST kinase | protein kinase (NRS/TK) |
| FASTKD1 | 79675 | FAST kinase domains 1; FASTKD1 | protein kinase |
| FASTKD2 | 22868 | FAST kinase domains 2; FASTKD2 | protein kinase |
| FASTKD3 | 79072 | FAST kinase domains 3; FASTKD3 | protein kinase |
| FASTKD5 | 60493 | FAST kinase domains 5; FASTKD5 | protein kinase |
| FER | 2241 | fer (fps/fes related) tyrosine kinase (phosphoprotein NCP94) | protein kinase (NRTK) |
| FES | 2242 | feline sarcoma oncogene | protein kinase (NRTK) |
| FGFR1 | 2260 | fibroblast growth factor receptor 1 (fms-related tyrosine kinase 2, Pfeiffer syndrome) | protein kinase (RTK) |
| FGFR2 | 2263 | fibroblast growth factor receptor 2 (craniofacial dysostosis 1, Crouzon, Pfeiffer and Jackson-Weiss syndrome) | protein kinase (RTK) |

TABLE 3-continued

CCSB/Broad Institute Kinase ORF Library description and ORF classification

| hGENE | GENE ID | DESCRIPTION | KINASE CLASS |
|---|---|---|---|
| FGFR3 | 2261 | fibroblast growth factor receptor 3 (achondroplasia, thanatophoric dwarfism) | protein kinase (RTK) |
| FGFRL1 | 53834 | fibroblast growth factor receptor-like 1; FGFRL1 | protein kinase (RTK) |
| FGR | 2268 | Gardner-Rasheed feline sarcoma viral (v-fgr) oncogene homolog | protein kinase (NRTK) |
| FLJ10986 | 55277 | hypothetical protein FLJ10986; FLJ10986 | carbohydrate kinase |
| FLJ23356 | 84197 | hypothetical protein FLJ23356 | protein kinase |
| FLJ25006 | 124923 | hypothetical protein FLJ25006 | protein kinase (NRS/TK) |
| FLJ40852 | 285962 | hypothetical protein FLJ40852 | protein kinase |
| FLT1 | 2321 | fms-related tyrosine kinase 1 (vascular endothelial growth factor/vascular permeability factor receptor) | protein kinase (RTK) |
| FLT3 | 2322 | fms-related tyrosine kinase 3 | protein kinase (RTK) |
| FLT4 | 2324 | fms-related tyrosine kinase 4 | protein kinase (RTK) |
| FN3K | 64122 | fructosamine 3 kinase | kinase related |
| FN3KRP | 79672 | fructosamine-3-kinase-related protein | kinase related |
| FRK | 2444 | fyn-related kinase | protein kinase (NRTK) |
| FUK | 197258 | fucokinase | kinase related |
| FXN | 2395 | frataxin; FXN | kinase related |
| FYN | 2534 | FYN oncogene related to SRC, FGR, YES | protein kinase (NRTK) |
| GALK1 | 2584 | galactokinase 1 | carbohydrate kinase |
| GALK2 | 2585 | galactokinase 2 | carbohydrate kinase |
| GCK | 2645 | glucokinase (hexokinase 4, maturity onset diabetes of the young 2) | carbohydrate kinase |
| GK | 2710 | glycerol kinase | carbohydrate kinase |
| GK2 | 2712 | glycerol kinase 2 | carbohydrate kinase |
| GK5 | 256356 | hypothetical protein MGC40579; MGC40579 | carbohydrate kinase |
| GLYCTK | 132158 | glycerate kinase | carbohydrate kinase |
| GNE | 10020 | glucosamine (UDP-N-acetyl)-2-epimerase/N-acetylmannosamine kinase | carbohydrate kinase |
| GRK6 | 2870 | G protein-coupled receptor kinase 6 | protein kinase (NRS/TK) |
| GRK7 | 131890 | G protein-coupled receptor kinase 7 | protein kinase (NRS/TK) |
| GSG2 | 83903 | haspin | protein kinase (RS/TK) |
| GSK3A | 2931 | glycogen synthase kinase 3 alpha | protein kinase (NRS/TK) |
| GTF2H1 | 2965 | general transcription factor IIH, polypeptide 1, 62 kDa; GTF2H1 | protein kinase (NRS/TK) |
| GUK1 | 2987 | guanylate kinase 1 | nucleotide kinase |
| HCK | 3055 | hemopoietic cell kinase | protein kinase (NRTK) |
| HIPK1 | 204851 | homeodomain interacting protein kinase 1 | protein kinase (NRS/TK) |
| HIPK2 | 28996 | homeodomain interacting protein kinase 2 | protein kinase (NRS/TK) |
| HIPK3 | 10114 | homeodomain interacting protein kinase 3 | protein kinase (NRS/TK) |
| HIPK4 | 147746 | homeodomain interacting protein kinase 4 | protein kinase (NRS/TK) |
| HK1 | 3098 | hexokinase 1 | carbohydrate kinase |
| HK2 | 3099 | hexokinase 2 | carbohydrate kinase |
| HK3 | 3101 | hexokinase 3 (white cell) | carbohydrate kinase |
| HKDC1 | 80201 | hexokinase domain containing 1; HKDC1 | carbohydrate kinase |
| HSPB8 | 26353 | heat shock 22 kDa protein 8 | protein kinase (NRS/TK) |
| IGF1R | 3480 | insulin-like growth factor 1 receptor | protein kinase (RTK) |
| IHPK1 | 9807 | inositol hexaphosphate kinase 1 | kinase related |
| IHPK2 | 51447 | inositol hexaphosphate kinase 2 | Lipid Kinase |
| IHPK3 | 117283 | inositol hexaphosphate kinase 3 | Lipid Kinase |
| IKBKE | 9641 | inhibitor of kappa light polypeptide gene enhancer in B-cells, kinase epsilon | protein kinase (NRS/TK) |
| ILK | 3611 | integrin-linked kinase | protein kinase (NRS/TK) |
| INSRR | 3645 | insulin receptor-related receptor | protein kinase (RTK) |
| IPMK | 253430 | inositol polyphosphate multikinase | Lipid Kinase |
| IPPK | 64768 | inositol 1,3,4,5,6-pentakisphosphate 2-kinase; IPPK | Lipid Kinase |
| IRAK2 | 3656 | interleukin-1 receptor-associated kinase 2 | protein kinase (RS/TK) |
| IRAK3 | 11213 | interleukin-1 receptor-associated kinase 3 | protein kinase (RS/TK) |
| IRAK4 | 51135 | interleukin-1 receptor-associated kinase 4 | protein kinase (RS/TK) |
| ITGB1BP3 | 27231 | integrin beta 1 binding protein 3; ITGB1BP3 | kinase related |
| ITK | 3702 | IL2-inducible T-cell kinase | protein kinase (NRTK) |
| ITPKB | 3707 | inositol 1,4,5-trisphosphate 3-kinase B | kinase related |
| JAK1 | 3716 | Janus kinase 1 (a protein tyrosine kinase) | protein kinase (NRTK) |
| JAK2 | 3717 | Janus kinase 2 (a protein tyrosine kinase) | protein kinase (NRTK) |
| JAK3 | 3718 | Janus kinase 3 (a protein tyrosine kinase, leukocyte) | protein kinase (NRTK) |
| KDR | 3791 | kinase insert domain receptor (a type III receptor tyrosine kinase) | protein kinase (RTK) |

TABLE 3-continued

CCSB/Broad Institute Kinase ORF Library description and ORF classification

| hGENE | GENE ID | DESCRIPTION | KINASE CLASS |
|---|---|---|---|
| KHK | 3795 | ketohexokinase (fructokinase) | carbohydrate kinase |
| KIAA0999 | 23387 | KIAA0999 protein | protein kinase (RS/TK) |
| KIAA2002 | 79834 | KIAA2002 protein | protein kinase (RS/TK) |
| KSR | 8844 | kinase suppressor of ras | protein kinase (NRS/TK) |
| KSR2 | 283455 | kinase suppressor of Ras-2 | protein kinase (NRS/TK) |
| LATS1 | 9113 | LATS, large tumor suppressor, homolog 1 (*Drosophila*) | protein kinase (NRS/TK) |
| LATS2 | 26524 | LATS, large tumor suppressor, homolog 2 (*Drosophila*) | protein kinase (NRS/TK) |
| LCK | 3932 | lymphocyte-specific protein tyrosine kinase | protein kinase (NRTK) |
| LIMK1 | 3984 | LIM domain kinase 1 | protein kinase (NRS/TK) |
| LIMK2 | 3985 | LIM domain kinase 2 | protein kinase (NRS/TK) |
| LMTK2 | 22853 | lemur tyrosine kinase 2 | protein kinase (RTK) |
| LOC220686 | 220686 | hypothetical protein LOC220686; LOC220686 | kinase related |
| LOC340156 | 340156 | hypothetical protein LOC340156 | protein kinase (NRS/TK) |
| LOC340371 | 340371 | hypothetical protein LOC340371 | protein kinase (NRS/TK) |
| LOC375133 | 375133 | similar to phosphatidylinositol 4-kinase alpha | Lipid Kinase |
| LOC388957 | 388957 | similar to BMP2 inducible kinase | protein kinase (NRS/TK) |
| LOC389599 | 389599 | similar to amyotrophic lateral sclerosis 2 (juvenile) chr. region, candidate 2; ILP-interacting protein ILPIPA | protein kinase |
| LOC390877 | 390877 | similar to adenylate kinase (EC 2.7.4.3), cytosolic - common carp | nucleotide kinase |
| LOC442075 | 442075 | similar to serine/threonine kinase, establishes embryonic polarity | protein kinase (NRS/TK) |
| LOC54103 | 54103 | hypothetical protein LOC54103; LOC54103 | protein kinase (RTK) |
| LOC646505 | 646505 | similar to Dual specificity protein kinase CLK3 (CDC-like kinase 3); unassigned | protein kinase (NRS/TK) |
| LOC647279 | 647279 | similar to MAP/microtubule affinity-regulating kinase 3; unassigned | protein kinase (NRS/TK) |
| LOC648152 | 648152 | similar to ataxia telangiectasia and Rad3 related protein; unassigned | protein kinase (NRS/TK) |
| LOC649288 | 649288 | similar to Adenylate kinase isoenzyme 4, mitochondrial (Adenylate kinase 3-like 1) | nucleotide kinase |
| LOC650122 | 650122 | similar to choline kinase alpha isoform a; unassigned | kinase related |
| LOC652722 | 652722 | similar to PTK2 protein tyrosine kinase 2 isoform a; unassigned | protein kinase (NRTK) |
| LOC652799 | 652799 | similar to Mast/stem cell growth factor receptor precursor (SCFR) (c-kit) (CD117 antigen); unassigned | protein kinase (RTK) |
| LOC653052 | 653052 | similar to Homeodomain-interacting protein kinase 2 (hHIPk2); unassigned | protein kinase (NRS/TK) |
| LOC653155 | 653155 | similar to PRP4 pre-mRNA processing factor 4 homolog B; unassigned | protein kinase (NRS/TK) |
| LOC727761 | 727761 | similar to deoxythymidylate kinase (thymidylate kinase); unassigned | nucleotide kinase |
| LOC730000 | 730000 | similar to testis-specific serine kinase 6; unassigned | protein kinase (NRS/TK) |
| LOC732306 | 732306 | similar to vaccinia related kinase 2; unassigned | protein kinase (NRS/TK) |
| LOC91461 | 91461 | hypothetical protein BC007901 | protein kinase (NRTK) |
| LOC91807 | 91807 | myosin light chain kinase (MLCK) | protein kinase (NRS/TK) |
| LRGUK | 136332 | leucine-rich repeats and guanylate kinase domain containing; LRGUK | nucleotide kinase |
| LRPPRC | 10128 | leucine-rich PPR-motif containing; LRPPRC | protein kinase (RS/TK) |
| LRRK2 | 120892 | leucine-rich repeat kinase 2 | protein kinase (NRS/TK) |
| LYK5 | 92335 | protein kinase LYK5 | protein kinase |
| LYN | 4067 | v-yes-1 Yamaguchi sarcoma viral related oncogene homolog | protein kinase (NRTK) |
| MAGI1 | 9223 | membrane associated guanylate kinase, WW and PDZ domain containing 1; MAGI1 | nucleotide kinase |
| MAK | 4117 | male germ cell-associated kinase | protein kinase (NRS/TK) |
| MAP2K1 | 5604 | mitogen-activated protein kinase kinase 1 | protein kinase |
| MAP2K1IP1 | 8649 | mitogen-activated protein kinase kinase 1 interacting protein 1 | protein kinase |
| MAP2K2 | 5605 | mitogen-activated protein kinase kinase 2 | protein kinase |
| MAP2K5 | 5607 | mitogen-activated protein kinase kinase 5 | protein kinase |
| MAP2K6 | 5608 | mitogen-activated protein kinase kinase 6 | protein kinase |
| MAP2K7 | 5609 | mitogen-activated protein kinase kinase 7 | protein kinase |
| MAP3K11 | 4296 | mitogen-activated protein kinase kinase kinase 11 | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| MAP3K12 | 7786 | mitogen-activated protein kinase kinase kinase 12 | protein kinase (NRS/TK) |
| MAP3K14 | 9020 | mitogen-activated protein kinase kinase kinase 14 | protein kinase |
| MAP3K15 | 389840 | FLJ16518 protein | protein kinase |
| MAP3K2 | 10746 | mitogen-activated protein kinase kinase kinase 2 | protein kinase |
| MAP3K5 | 4217 | mitogen-activated protein kinase kinase kinase 5 | protein kinase |
| MAP3K6 | 9064 | mitogen-activated protein kinase kinase kinase 6 | protein kinase |
| MAP3K7 | 6885 | mitogen-activated protein kinase kinase kinase 7 | protein kinase (NRS/TK) |
| MAP3K8 | 1326 | mitogen-activated protein kinase kinase kinase 8 | protein kinase |
| MAP4K1 | 11184 | mitogen-activated protein kinase kinase kinase kinase 1 | protein kinase |
| MAP4K2 | 5871 | mitogen-activated protein kinase kinase kinase kinase 2 | protein kinase |
| MAP4K3 | 8491 | mitogen-activated protein kinase kinase kinase kinase 3 | protein kinase |
| MAP4K4 | 9448 | mitogen-activated protein kinase kinase kinase kinase 4 | protein kinase |
| MAP4K5 | 11183 | mitogen-activated protein kinase kinase kinase kinase 5 | protein kinase |
| MAPK1 | 5594 | mitogen-activated protein kinase 1 | protein kinase (NRS/TK) |
| MAPK10 | 5602 | mitogen-activated protein kinase 10 | protein kinase (NRS/TK) |
| MAPK12 | 6300 | mitogen-activated protein kinase 12 | protein kinase (NRS/TK) |
| MAPK13 | 5603 | mitogen-activated protein kinase 13 | protein kinase (NRS/TK) |
| MAPK14 | 1432 | mitogen-activated protein kinase 14 | protein kinase (NRS/TK) |
| MAPK15 | 225689 | extracellular signal-regulated kinase 8 | protein kinase (NRS/TK) |
| MAPK3 | 5595 | mitogen-activated protein kinase 3 | protein kinase (NRS/TK) |
| MAPK4 | 5596 | mitogen-activated protein kinase 4 | protein kinase (NRS/TK) |
| MAPK6 | 5597 | mitogen-activated protein kinase 6 | protein kinase (NRS/TK) |
| MAPK8 | 5599 | mitogen-activated protein kinase 8 | protein kinase (NRS/TK) |
| MAPK9 | 5601 | mitogen-activated protein kinase 9 | protein kinase (NRS/TK) |
| MAPKAPK2 | 9261 | mitogen-activated protein kinase-activated protein kinase 2 | protein kinase (NRS/TK) |
| MAPKAPK3 | 7867 | mitogen-activated protein kinase-activated protein kinase 3 | protein kinase (NRS/TK) |
| MAPKAPK5 | 8550 | mitogen-activated protein kinase-activated protein kinase 5 | protein kinase (NRS/TK) |
| MARK2 | 2011 | MAP/microtubule affinity-regulating kinase 2 | protein kinase (NRS/TK) |
| MARK3 | 4140 | MAP/microtubule affinity-regulating kinase 3 | protein kinase (NRS/TK) |
| MAST1 | 22983 | microtubule associated serine/threonine kinase 1 | protein kinase (NRS/TK) |
| MAST2 | 23139 | microtubule associated serine/threonine kinase 2 | protein kinase (NRS/TK) |
| MASTL | 84930 | microtubule associated serine/threonine kinase-like | protein kinase (NRS/TK) |
| MATK | 4145 | megakaryocyte-associated tyrosine kinase | protein kinase (NRTK) |
| MERTK | 10461 | c-mer proto-oncogene tyrosine kinase | protein kinase (RTK) |
| MET | 4233 | met proto-oncogene (hepatocyte growth factor receptor) | protein kinase (RTK) |
| MGC16169 | 93627 | hypothetical protein MGC16169 | protein kinase |
| MGC42105 | 167359 | hypothetical protein MGC42105 | protein kinase (NRS/TK) |
| MINK1 | 50488 | misshapen/NIK-related kinase | protein kinase |
| MKNK1 | 8569 | MAP kinase interacting serine/threonine kinase 1 | protein kinase (NRS/TK) |
| MKNK2 | 2872 | MAP kinase interacting serine/threonine kinase 2 | protein kinase (NRS/TK) |
| MORN2 | 378464 | MORN repeat containing 2; MORN2 | kinase related |
| MOS | 4342 | v-mos Moloney murine sarcoma viral oncogene homolog | protein kinase (NRS/TK) |
| MPP1 | 4354 | membrane protein, palmitoylated 1, 55 kDa; MPP1 | protein kinase |
| MPP2 | 4355 | membrane protein, palmitoylated 2 (MAGUK p55 subfamily member 2); MPP2 | nucleotide kinase |
| MPP3 | 4356 | membrane protein, palmitoylated 3 (MAGUK p55 subfamily member 3); MPP3 | nucleotide kinase |
| MPP4 | 58538 | membrane protein, palmitoylated 4 (MAGUK p55 subfamily member 4); MPP4 | nucleotide kinase |

TABLE 3-continued

CCSB/Broad Institute Kinase ORF Library description and ORF classification

| hGENE | GENE ID | DESCRIPTION | KINASE CLASS |
|---|---|---|---|
| MPP5 | 64398 | membrane protein, palmitoylated 5 (MAGUK p55 subfamily member 5); MPP5 | nucleotide kinase |
| MPP6 | 51678 | membrane protein, palmitoylated 6 (MAGUK p55 subfamily member 6); MPP6 | nucleotide kinase |
| MPP7 | 143098 | membrane protein, palmitoylated 7 (MAGUK p55 subfamily member 7); MPP7 | nucleotide kinase |
| MST1R | 4486 | macrophage stimulating 1 receptor (c-met-related tyrosine kinase) | protein kinase (RTK) |
| MUSK | 4593 | muscle, skeletal, receptor tyrosine kinase | protein kinase (RTK) |
| MVK | 4598 | mevalonate kinase (mevalonic aciduria) | kinase related |
| MYLK2 | 85366 | myosin light chain kinase 2, skeletal muscle | protein kinase (NRS/TK) |
| MYO3B | 140469 | myosin IIIB | protein kinase (NRS/TK) |
| NADK | 65220 | NAD kinase | kinase related |
| NAGK | 55577 | N-acetylglucosamine kinase | kinase related |
| NEK10 | 152110 | NIMA (never in mitosis gene a)-related kinase 10 | protein kinase |
| NEK11 | 79858 | NIMA (never in mitosis gene a)-related kinase 11 | protein kinase |
| NEK2 | 4751 | NIMA (never in mitosis gene a)-related kinase 2 | protein kinase |
| NEK3 | 4752 | NIMA (never in mitosis gene a)-related kinase 3 | protein kinase |
| NEK4 | 6787 | NIMA (never in mitosis gene a)-related kinase 4 | protein kinase |
| NEK5 | 341676 | NIMA (never in mitosis gene a)-related kinase 5 | protein kinase |
| NEK6 | 10783 | NIMA (never in mitosis gene a)-related kinase 6 | protein kinase |
| NEK7 | 140609 | NIMA (never in mitosis gene a)-related kinase 7 | protein kinase |
| NEK8 | 284086 | NIMA (never in mitosis gene a)-related kinase 8 | protein kinase |
| NEK9 | 91754 | NIMA (never in mitosis gene a)-related kinase 9 | protein kinase |
| NJMU-R1 | 64149 | protein kinase Njmu-R1 | protein kinase |
| NLK | 51701 | nemo like kinase | protein kinase (NRS/TK) |
| NME1 | 4830 | nucleoside-diphosphate kinase 1 | nucleotide kinase |
| NME1-NME2 | 654364 | NME1-NME2 protein; NME1-NME2 | nucleotide kinase |
| NME2 | 4831 | nucleoside-diphosphate kinase 2 | nucleotide kinase |
| NME3 | 4832 | nucleoside-diphosphate kinase 3 | nucleotide kinase |
| NME4 | 4833 | nucleoside-diphosphate kinase 4 | nucleotide kinase |
| NME5 | 8382 | non-metastatic cells 5, protein expressed in (nucleoside-diphosphate kinase) | nucleotide kinase |
| NME6 | 10201 | non-metastatic cells 6, protein expressed in (nucleoside-diphosphate kinase) | nucleotide kinase |
| NME7 | 29922 | non-metastatic cells 7, protein expressed in (nucleoside-diphosphate kinase) | nucleotide kinase |
| NPR2 | 4882 | natriuretic peptide receptor B/guanylate cyclase B (atrionatriuretic peptide receptor B) | protein kinase |
| NRBP | 29959 | nuclear receptor binding protein | protein kinase (NRS/TK) |
| NTRK1 | 4914 | neurotrophic tyrosine kinase, receptor, type 1 | protein kinase (RTK) |
| NTRK2 | 4915 | neurotrophic tyrosine kinase, receptor, type 2 | protein kinase (RTK) |
| NTRK3 | 4916 | neurotrophic tyrosine kinase, receptor, type 3 | protein kinase (RTK) |
| NUAK2 | 81788 | likely ortholog of rat SNF1/AMP-activated protein kinase | protein kinase (NRS/TK) |
| NUP62 | 23636 | nucleoporin 62 kDa; NUP62 | protein kinase (NRS/TK) |
| NYD-SP25 | 89882 | protein kinase NYD-SP25 | protein kinase |
| OXSR1 | 9943 | oxidative-stress responsive 1 | protein kinase |
| PAK1 | 5058 | p21/Cdc42/Rac1-activated kinase 1 (STE20 homolog, yeast) | protein kinase |
| PAK2 | 5062 | p21 (CDKN1A)-activated kinase 2 | protein kinase |
| PAK3 | 5063 | p21 (CDKN1A)-activated kinase 3 | protein kinase |
| PAK4 | 10298 | p21(CDKN1A)-activated kinase 4 | protein kinase |
| PAK6 | 56924 | p21(CDKN1A)-activated kinase 6 | protein kinase |
| PAK7 | 57144 | p21(CDKN1A)-activated kinase 7 | protein kinase |
| PANK2 | 80025 | pantothenate kinase 2 (Hallervorden-Spatz syndrome) | kinase related |
| PANK3 | 79646 | pantothenate kinase 3 | kinase related |
| PANK4 | 55229 | pantothenate kinase 4 | kinase related |
| PAPSS1 | 9061 | 3'-phosphoadenosine 5'-phosphosulfate synthase 1; PAPSS1 | kinase related |
| PAPSS2 | 9060 | 3'-phosphoadenosine 5'-phosphosulfate synthase 2; PAPSS2 | kinase related |
| PBK | 55872 | T-LAK cell-originated protein kinase | protein kinase |
| PCK2 | 5106 | phosphoenolpyruvate carboxykinase 2 (mitochondrial) | kinase related |
| PCTK1 | 5127 | PCTAIRE protein kinase 1 | protein kinase (NRS/TK) |
| PCTK2 | 5128 | PCTAIRE protein kinase 2 | protein kinase (NRS/TK) |
| PCTK3 | 5129 | PCTAIRE protein kinase 3 | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| PDGFRA | 5156 | platelet-derived growth factor receptor, alpha polypeptide | protein kinase (RTK) |
| PDGFRB | 5159 | platelet-derived growth factor receptor, beta polypeptide | protein kinase (RTK) |
| PDGFRL | 5157 | platelet-derived growth factor receptor-like; PDGFRL | protein kinase (RTK) |
| PDIK1L | 149420 | PDLIM1 interacting kinase 1 like | protein kinase (NRS/TK) |
| PDK1 | 5163 | pyruvate dehydrogenase kinase, isoenzyme 1 | protein kinase |
| PDK2 | 5164 | pyruvate dehydrogenase kinase, isoenzyme 2 | protein kinase |
| PDK3 | 5165 | pyruvate dehydrogenase kinase, isoenzyme 3 | protein kinase |
| PDK4 | 5166 | pyruvate dehydrogenase kinase, isoenzyme 4 | protein kinase |
| PDPK1 | 5170 | 3-phosphoinositide dependent protein kinase-1 | protein kinase |
| PDXK | 8566 | pyridoxal (pyridoxine, vitamin B6) kinase | kinase related |
| PFKFB1 | 5207 | 6-phosphofructo-2-kinase/fructose-2,6-biphosphatase 1 | carbohydrate kinase |
| PFKFB2 | 5208 | 6-phosphofructo-2-kinase/fructose-2,6-biphosphatase 2 | carbohydrate kinase |
| PFKFB3 | 5209 | 6-phosphofructo-2-kinase/fructose-2,6-biphosphatase 3 | carbohydrate kinase |
| PFKL | 5211 | phosphofructokinase, liver | carbohydrate kinase |
| PFKM | 5213 | phosphofructokinase, muscle | carbohydrate kinase |
| PFKP | 5214 | phosphofructokinase, platelet | carbohydrate kinase |
| PFTK1 | 5218 | PFTAIRE protein kinase 1 | protein kinase (NRS/TK) |
| PGK1 | 5230 | phosphoglycerate kinase 1 | carbohydrate kinase |
| PGK2 | 5232 | phosphoglycerate kinase 2 | carbohydrate kinase |
| PHKA1 | 5255 | phosphorylase kinase, alpha 1 (muscle) | protein kinase (NRS/TK) |
| PHKA2 | 5256 | phosphorylase kinase, alpha 2 (liver) | protein kinase (NRS/TK) |
| PHKB | 5257 | phosphorylase kinase, beta | protein kinase (NRS/TK) |
| PHKG1 | 5260 | phosphorylase kinase, gamma 1 (muscle) | protein kinase (NRS/TK) |
| PHKG2 | 5261 | phosphorylase kinase, gamma 2 (testis) | protein kinase (NRS/TK) |
| PI4K2B | 55300 | phosphatidylinositol 4-kinase type-II beta | Lipid Kinase |
| PI4KII | 55361 | phosphatidylinositol 4-kinase type II | Lipid Kinase |
| PIK3C2G | 5288 | phosphoinositide-3-kinase, class 2, gamma polypeptide | Lipid Kinase |
| PIK3C3 | 5289 | phosphoinositide-3-kinase, class 3 | Lipid Kinase |
| PIK3CA | 5290 | phosphoinositide-3-kinase, catalytic, alpha polypeptide | Lipid Kinase |
| PIK3CBP | 5291 | phosphoinositide-3-kinase, catalytic, beta polypeptide | Lipid Kinase |
| PIK3CG | 5294 | phosphoinositide-3-kinase, catalytic, gamma polypeptide | Lipid Kinase |
| PIK3R1 | 5295 | phosphoinositide-3-kinase, regulatory subunit 1 (p85 alpha) | Lipid Kinase |
| PIK3R3 | 8503 | phosphoinositide-3-kinase, regulatory subunit 3 (p55, gamma) | Lipid Kinase |
| PIK3R4 | 30849 | phosphoinositide-3-kinase, regulatory subunit 4, p150 | Lipid Kinase |
| PIK3R5 | 23533 | phosphoinositide-3-kinase, regulatory subunit 5, p101 | Lipid Kinase |
| PIK4CA | 5297 | phosphatidylinositol 4-kinase, catalytic, alpha polypeptide | Lipid Kinase |
| PIK4CB | 5298 | phosphatidylinositol 4-kinase, catalytic, beta polypeptide | Lipid Kinase |
| PIM1 | 5292 | pim-1 oncogene | protein kinase (RS/TK) |
| PIM2 | 11040 | pim-2 oncogene | protein kinase (RS/TK) |
| PINK1 | 65018 | PTEN induced putative kinase 1 | protein kinase (RS/TK) |
| PIP5K1A | 8394 | phosphatidylinositol-4-phosphate 5-kinase, type I, alpha | Lipid Kinase |
| PIP5K1B | 8395 | phosphatidylinositol-4-phosphate 5-kinase, type I, beta | Lipid Kinase |
| PIP5K2A | 5305 | phosphatidylinositol-4-phosphate 5-kinase, type II, alpha | Lipid Kinase |
| PIP5K2C | 79837 | phosphatidylinositol-4-phosphate 5-kinase, type II, gamma | kinase related |
| PIP5K3 | 200576 | phosphatidylinositol-3-phosphate/phosphatidylinositol 5-kinase, type III | Lipid Kinase |
| PIP5KL1 | 138429 | phosphatidylinositol-4-phosphate 5-kinase-like 1 | Lipid Kinase |
| PKLR | 5313 | pyruvate kinase, liver and RBC | carbohydrate kinase |
| PKM2 | 5315 | pyruvate kinase, muscle | carbohydrate kinase |
| PKMYT1 | 9088 | membrane-associated tyrosine- and threonine-specific cdc2-inhibitory kinase | protein kinase (NRS/TK) |
| PLAU | 5328 | plasminogen activator, urokinase | kinase related |
| PLK1 | 5347 | polo-like kinase 1 (*Drosophila*) | protein kinase (NRS/TK) |
| PLK2 | 10769 | polo-like kinase 2 (*Drosophila*) | protein kinase (NRS/TK) |
| PLK4 | 10733 | polo-like kinase 4 (*Drosophila*) | protein kinase (NRS/TK) |
| PLXNA3 | 55558 | plexin A3; PLXNA3 | protein kinase (RTK) |
| PLXNA4B | 91584 | plexin A4, B; PLXNA4B | protein kinase (RTK) |
| PLXNB2 | 23654 | plexin B2; PLXNB2 | protein kinase (RTK) |
| PMVK | 10654 | phosphomevalonate kinase | kinase related |
| PNCK | 139728 | pregnancy upregulated non-ubiquitously expressed CaM kinase | protein kinase (NRS/TK) |
| PNKP | 11284 | polynucleotide kinase 3'-phosphatase | nucleotide kinase |
| PRKAA1 | 5562 | protein kinase, AMP-activated, alpha 1 catalytic subunit | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| PRKAA2 | 5563 | protein kinase, AMP-activated, alpha 2 catalytic subunit | protein kinase (NRS/TK) |
| PRKAB1 | 5564 | protein kinase, AMP-activated, beta 1 non-catalytic subunit | protein kinase (NRS/TK) |
| PRKAB2 | 5565 | protein kinase, AMP-activated, beta 2 non-catalytic subunit | protein kinase (NRS/TK) |
| PRKACA | 5566 | protein kinase, cAMP-dependent, catalytic, alpha | protein kinase (NRS/TK) |
| PRKACB | 5567 | protein kinase, cAMP-dependent, catalytic, beta | protein kinase (NRS/TK) |
| PRKACG | 5568 | protein kinase, cAMP-dependent, catalytic, gamma | protein kinase (NRS/TK) |
| PRKAG1 | 5571 | protein kinase, AMP-activated, gamma 1 non-catalytic subunit | protein kinase (NRS/TK) |
| PRKAG2 | 51422 | protein kinase, AMP-activated, gamma 2 non-catalytic subunit | protein kinase (NRS/TK) |
| PRKAG3 | 53632 | protein kinase, AMP-activated, gamma 3 non-catalytic subunit | protein kinase (NRS/TK) |
| PRKAR1A | 5573 | protein kinase, cAMP-dependent, regulatory, type I, alpha (tissue specific extinguisher 1) | protein kinase (NRS/TK) |
| PRKAR1B | 5575 | protein kinase, cAMP-dependent, regulatory, type I, beta | protein kinase (NRS/TK) |
| PRKAR2A | 5576 | protein kinase, cAMP-dependent, regulatory, type II, alpha | protein kinase (NRS/TK) |
| PRKAR2B | 5577 | protein kinase, cAMP-dependent, regulatory, type II, beta | protein kinase (NRS/TK) |
| PRKCA | 5578 | protein kinase C, alpha | protein kinase (NRS/TK) |
| PRKCB1 | 5579 | protein kinase C, beta 1 | protein kinase (NRS/TK) |
| PRKCE | 5581 | protein kinase C, epsilon | protein kinase (NRS/TK) |
| PRKCG | 5582 | protein kinase C, gamma | protein kinase (NRS/TK) |
| PRKCH | 5583 | protein kinase C, eta | protein kinase (NRS/TK) |
| PRKCI | 5584 | protein kinase C, iota | protein kinase (NRS/TK) |
| PRKCQ | 5588 | protein kinase C, theta | protein kinase (NRS/TK) |
| PRKCZ | 5590 | protein kinase C, zeta | protein kinase (NRS/TK) |
| PRKD1 | 5587 | protein kinase D1 | protein kinase (NRS/TK) |
| PRKD2 | 25865 | protein kinase D2 | protein kinase (NRS/TK) |
| PRKD3 | 23683 | protein kinase D3 | protein kinase (NRS/TK) |
| PRKG1 | 5592 | protein kinase, cGMP-dependent, type I | protein kinase (NRS/TK) |
| PRKG2 | 5593 | protein kinase, cGMP-dependent, type II | protein kinase (NRS/TK) |
| PRKR | 5610 | protein kinase, interferon-inducible double stranded RNA dependent | protein kinase (NRS/TK) |
| PRKX | 5613 | protein kinase, X-linked | protein kinase (NRS/TK) |
| PRKY | 5616 | protein kinase, Y-linked | protein kinase (NRS/TK) |
| PRPF4B | 8899 | PRP4 pre-mRNA processing factor 4 homolog B (yeast) | protein kinase (NRS/TK) |
| PRPS1 | 5631 | phosphoribosyl pyrophosphate synthetase 1; PRPS1 | kinase related |
| PRPS1L1 | 221823 | phosphoribosyl pyrophosphate synthetase 1-like 1; PRPS1L1 | kinase related |
| PRPS2 | 5634 | phosphoribosyl pyrophosphate synthetase 2; PRPS2 | kinase related |
| PSKH1 | 5681 | protein serine kinase H1 | protein kinase (NRS/TK) |
| PTK2 | 5747 | PTK2 protein tyrosine kinase 2 | protein kinase (NRTK) |
| PTK2B | 2185 | PTK2B protein tyrosine kinase 2 beta | protein kinase (NRTK) |
| PTK6 | 5753 | PTK6 protein tyrosine kinase 6 | protein kinase (NRTK) |
| PTK7 | 5754 | PTK7 protein tyrosine kinase 7 | protein kinase (RTK) |
| PTK9 | 5756 | PTK9 protein tyrosine kinase 9 | protein kinase (NRTK) |
| PXK | 54899 | PX domain containing serine/threonine kinase | kinase related |
| RAF1 | 5894 | v-raf-1 murine leukemia viral oncogene homolog 1 | protein kinase (NRS/TK) |
| RAGE | 5891 | renal tumor antigen | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| RBKS | 64080 | ribokinase | nucleotide kinase |
| RET | 5979 | ret proto-oncogene (multiple endocrine neoplasia and medullary thyroid carcinoma 1, Hirschsprung disease) | protein kinase (RTK) |
| RFK | 55312 | riboflavin kinase | kinase related |
| RIOK1 | 83732 | RIO kinase 1 (yeast) | protein kinase (NRS/TK) |
| RIOK2 | 55781 | RIO kinase 2 (yeast) | protein kinase (NRS/TK) |
| RIOK3 | 8780 | RIO kinase 3 (yeast) | protein kinase (NRS/TK) |
| RIPK1 | 8737 | receptor (TNFRSF)-interacting serine-threonine kinase 1 | protein kinase (NRS/TK) |
| RIPK2 | 8767 | receptor-interacting serine-threonine kinase 2 | protein kinase (NRS/TK) |
| RIPK5 | 25778 | receptor interacting protein kinase 5 | protein kinase (NRS/TK) |
| RKHD3 | 84206 | ring finger and KH domain containing 3; RKHD3 | protein kinase |
| ROR2 | 4920 | receptor tyrosine kinase-like orphan receptor 2 | protein kinase (RTK) |
| RP2 | 6102 | retinitis pigmentosa 2 (X-linked recessive); RP2 | nucleotide kinase |
| RP6-213H19.1 | 51765 | Mst3 and SOK1-related kinase | protein kinase |
| RPS6KA1 | 6195 | ribosomal protein S6 kinase, 90 kDa, polypeptide 1 | protein kinase (NRS/TK) |
| RPS6KA2 | 6196 | ribosomal protein S6 kinase, 90 kDa, polypeptide 2 | protein kinase (NRS/TK) |
| RPS6KA3 | 6197 | ribosomal protein S6 kinase, 90 kDa, polypeptide 3 | protein kinase (NRS/TK) |
| RPS6KA4 | 8986 | ribosomal protein S6 kinase, 90 kDa, polypeptide 4 | protein kinase (NRS/TK) |
| RPS6KA5 | 9252 | ribosomal protein S6 kinase, 90 kDa, polypeptide 5 | protein kinase (NRS/TK) |
| RPS6KA6 | 27330 | ribosomal protein S6 kinase, 90 kDa, polypeptide 6 | protein kinase (NRS/TK) |
| RPS6KB1 | 6198 | ribosomal protein S6 kinase, 70 kDa, polypeptide 1 | protein kinase (NRS/TK) |
| RPS6KB2 | 6199 | ribosomal protein S6 kinase, 70 kDa, polypeptide 2 | protein kinase (NRS/TK) |
| RPS6KC1 | 26750 | ribosomal protein S6 kinase, 52 kDa, polypeptide 1 | protein kinase (NRS/TK) |
| RPS6KL1 | 83694 | ribosomal protein S6 kinase-like 1 | protein kinase (NRS/TK) |
| SCYL1 | 57410 | SCY1-like 1 (*S. cerevisiae*) | protein kinase (NRTK) |
| SCYL2 | 55681 | hypothetical protein FLJ10074 | protein kinase (NRTK) |
| SCYL3 | 57147 | ezrin-binding partner PACE-1 | protein kinase (NRTK) |
| SEPHS2 | 22928 | selenophosphate synthetase 2; SEPHS2 | kinase related |
| SGK | 6446 | serum/glucocorticoid regulated kinase | protein kinase (NRS/TK) |
| SGK2 | 10110 | serum/glucocorticoid regulated kinase 2 | protein kinase (NRS/TK) |
| SGK3 | 23678 | serum/glucocorticoid regulated kinase-like | protein kinase (NRS/TK) |
| SH3BP4 | 23677 | SH3-domain binding protein 4; SH3BP4 | protein kinase (NRTK) |
| SH3BP5 | 9467 | SH3-domain binding protein 5 (BTK-associated); SH3BP5 | kinase related |
| SH3BP5L | 80851 | SH3-binding domain protein 5-like; SH3BP5L | kinase related |
| SLAMF6 | 114836 | SLAM family member 6; SLAMF6 | protein kinase (RTK) |
| SNF1LK | 150094 | SNF1-like kinase | protein kinase (NRS/TK) |
| SNRK | 54861 | SNF-1 related kinase | protein kinase (NRS/TK) |
| SNX16 | 64089 | sorting nexin 16; SNX16 | kinase related |
| SPHK1 | 8877 | sphingosine kinase 1 | carbohydrate kinase |
| SPHK2 | 56848 | sphingosine kinase 2 | carbohydrate kinase |
| SRC | 6714 | v-src sarcoma (Schmidt-Ruppin A-2) viral oncogene homolog (avian) | protein kinase (NRTK) |
| SRPK1 | 6732 | SFRS protein kinase 1 | protein kinase (NRS/TK) |
| SRPK2 | 6733 | SFRS protein kinase 2 | protein kinase (NRS/TK) |
| SRPK3 | 26576 | serine/threonine kinase 23 | protein kinase (NRS/TK) |
| STK11 | 6794 | serine/threonine kinase 11 (Peutz-Jeghers syndrome) | protein kinase (NRS/TK) |
| STK16 | 8576 | serine/threonine kinase 16 | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| STK17B | 9262 | serine/threonine kinase 17b (apoptosis-inducing) | protein kinase (NRS/TK) |
| STK19 | 8859 | serine/threonine kinase 19 | protein kinase (NRS/TK) |
| STK24 | 8428 | serine/threonine kinase 24 (STE20 homolog, yeast) | protein kinase |
| STK25 | 10494 | serine/threonine kinase 25 (STE20 homolog, yeast) | protein kinase |
| STK3 | 6788 | serine/threonine kinase 3 (STE20 homolog, yeast) | protein kinase |
| STK32A | 202374 | serine/threonine kinase 32A | protein kinase (NRS/TK) |
| STK32B | 55351 | serine/threonine kinase 32B | protein kinase (NRS/TK) |
| STK32C | 282974 | serine/threonine kinase 32C | protein kinase (NRS/TK) |
| STK33 | 65975 | serine/threonine kinase 33 | protein kinase (NRS/TK) |
| STK36 | 27148 | serine/threonine kinase 36 (fused homolog, *Drosophila*) | protein kinase (RS/TK) |
| STK38 | 11329 | serine/threonine kinase 38 | protein kinase (NRS/TK) |
| STK38L | 23012 | serine/threonine kinase 38 like | protein kinase (NRS/TK) |
| STK40 | 83931 | Ser/Thr-like kinase | protein kinase |
| STYK1 | 55359 | protein kinase STYK1 | protein kinase (RTK) |
| SYK | 6850 | spleen tyrosine kinase | protein kinase (NRTK) |
| TAOK3 | 51347 | TAO kinase 3 | protein kinase |
| TBK1 | 29110 | TANK-binding kinase 1 | protein kinase (NRS/TK) |
| TEC | 7006 | tec protein tyrosine kinase | protein kinase (NRTK) |
| TESK1 | 7016 | testis-specific kinase 1 | protein kinase (NRS/TK) |
| TESK2 | 10420 | testis-specific kinase 2 | protein kinase (NRS/TK) |
| TGFBR1 | 7046 | transforming growth factor, beta receptor I (activin A receptor type II-like kinase, 53 kDa) | protein kinase (RS/TK) |
| TGFBR2 | 7048 | transforming growth factor, beta receptor II (70/80 kDa) | protein kinase (RS/TK) |
| TGFBR3 | 7049 | transforming growth factor, beta receptor III (betaglycan, 300 kDa); TGFBR3 | protein kinase (RS/TK) |
| TIE1 | 7075 | tyrosine kinase with immunoglobulin-like and EGF-like domains 1 | protein kinase (RTK) |
| TK1 | 7083 | thymidine kinase 1, soluble | nucleotide kinase |
| TLK1 | 9874 | tousled-like kinase 1 | protein kinase (NRS/TK) |
| TLK2 | 11011 | tousled-like kinase 2 | protein kinase (NRS/TK) |
| TNK1 | 8711 | tyrosine kinase, non-receptor, 1 | protein kinase (NRTK) |
| TNNI3K | 51086 | TNNI3 interacting kinase | protein kinase |
| TP53RK | 112858 | TP53 regulating kinase | protein kinase (NRS/TK) |
| TPK1 | 27010 | thiamin pyrophosphokinase 1 | kinase related |
| TPR | 7175 | translocated promoter region (to activated MET oncogene); TPR | protein kinase (RTK) |
| TRIB1 | 10221 | tribbles homolog 1 (*Drosophila*) | protein kinase |
| TRIB2 | 28951 | tribbles homolog 2 (*Drosophila*) | protein kinase |
| TRIB3 | 57761 | tribbles homolog 3 (*Drosophila*) | protein kinase |
| TRIM27 | 5987 | tripartite motif-containing 27; TRIM27 | protein kinase (RTK) |
| TRPM7 | 54822 | transient receptor potential cation channel, subfamily M, member 7 | protein kinase (NRS/TK) |
| TSSK1 | 83942 | serine/threonine kinase 22D (spermiogenesis associated) | protein kinase (NRS/TK) |
| TSSK2 | 23617 | serine/threonine kinase 22B (spermiogenesis associated) | protein kinase (NRS/TK) |
| TSSK3 | 81629 | serine/threonine kinase 22C (spermiogenesis associated) | protein kinase (NRS/TK) |
| TSSK6 | 83983 | serine/threonine protein kinase SSTK | protein kinase (NRS/TK) |
| TTK | 7272 | TTK protein kinase | protein kinase |
| TWF2 | 11344 | PTK9L protein tyrosine kinase 9-like (A6-related protein) | protein kinase (NRTK) |
| TXK | 7294 | TXK tyrosine kinase | protein kinase (NRTK) |
| TXNDC3 | 51314 | thioredoxin domain containing 3 (spermatozoa); TXNDC3 | nucleotide kinase |
| TYK2 | 7297 | tyrosine kinase 2 | protein kinase (NRTK) |
| TYRO3 | 7301 | TYRO3 protein tyrosine kinase | protein kinase (RTK) |
| UCK2 | 7371 | uridine-cytidine kinase 2 | nucleotide kinase |
| UHMK1 | 127933 | U2AF homology motif (UHM) kinase 1 | protein kinase (NRS/TK) |
| ULK2 | 9706 | unc-51-like kinase 2 (*C. elegans*) | protein kinase (NRS/TK) |
| ULK3 | 25989 | DKFZP434C131 protein | protein kinase (NRS/TK) |

TABLE 3-continued

CCSB/Broad Institute Kinase ORF Library description and ORF classification

| hGENE | GENE ID | DESCRIPTION | KINASE CLASS |
|---|---|---|---|
| ULK4 | 54986 | hypothetical protein FLJ20574 | protein kinase |
| VRK1 | 7443 | vaccinia related kinase 1 | protein kinase (NRS/TK) |
| VRK2 | 7444 | vaccinia related kinase 2 | protein kinase (NRS/TK) |
| VRK3 | 51231 | vaccinia related kinase 3 | protein kinase (NRS/TK) |
| WNK1 | 65125 | protein kinase, lysine deficient 1 | protein kinase (NRS/TK) |
| WNK4 | 65266 | protein kinase, lysine deficient 4 | protein kinase (NRS/TK) |
| XRCC6BP1 | 91419 | XRCC6 binding protein 1; XRCC6BP1 | protein kinase |
| XYLB | 9942 | xylulokinase homolog (*H. influenzae*) | carbohydrate kinase |
| YES1 | 7525 | v-yes-1 Yamaguchi sarcoma viral oncogene homolog 1 | protein kinase (NRTK) |
| YSK4 | 80122 | hypothetical protein FLJ23074 | protein kinase |
| ZAK | 51776 | sterile alpha motif and leucine zipper containing kinase AZK | protein kinase (NRS/TK) |
| ZAP70 | 7535 | zeta-chain (TCR) associated protein kinase 70 kDa | protein kinase (NRTK) |

Abbreviations:
RS/TK (Receptor Serine/Threonine Kinase);
RTK (Receptor Tyrosine Kinase);
NRS/TK(Non-Receptor Serine/Threonine Kinase);
NRTK (Non-Receptor Tyrosine Kinase)

TABLE 4

Ranking of average differential proliferation (1 μM PLX4720/control) for 597 kinase-related ORFs, relative to MEK DD

| RANK | GENE | AVERAGE | STDEV. | Z-SCORE | NOTES |
|---|---|---|---|---|---|
| — | ALL ORFS | 44.26% | 7.19% | — | |
| 1 | MEK DD | 100.00% | 6.54% | 7.75 | (+) Control |
| 2 | RAF1 | 86.80% | 18.00% | 5.92 | |
| 3 | PRKCE | 74.76% | 8.78% | 4.24 | |
| 4 | MAP3K8 | 67.51% | 10.03% | 3.23 | |
| 5 | PRKCH | 67.37% | 17.56% | 3.21 | |
| 6 | FGR | 65.03% | 20.76% | 2.89 | |
| 7 | CRKL | 64.74% | 19.66% | 2.85 | |
| 8 | PAK3 | 60.33% | 13.59% | 2.23 | |
| 9 | AXL | 59.75% | 10.23% | 2.15 | |
| 10 | LCK | 59.47% | 15.66% | 2.11 | Lethal |
| 11 | ERBB2 | 59.32% | 9.39% | 2.09 | 2 SD = 58.64% |
| 12 | PRKCQ | 55.40% | 11.97% | 1.55 | |
| 13 | NME3 | 55.10% | 15.46% | 1.51 | |
| 14 | MOS | 55.04% | 11.84% | 1.50 | |
| 15 | KHK | 55.03% | 14.75% | 1.50 | |
| 16 | TIE1 | 54.65% | 15.26% | 1.44 | Proliferative |
| 17 | PRKAG2 | 54.23% | 7.15% | 1.39 | |
| 18 | LOC91461 | 53.75% | 12.45% | 1.32 | |
| 19 | TYRO3 | 53.64% | 10.57% | 1.30 | |
| 20 | CDK3 | 53.55% | 13.92% | 1.29 | |
| 21 | PIM2 | 53.36% | 10.78% | 1.27 | |
| 22 | CIB4 | 53.31% | 12.21% | 1.26 | |
| 23 | PRPS2 | 53.24% | 14.53% | 1.25 | |
| 24 | PRKCB1 | 53.12% | 7.74% | 1.23 | |
| 25 | ACVR1B | 53.08% | 9.53% | 1.23 | |
| 26 | ETNK2 | 52.85% | 12.63% | 1.19 | |
| 27 | STK36 | 52.85% | 15.28% | 1.19 | |
| 28 | DDR1 | 52.78% | 15.54% | 1.19 | |
| 29 | PRKCA | 52.47% | 13.38% | 1.14 | |
| 30 | AURKB | 52.22% | 11.80% | 1.11 | |
| 31 | CAMK4 | 52.14% | 9.09% | 1.10 | |
| 32 | DAPK1 | 51.94% | 11.43% | 1.07 | |
| 33 | AURKC | 51.89% | 11.23% | 1.06 | Proliferative |
| 34 | IGF1R | 51.35% | 10.70% | 0.99 | |
| 35 | FN3K | 51.27% | 12.65% | 0.97 | |
| 36 | LOC646505 | 50.97% | 16.89% | 0.93 | |
| 37 | PIK3CB | 50.90% | 12.87% | 0.92 | |
| 38 | YES1 | 50.68% | 9.51% | 0.89 | |
| 39 | LOC340156 | 50.59% | 14.63% | 0.88 | |

TABLE 4-continued

Ranking of average differential proliferation (1 μM PLX4720/control) for 597 kinase-related ORFs, relative to MEK DD

| RANK | GENE | AVERAGE | STDEV. | Z-SCORE | NOTES |
|---|---|---|---|---|---|
| 40 | MAP4K5 | 50.57% | 35.45% | 0.88 | |
| 41 | ABL1 | 50.55% | 19.09% | 0.87 | |
| 42 | MAP2K1IP1 | 50.47% | 11.54% | 0.86 | |
| 43 | PRKAR1B | 50.34% | 8.31% | 0.84 | |
| 44 | RPS6KA1 | 50.12% | 12.28% | 0.81 | |
| 45 | TSSK6 | 50.10% | 11.70% | 0.81 | |
| 46 | NEK9 | 50.04% | 14.37% | 0.80 | |
| 47 | DLG1 | 49.98% | 12.07% | 0.80 | |
| 48 | PTK6 | 49.93% | 10.93% | 0.79 | |
| 49 | SCYL2 | 49.85% | 12.51% | 0.78 | |
| 50 | STK11 | 49.82% | 12.10% | 0.77 | |
| 51 | C9orf98 | 49.82% | 10.38% | 0.77 | |
| 52 | PCK2 | 49.77% | 12.93% | 0.77 | |
| 53 | NTRK2 | 49.77% | 10.02% | 0.77 | |
| 54 | TRIM27 | 49.69% | 10.38% | 0.75 | |
| 55 | FN3KRP | 49.69% | 11.83% | 0.75 | |
| 56 | CAMK2D | 49.61% | 11.93% | 0.74 | |
| 57 | ALPK2 | 49.56% | 10.41% | 0.74 | |
| 58 | LOC652722 | 49.52% | 13.10% | 0.73 | |
| 59 | LATS2 | 49.49% | 12.45% | 0.73 | |
| 60 | STK3 | 49.48% | 10.15% | 0.73 | |
| 61 | CDC42BPG | 49.44% | 10.19% | 0.72 | |
| 62 | HKDC1 | 49.44% | 11.53% | 0.72 | |
| 63 | CDK7 | 49.42% | 14.45% | 0.72 | Proliferative |
| 64 | WNK4 | 49.37% | 14.07% | 0.71 | |
| 65 | PRPF4B | 49.36% | 12.18% | 0.71 | |
| 66 | MAPKAPK2 | 49.30% | 12.83% | 0.70 | |
| 67 | MEK WT | 49.29% | 14.33% | 0.70 | (−) Control |
| 68 | PRPS1 | 49.28% | 12.09% | 0.70 | |
| 69 | BTK | 49.22% | 14.59% | 0.69 | |
| 70 | MYO3B | 49.19% | 11.05% | 0.69 | |
| 71 | TESK1 | 49.18% | 12.19% | 0.68 | |
| 72 | PLXNA3 | 49.11% | 9.04% | 0.67 | |
| 73 | CLK2 | 49.09% | 8.01% | 0.67 | |
| 74 | PFKFB1 | 49.02% | 14.04% | 0.66 | |
| 75 | DAK | 49.00% | 12.68% | 0.66 | |
| 76 | ITPKB | 48.99% | 16.62% | 0.66 | |
| 77 | CHEK1 | 48.98% | 14.41% | 0.66 | |
| 78 | MERTK | 48.94% | 12.88% | 0.65 | |
| 79 | IKBKE | 48.83% | 12.46% | 0.63 | |
| 80 | CARD11 | 48.83% | 15.02% | 0.63 | |
| 81 | PANK3 | 48.78% | 9.70% | 0.63 | |
| 82 | TRIB2 | 48.76% | 10.71% | 0.63 | |
| 83 | CDC7 | 48.74% | 9.83% | 0.62 | |
| 84 | PIK3C3 | 48.69% | 12.05% | 0.62 | |
| 85 | LRGUK | 48.60% | 11.29% | 0.60 | |
| 86 | SCYL3 | 48.58% | 10.86% | 0.60 | |
| 87 | MAP3K14 | 48.57% | 8.10% | 0.60 | |
| 88 | LOC730000 | 48.57% | 13.36% | 0.60 | |
| 89 | LOC442075 | 48.55% | 10.75% | 0.60 | |
| 90 | LOC54103 | 48.50% | 10.77% | 0.59 | |
| 91 | NPR2 | 48.49% | 13.29% | 0.59 | |
| 92 | COL4A3BP | 48.49% | 11.10% | 0.59 | |
| 93 | MYLK2 | 48.49% | 11.83% | 0.59 | |
| 94 | CSNK2B | 48.48% | 11.52% | 0.59 | |
| 95 | CARKL | 48.47% | 9.19% | 0.58 | |
| 96 | TP53RK | 48.44% | 14.25% | 0.58 | Proliferative |
| 97 | PRKCG | 48.42% | 8.31% | 0.58 | |
| 98 | ALK | 48.39% | 14.07% | 0.57 | |
| 99 | ETNK1 | 48.37% | 11.25% | 0.57 | |
| 100 | DYRK2 | 48.36% | 11.80% | 0.57 | |
| 101 | DGKA | 48.31% | 10.71% | 0.56 | |
| 102 | ADPGK | 48.30% | 13.36% | 0.56 | |
| 103 | PRKAB2 | 48.29% | 10.75% | 0.56 | |
| 104 | ULK3 | 48.28% | 11.18% | 0.56 | |
| 105 | KIAA2002 | 48.28% | 12.39% | 0.56 | |
| 106 | IRAK3 | 48.26% | 10.96% | 0.56 | |
| 107 | TYK2 | 48.24% | 10.88% | 0.55 | |
| 108 | MAP2K7 | 48.23% | 12.06% | 0.55 | |
| 109 | NRBP | 48.18% | 13.40% | 0.54 | |
| 110 | CDK2 | 48.14% | 14.65% | 0.54 | |
| 111 | MORN2 | 47.98% | 11.36% | 0.52 | |
| 112 | EPHB4 | 47.92% | 12.52% | 0.51 | |
| 113 | PRKCZ | 47.88% | 12.68% | 0.50 | |
| 114 | RFK | 47.85% | 10.44% | 0.50 | |

TABLE 4-continued

Ranking of average differential proliferation (1 µM PLX4720/control) for 597 kinase-related ORFs, relative to MEK DD

| RANK | GENE | AVERAGE | STDEV. | Z-SCORE | NOTES |
|---|---|---|---|---|---|
| 115 | RAGE | 47.83% | 10.46% | 0.50 | |
| 116 | LOC91807 | 47.80% | 11.25% | 0.49 | |
| 117 | PIK3CG | 47.76% | 11.25% | 0.49 | |
| 118 | PIK3C2G | 47.74% | 10.75% | 0.48 | |
| 119 | ARSG | 47.71% | 10.26% | 0.48 | |
| 120 | CSNK1A1L | 47.66% | 10.26% | 0.47 | |
| 121 | ALS2CR7 | 47.65% | 11.56% | 0.47 | |
| 122 | FLJ40852 | 47.62% | 12.34% | 0.47 | |
| 123 | LOC390877 | 47.61% | 11.43% | 0.46 | |
| 124 | TRIB1 | 47.59% | 12.91% | 0.46 | |
| 125 | TPR | 47.58% | 13.00% | 0.46 | |
| 126 | RPS6KL1 | 47.57% | 12.33% | 0.46 | |
| 127 | CCRK | 47.56% | 10.28% | 0.46 | |
| 128 | PDPK1 | 47.53% | 10.42% | 0.45 | |
| 129 | FASTKD5 | 47.52% | 10.70% | 0.45 | |
| 130 | CDKL3 | 47.49% | 13.14% | 0.45 | |
| 131 | DTYMK | 47.49% | 10.60% | 0.45 | |
| 132 | MPP3 | 47.47% | 10.65% | 0.45 | |
| 133 | HSPB8 | 47.46% | 11.73% | 0.44 | |
| 134 | NME6 | 47.44% | 14.48% | 0.44 | |
| 135 | NEK3 | 47.42% | 15.46% | 0.44 | |
| 136 | PIK3R4 | 47.41% | 11.14% | 0.44 | |
| 137 | MGC16169 | 47.41% | 13.90% | 0.44 | |
| 138 | OXSR1 | 47.40% | 11.68% | 0.44 | |
| 139 | MASTL | 47.35% | 10.28% | 0.43 | |
| 140 | PNCK | 47.35% | 10.15% | 0.43 | |
| 141 | ADCK2 | 47.32% | 15.57% | 0.43 | |
| 142 | SNX16 | 47.26% | 12.76% | 0.42 | |
| 143 | HCK | 47.24% | 23.41% | 0.41 | |
| 144 | CDKL2 | 47.21% | 10.60% | 0.41 | |
| 145 | NEK11 | 47.20% | 14.68% | 0.41 | |
| 146 | BMP2K | 47.15% | 11.18% | 0.40 | |
| 147 | BUB1 | 47.15% | 11.76% | 0.40 | |
| 148 | PINK1 | 47.13% | 11.38% | 0.40 | |
| 149 | RBKS | 47.08% | 8.73% | 0.39 | |
| 150 | LOC732306 | 47.03% | 8.82% | 0.39 | |
| 151 | PKLR | 47.03% | 12.10% | 0.38 | |
| 152 | DYRK1A | 47.01% | 12.69% | 0.38 | |
| 153 | RPS6KA4 | 47.01% | 11.70% | 0.38 | |
| 154 | DGKG | 46.94% | 12.71% | 0.37 | |
| 155 | CDK5R1 | 46.93% | 9.40% | 0.37 | |
| 156 | FLJ25006 | 46.87% | 11.64% | 0.36 | |
| 157 | PBK | 46.86% | 14.05% | 0.36 | |
| 158 | ACVR1C | 46.82% | 9.98% | 0.35 | |
| 159 | FLT1 | 46.78% | 10.42% | 0.35 | |
| 160 | PLXNA4B | 46.76% | 9.39% | 0.35 | |
| 161 | MVK | 46.71% | 9.26% | 0.34 | |
| 162 | LIMK2 | 46.70% | 11.29% | 0.34 | |
| 163 | DYRK1B | 46.68% | 20.75% | 0.34 | |
| 164 | MARK3 | 46.67% | 11.71% | 0.34 | Proliferative |
| 165 | BMPR1B | 46.66% | 12.24% | 0.33 | |
| 166 | NUP62 | 46.63% | 9.92% | 0.33 | |
| 167 | JAK2 | 46.62% | 12.50% | 0.33 | |
| 168 | MAPK12 | 46.55% | 9.98% | 0.32 | |
| 169 | DDR2 | 46.54% | 7.99% | 0.32 | |
| 170 | MAK | 46.52% | 15.42% | 0.31 | |
| 171 | GLYCTK | 46.50% | 13.19% | 0.31 | |
| 172 | AK1 | 46.47% | 9.68% | 0.31 | |
| 173 | MAPK15 | 46.47% | 11.14% | 0.31 | |
| 174 | MAST1 | 46.45% | 10.77% | 0.30 | |
| 175 | PAPSS2 | 46.39% | 11.53% | 0.30 | |
| 176 | CSF1R | 46.34% | 12.86% | 0.29 | |
| 177 | TPK1 | 46.29% | 9.52% | 0.28 | |
| 178 | PAK4 | 46.24% | 9.98% | 0.28 | |
| 179 | NAGK | 46.21% | 12.34% | 0.27 | |
| 180 | CDK8 | 46.20% | 7.68% | 0.27 | |
| 181 | STK40 | 46.19% | 12.92% | 0.27 | |
| 182 | CIB1 | 46.10% | 10.92% | 0.26 | |
| 183 | PLK1 | 46.08% | 9.99% | 0.25 | |
| 184 | FLJ23356 | 46.04% | 10.45% | 0.25 | |
| 185 | LOC220686 | 46.04% | 9.31% | 0.25 | |
| 186 | PRKAB1 | 46.03% | 12.00% | 0.25 | |
| 187 | JAK3 | 46.02% | 10.17% | 0.24 | |
| 188 | NME1 | 46.02% | 13.01% | 0.24 | |
| 189 | NME5 | 46.00% | 11.53% | 0.24 | |

TABLE 4-continued

Ranking of average differential proliferation (1 µM PLX4720/control) for 597 kinase-related ORFs, relative to MEK DD

| RANK | GENE | AVERAGE | STDEV. | Z-SCORE | NOTES |
|---|---|---|---|---|---|
| 190 | FER | 45.97% | 9.92% | 0.24 | |
| 191 | AK3L1 | 45.97% | 10.39% | 0.24 | |
| 192 | PRKG2 | 45.90% | 13.24% | 0.23 | |
| 193 | RP6-213H19.1 | 45.88% | 12.83% | 0.22 | |
| 194 | AKT3 | 45.87% | 11.32% | 0.22 | |
| 195 | PSKH1 | 45.86% | 10.16% | 0.22 | |
| 196 | PRKAR2B | 45.84% | 13.05% | 0.22 | |
| 197 | FUK | 45.81% | 10.94% | 0.22 | |
| 198 | ADCK4 | 45.79% | 11.25% | 0.21 | |
| 199 | TEC | 45.78% | 11.46% | 0.21 | |
| 200 | PRKAG1 | 45.77% | 11.08% | 0.21 | |
| 201 | FXN | 45.77% | 12.03% | 0.21 | |
| 202 | AAK1 | 45.68% | 11.49% | 0.20 | |
| 203 | CAMK2B | 45.67% | 19.84% | 0.20 | |
| 204 | COASY | 45.64% | 11.07% | 0.19 | |
| 205 | PRKAG3 | 45.63% | 10.21% | 0.19 | |
| 206 | NME7 | 45.58% | 10.18% | 0.18 | |
| 207 | LMTK2 | 45.58% | 12.15% | 0.18 | |
| 208 | PANK2 | 45.57% | 11.72% | 0.18 | |
| 209 | PRKD3 | 45.47% | 13.14% | 0.17 | |
| 210 | PHKA2 | 45.47% | 10.92% | 0.17 | |
| 211 | SLAMF6 | 45.46% | 9.67% | 0.17 | |
| 212 | SRPK1 | 45.46% | 12.54% | 0.17 | |
| 213 | HIPK1 | 45.42% | 12.59% | 0.16 | |
| 214 | EPHA1 | 45.39% | 10.59% | 0.16 | |
| 215 | WNK1 | 45.38% | 13.79% | 0.15 | |
| 216 | PDIK1L | 45.33% | 12.31% | 0.15 | |
| 217 | BMP2KL | 45.33% | 10.08% | 0.15 | |
| 218 | MAP3K5 | 45.32% | 14.13% | 0.15 | |
| 219 | EPHA2 | 45.30% | 12.87% | 0.14 | |
| 220 | CCL2 | 45.29% | 9.71% | 0.14 | |
| 221 | CDKL1 | 45.25% | 10.13% | 0.14 | |
| 222 | NJMU-R1 | 45.23% | 8.13% | 0.13 | |
| 223 | LOC652799 | 45.18% | 10.30% | 0.13 | |
| 224 | GUK1 | 45.15% | 12.23% | 0.12 | |
| 225 | NME4 | 45.12% | 13.03% | 0.12 | |
| 226 | YSK4 | 45.11% | 13.47% | 0.12 | |
| 227 | NEK2 | 45.11% | 9.38% | 0.12 | |
| 228 | C9orf95 | 45.10% | 9.38% | 0.12 | |
| 229 | CDC2 | 45.05% | 11.95% | 0.11 | |
| 230 | FGFR2 | 45.01% | 11.23% | 0.10 | |
| 231 | IPMK | 44.98% | 10.67% | 0.10 | |
| 232 | STK32C | 44.98% | 12.10% | 0.10 | |
| 233 | PIP5K2A | 44.92% | 14.55% | 0.09 | |
| 234 | PRKX | 44.90% | 10.44% | 0.09 | |
| 235 | TRPM7 | 44.80% | 10.36% | 0.07 | |
| 236 | FLJ10986 | 44.74% | 10.95% | 0.07 | |
| 237 | SNF1LK | 44.74% | 12.70% | 0.07 | |
| 238 | MAP3K6 | 44.71% | 9.75% | 0.06 | |
| 239 | LOC653052 | 44.70% | 14.56% | 0.06 | |
| 240 | IRAK2 | 44.69% | 11.61% | 0.06 | |
| 241 | XYLB | 44.68% | 11.47% | 0.06 | |
| 242 | PTK7 | 44.67% | 14.55% | 0.06 | |
| 243 | PKMYT1 | 44.66% | 13.74% | 0.05 | |
| 244 | SPHK2 | 44.63% | 10.35% | 0.05 | |
| 245 | NME2 | 44.63% | 11.57% | 0.05 | |
| 246 | PRKAA1 | 44.62% | 15.03% | 0.05 | |
| 247 | MAPK14 | 44.60% | 10.77% | 0.05 | |
| 248 | NTRK3 | 44.58% | 13.43% | 0.04 | |
| 249 | PRKACB | 44.58% | 9.30% | 0.04 | |
| 250 | LOC650122 | 44.56% | 11.24% | 0.04 | |
| 251 | CDK6 | 44.51% | 10.74% | 0.03 | |
| 252 | AMHR2 | 44.48% | 11.11% | 0.03 | |
| 253 | IPPK | 44.42% | 10.63% | 0.02 | |
| 254 | AK7 | 44.41% | 10.36% | 0.02 | |
| 255 | PIP5KL1 | 44.36% | 11.74% | 0.01 | |
| 256 | LOC340371 | 44.30% | 16.04% | 0.01 | |
| 257 | DKFZp434B1231 | 44.29% | 12.21% | 0.00 | |
| 258 | PRKAA2 | 44.28% | 11.42% | 0.00 | |
| 259 | FASTKD1 | 44.28% | 10.73% | 0.00 | |
| 260 | ARAF | 44.27% | 14.40% | 0.00 | RAF Family |
| 261 | HK3 | 44.26% | 14.83% | 0.00 | |
| 262 | KSR2 | 44.25% | 10.28% | 0.00 | |
| 263 | PAK7 | 44.24% | 18.45% | 0.00 | |
| 264 | GTF2H1 | 44.23% | 10.90% | 0.00 | |

TABLE 4-continued

Ranking of average differential proliferation (1 μM PLX4720/control) for 597 kinase-related ORFs, relative to MEK DD

| RANK | GENE | AVERAGE | STDEV. | Z-SCORE | NOTES |
|---|---|---|---|---|---|
| 265 | RPS6KB2 | 44.23% | 9.32% | −0.01 | |
| 266 | PAK6 | 44.21% | 13.83% | −0.01 | |
| 267 | IRAK4 | 44.18% | 10.27% | −0.01 | |
| 268 | NLK | 44.18% | 12.92% | −0.01 | |
| 269 | FYN | 44.14% | 12.43% | −0.02 | |
| 270 | BMPR2 | 44.14% | 12.20% | −0.02 | |
| 271 | CDK4 | 44.13% | 10.47% | −0.02 | |
| 272 | STK32A | 44.07% | 13.93% | −0.03 | |
| 273 | TNK1 | 44.06% | 10.80% | −0.03 | |
| 274 | STK24 | 43.99% | 10.79% | −0.04 | |
| 275 | CSNK2A1 | 43.99% | 11.97% | −0.04 | |
| 276 | AK3 | 43.98% | 11.16% | −0.04 | |
| 277 | TTK | 43.93% | 10.47% | −0.05 | |
| 278 | PGK2 | 43.91% | 13.31% | −0.05 | |
| 279 | GALK1 | 43.89% | 10.14% | −0.05 | |
| 280 | DYRK3 | 43.89% | 9.32% | −0.05 | |
| 281 | EIF2AK4 | 43.83% | 11.00% | −0.06 | |
| 282 | PDK1 | 43.79% | 13.31% | −0.07 | |
| 283 | EIF2AK1 | 43.79% | 12.02% | −0.07 | |
| 284 | PRKACG | 43.79% | 11.37% | −0.07 | |
| 285 | BUB1B | 43.74% | 10.69% | −0.07 | |
| 286 | PKM2 | 43.74% | 14.46% | −0.07 | |
| 287 | LRPPRC | 43.64% | 10.87% | −0.09 | |
| 288 | EPHA6 | 43.63% | 12.60% | −0.09 | |
| 289 | HK2 | 43.58% | 12.55% | −0.10 | |
| 290 | MET | 43.55% | 10.99% | −0.10 | |
| 291 | CKS2 | 43.53% | 7.83% | −0.10 | |
| 292 | LOC375133 | 43.53% | 10.05% | −0.10 | |
| 293 | LIMK1 | 43.52% | 12.43% | −0.10 | |
| 294 | TWF2 | 43.50% | 11.71% | −0.11 | |
| 295 | PCTK2 | 43.47% | 12.02% | −0.11 | |
| 296 | DCAKD | 43.43% | 11.61% | −0.12 | |
| 297 | PLXNB2 | 43.41% | 11.85% | −0.12 | |
| 298 | MST1R | 43.35% | 11.99% | −0.13 | |
| 299 | PRKAR1A | 43.35% | 9.03% | −0.13 | |
| 300 | SEPHS2 | 43.32% | 9.68% | −0.13 | |
| 301 | SPHK1 | 43.31% | 9.87% | −0.13 | |
| 302 | CCL4 | 43.30% | 11.83% | −0.13 | |
| 303 | KIAA0999 | 43.28% | 9.68% | −0.14 | |
| 304 | PDGFRL | 43.23% | 11.93% | −0.14 | |
| 305 | BRSK1 | 43.21% | 14.17% | −0.15 | |
| 306 | BRAF | 43.21% | 12.56% | −0.15 | RAF Family |
| 307 | MUSK | 43.20% | 11.03% | −0.15 | |
| 308 | TNNI3K | 43.20% | 10.46% | −0.15 | |
| 309 | GK2 | 43.18% | 15.15% | −0.15 | |
| 310 | CKB | 43.14% | 9.45% | −0.16 | |
| 311 | DGKB | 43.12% | 11.62% | −0.16 | |
| 312 | LOC648152 | 42.99% | 11.15% | −0.18 | |
| 313 | RPS6KA5 | 42.87% | 11.23% | −0.19 | |
| 314 | CASK | 42.87% | 12.05% | −0.19 | |
| 315 | PHKA1 | 42.86% | 10.10% | −0.20 | |
| 316 | AK2 | 42.84% | 9.83% | −0.20 | |
| 317 | PIM1 | 42.81% | 14.09% | −0.20 | |
| 318 | ZAP70 | 42.81% | 12.10% | −0.20 | |
| 319 | PNKP | 42.79% | 12.95% | −0.20 | |
| 320 | CDK10 | 42.78% | 9.77% | −0.21 | |
| 321 | CHEK2 | 42.77% | 12.86% | −0.21 | |
| 322 | CAMK2A | 42.72% | 11.68% | −0.21 | |
| 323 | CAMK2G | 42.70% | 9.66% | −0.22 | |
| 324 | ADRBK2 | 42.70% | 12.56% | −0.22 | |
| 325 | NEK8 | 42.69% | 9.88% | −0.22 | |
| 326 | PRKR | 42.69% | 10.65% | −0.22 | |
| 327 | CHKA | 42.66% | 12.84% | −0.22 | |
| 328 | ACVRL1 | 42.65% | 10.85% | −0.22 | |
| 329 | PRKY | 42.63% | 11.80% | −0.23 | |
| 330 | TRIB3 | 42.62% | 11.45% | −0.23 | |
| 331 | PRKD2 | 42.59% | 10.48% | −0.23 | |
| 332 | PIP5K3 | 42.57% | 9.78% | −0.24 | |
| 333 | LOC727761 | 42.56% | 14.17% | −0.24 | |
| 334 | PTK2B | 42.50% | 15.72% | −0.25 | |
| 335 | MPP2 | 42.48% | 10.73% | −0.25 | |
| 336 | CSNK1A1 | 42.47% | 13.54% | −0.25 | |
| 337 | PTK9 | 42.42% | 11.31% | −0.26 | |
| 338 | STK25 | 42.41% | 12.54% | −0.26 | |
| 339 | PFKL | 42.39% | 12.01% | −0.26 | |

TABLE 4-continued

Ranking of average differential proliferation (1 µM PLX4720/control) for 597 kinase-related ORFs, relative to MEK DD

| RANK | GENE | AVERAGE | STDEV. | Z-SCORE | NOTES |
|---|---|---|---|---|---|
| 340 | STK19 | 42.35% | 11.20% | −0.27 | |
| 341 | PI4KII | 42.30% | 14.04% | −0.27 | |
| 342 | HK1 | 42.26% | 12.73% | −0.28 | |
| 343 | AURKA | 42.21% | 14.80% | −0.29 | |
| 344 | GK5 | 42.21% | 10.98% | −0.29 | |
| 345 | MAP3K7 | 42.20% | 13.13% | −0.29 | |
| 346 | PFTK1 | 42.18% | 12.49% | −0.29 | |
| 347 | ERN1 | 42.17% | 13.74% | −0.29 | |
| 348 | STK33 | 42.17% | 13.22% | −0.29 | |
| 349 | SYK | 42.13% | 12.42% | −0.30 | |
| 350 | GALK2 | 42.13% | 11.34% | −0.30 | |
| 351 | TSSK1 | 42.12% | 11.98% | −0.30 | |
| 352 | MAPK6 | 42.11% | 10.58% | −0.30 | |
| 353 | ASCIZ | 42.07% | 10.61% | −0.30 | |
| 354 | PFKP | 42.07% | 14.99% | −0.31 | |
| 355 | PXK | 42.05% | 14.69% | −0.31 | |
| 356 | PI4K2B | 42.05% | 11.84% | −0.31 | |
| 357 | PIP5K2C | 42.02% | 9.50% | −0.31 | |
| 358 | PFKFB3 | 42.00% | 12.79% | −0.31 | |
| 359 | TSSK3 | 41.97% | 14.82% | −0.32 | |
| 360 | MPP6 | 41.97% | 12.68% | −0.32 | |
| 361 | MPP4 | 41.87% | 12.27% | −0.33 | |
| 362 | LOC653155 | 41.85% | 11.50% | −0.34 | |
| 363 | ALPK1 | 41.82% | 12.37% | −0.34 | |
| 364 | CDK9 | 41.76% | 10.32% | −0.35 | |
| 365 | PDK3 | 41.66% | 10.87% | −0.36 | |
| 366 | CKMT2 | 41.66% | 12.57% | −0.36 | |
| 367 | CAMK1G | 41.63% | 12.06% | −0.37 | |
| 368 | MAPKAPK3 | 41.61% | 13.19% | −0.37 | |
| 369 | PIK4CB | 41.55% | 14.29% | −0.38 | |
| 370 | PRPS1L1 | 41.54% | 11.08% | −0.38 | |
| 371 | FASTK | 41.49% | 12.56% | −0.39 | |
| 372 | CAMK1D | 41.49% | 11.54% | −0.39 | |
| 373 | MARK2 | 41.48% | 14.28% | −0.39 | |
| 374 | PDK4 | 41.43% | 13.43% | −0.39 | |
| 375 | NEK7 | 41.36% | 9.57% | −0.40 | |
| 376 | MAPK4 | 41.34% | 10.83% | −0.41 | |
| 377 | PIK4CA | 41.32% | 11.99% | −0.41 | |
| 378 | JAK1 | 41.31% | 11.56% | −0.41 | |
| 379 | PDXK | 41.30% | 11.93% | −0.41 | |
| 380 | TGFBR2 | 41.25% | 15.85% | −0.42 | |
| 381 | PHKB | 41.25% | 10.81% | −0.42 | |
| 382 | ULK2 | 41.24% | 15.35% | −0.42 | |
| 383 | MKNK1 | 41.21% | 13.08% | −0.42 | |
| 384 | CDC2L6 | 41.17% | 10.91% | −0.43 | |
| 385 | CSNK1G3 | 41.13% | 10.53% | −0.44 | |
| 386 | CAMK1 | 41.08% | 11.68% | −0.44 | |
| 387 | DGKZ | 41.07% | 12.69% | −0.44 | |
| 388 | SGK | 40.91% | 11.92% | −0.47 | |
| 389 | TBK1 | 40.83% | 14.81% | −0.48 | |
| 390 | ILK | 40.81% | 12.62% | −0.48 | |
| 391 | STK32B | 40.80% | 11.79% | −0.48 | |
| 392 | TXNDC3 | 40.78% | 12.24% | −0.48 | |
| 393 | RPS6KB1 | 40.72% | 10.13% | −0.49 | |
| 394 | ZAK | 40.71% | 10.32% | −0.49 | |
| 395 | DYRK4 | 40.66% | 12.59% | −0.50 | |
| 396 | ITGB1BP3 | 40.57% | 11.99% | −0.51 | |
| 397 | MPP1 | 40.53% | 10.94% | −0.52 | |
| 398 | HIPK2 | 40.49% | 11.06% | −0.52 | |
| 399 | MAPK13 | 40.46% | 12.06% | −0.53 | |
| 400 | TK1 | 40.39% | 11.04% | −0.54 | |
| 401 | SH3BP4 | 40.36% | 12.11% | −0.54 | |
| 402 | CKM | 40.29% | 12.70% | −0.55 | |
| 403 | FGFRL1 | 40.23% | 16.94% | −0.56 | |
| 404 | MAPK10 | 40.23% | 12.29% | −0.56 | |
| 405 | CALM2 | 40.16% | 8.64% | −0.57 | |
| 406 | CALM3 | 40.12% | 11.85% | −0.58 | |
| 407 | STYK1 | 40.09% | 11.47% | −0.58 | |
| 408 | CDKL4 | 40.08% | 11.01% | −0.58 | |
| 409 | NADK | 40.08% | 11.89% | −0.58 | |
| 410 | MPP7 | 40.06% | 11.72% | −0.59 | |
| 411 | CAMKV | 40.03% | 12.16% | −0.59 | |
| 412 | EXOSC10 | 40.02% | 12.78% | −0.59 | |
| 413 | CDKL5 | 39.98% | 10.10% | −0.60 | |
| 414 | STK38 | 39.90% | 9.61% | −0.61 | |

TABLE 4-continued

Ranking of average differential proliferation (1 μM PLX4720/control) for 597 kinase-related ORFs, relative to MEK DD

| RANK | GENE | AVERAGE | STDEV. | Z-SCORE | NOTES |
|---|---|---|---|---|---|
| 415 | INSRR | 39.90% | 15.08% | −0.61 | |
| 416 | DCK | 39.86% | 10.23% | −0.61 | |
| 417 | TLK2 | 39.80% | 14.66% | −0.62 | |
| 418 | PCTK3 | 39.66% | 10.48% | −0.64 | |
| 419 | LOC388957 | 39.65% | 10.97% | −0.64 | |
| 420 | PAPSS1 | 39.59% | 13.48% | −0.65 | |
| 421 | ACVR2B | 39.56% | 14.70% | −0.65 | |
| 422 | NME1-NME2 | 39.53% | 12.01% | −0.66 | |
| 423 | NEK10 | 39.50% | 13.78% | −0.66 | |
| 424 | MAP3K11 | 39.47% | 9.33% | −0.67 | |
| 425 | PMVK | 39.46% | 10.19% | −0.67 | |
| 426 | MAPK9 | 39.45% | 12.74% | −0.67 | |
| 427 | MKNK2 | 39.39% | 13.54% | −0.68 | |
| 428 | GRK7 | 39.34% | 14.98% | −0.68 | |
| 429 | RIOK2 | 39.27% | 11.79% | −0.69 | |
| 430 | DGKK | 39.27% | 9.02% | −0.69 | |
| 431 | ACVR1 | 39.15% | 13.96% | −0.71 | |
| 432 | TLK1 | 39.11% | 15.46% | −0.72 | |
| 433 | LATS1 | 39.05% | 10.46% | −0.73 | |
| 434 | SCYL1 | 39.01% | 11.41% | −0.73 | |
| 435 | TESK2 | 38.93% | 13.30% | −0.74 | |
| 436 | DGUOK | 38.90% | 14.54% | −0.75 | |
| 437 | PGK1 | 38.87% | 12.26% | −0.75 | |
| 438 | MAGI1 | 38.87% | 12.66% | −0.75 | |
| 439 | SNRK | 38.79% | 11.61% | −0.76 | |
| 440 | CALM1 | 38.65% | 10.26% | −0.78 | |
| 441 | RIOK1 | 38.58% | 12.39% | −0.79 | |
| 442 | EEF2K | 38.56% | 11.96% | −0.79 | |
| 443 | MAPK8 | 38.45% | 10.51% | −0.81 | |
| 444 | CSNK1D | 38.44% | 15.60% | −0.81 | |
| 445 | ULK4 | 38.42% | 12.02% | −0.81 | |
| 446 | STK38L | 38.33% | 12.63% | −0.83 | |
| 447 | RIOK3 | 38.21% | 12.80% | −0.84 | |
| 448 | MINK1 | 38.00% | 14.94% | −0.87 | |
| 449 | ROR2 | 37.95% | 15.32% | −0.88 | |
| 450 | PTK2 | 37.93% | 10.59% | −0.88 | |
| 451 | PIK3R5 | 37.84% | 13.17% | −0.89 | |
| 452 | ALDH18A1 | 37.81% | 15.66% | −0.90 | |
| 453 | NYD-SP25 | 37.79% | 13.52% | −0.90 | |
| 454 | MAP4K3 | 37.76% | 9.58% | −0.90 | |
| 455 | AGK | 37.61% | 13.89% | −0.92 | |
| 456 | GSK3A | 37.56% | 14.44% | −0.93 | |
| 457 | BMPR1A | 37.56% | 16.10% | −0.93 | |
| 458 | STK16 | 37.53% | 11.09% | −0.94 | |
| 459 | FASTKD2 | 37.50% | 8.53% | −0.94 | |
| 460 | MAP4K4 | 37.39% | 15.68% | −0.96 | |
| 461 | LRRK2 | 37.38% | 10.11% | −0.96 | |
| 462 | TGFBR3 | 37.33% | 11.04% | −0.96 | |
| 463 | PDGFRB | 37.29% | 16.90% | −0.97 | |
| 464 | DLG3 | 37.09% | 12.08% | −1.00 | |
| 465 | PFKFB2 | 36.99% | 10.37% | −1.01 | |
| 466 | AKT1 | 36.66% | 13.43% | −1.06 | |
| 467 | PRKCI | 36.54% | 11.44% | −1.07 | |
| 468 | NEK4 | 36.50% | 13.19% | −1.08 | |
| 469 | PRKD1 | 36.45% | 14.57% | −1.09 | |
| 470 | SRPK2 | 36.37% | 12.38% | −1.10 | |
| 471 | SH3BP5 | 36.37% | 17.17% | −1.10 | |
| 472 | CLK1 | 36.06% | 11.13% | −1.14 | |
| 473 | GK | 35.86% | 17.33% | −1.17 | |
| 474 | IHPK1 | 35.53% | 12.15% | −1.21 | |
| 475 | IHPK3 | 35.48% | 9.30% | −1.22 | |
| 476 | PLAU | 35.36% | 13.10% | −1.24 | |
| 477 | TAOK3 | 35.29% | 14.78% | −1.25 | |
| 478 | PAK2 | 35.20% | 12.51% | −1.26 | |
| 479 | BMX | 35.12% | 12.94% | −1.27 | |
| 480 | DAPK2 | 35.01% | 13.92% | −1.29 | |
| 481 | CSNK1E | 34.83% | 15.21% | −1.31 | |
| 482 | MAPK3 | 34.75% | 19.93% | −1.32 | Lethal |
| 483 | MAP3K15 | 34.40% | 16.76% | −1.37 | Lethal |
| 484 | MPP5 | 34.35% | 11.80% | −1.38 | |
| 485 | MAST2 | 34.08% | 16.10% | −1.42 | |
| 486 | GRK6 | 34.04% | 15.82% | −1.42 | |
| 487 | DKFZp761P0423 | 33.93% | 13.58% | −1.44 | |
| 488 | VRK1 | 33.87% | 9.28% | −1.45 | |
| 489 | DCAMKL2 | 33.77% | 11.96% | −1.46 | |

TABLE 4-continued

Ranking of average differential proliferation (1 μM PLX4720/control) for 597 kinase-related ORFs, relative to MEK DD

| RANK | GENE | AVERAGE | STDEV. | Z-SCORE | NOTES |
|---|---|---|---|---|---|
| 490 | IHPK2 | 33.75% | 9.56% | −1.46 | |
| 491 | MATK | 33.44% | 10.25% | −1.51 | |
| 492 | RP2 | 33.20% | 13.41% | −1.54 | |
| 493 | MAP2K2 | 32.98% | 15.34% | −1.57 | |
| 494 | UCK2 | 32.82% | 13.75% | −1.59 | |
| 495 | NEK6 | 32.74% | 15.85% | −1.60 | |
| 496 | PRKG1 | 32.52% | 14.60% | −1.63 | |
| 497 | MAP3K12 | 32.49% | 15.33% | −1.64 | |
| 498 | PCTK1 | 32.48% | 13.21% | −1.64 | |
| 499 | MGC42105 | 32.36% | 13.85% | −1.66 | |
| 500 | MAP2K6 | 32.32% | 11.92% | −1.66 | |
| 501 | SH3BP5L | 32.11% | 15.55% | −1.69 | |
| 502 | FES | 32.07% | 11.04% | −1.70 | |
| 503 | RKHD3 | 31.89% | 12.45% | −1.72 | |
| 504 | PRKACA | 31.76% | 18.45% | −1.74 | Lethal |
| 505 | MAP4K1 | 31.51% | 13.69% | −1.77 | |
| 506 | CSNK1G1 | 30.32% | 14.90% | −1.94 | |
| 507 | MAPKAPK5 | 30.15% | 13.47% | −1.96 | |
| 508 | CSK | 29.83% | 14.11% | −2.01 | Lethal |
| 509 | BRD3 | 29.16% | 8.83% | −2.10 | |
| 510 | ADRBK1 | 29.00% | 16.93% | −2.12 | |
| 511 | BRSK2 | 28.64% | 13.09% | −2.17 | |
| 512 | ADCK1 | 28.30% | 13.52% | −2.22 | |
| 513 | CSNK1G2 | 26.81% | 14.42% | −2.43 | |
| 514 | CKMT1A | 26.80% | 12.42% | −2.43 | |
| 515 | TSSK2 | 25.66% | 13.30% | −2.59 | Lethal |
| 516 | CD2 | 25.01% | 14.99% | −2.68 | |
| 517 | PIP5K1A | 24.76% | 15.49% | −2.71 | |
| 518 | PHKG1 | 23.31% | 14.24% | −2.91 | |
| 519 | ABL2 | Low pLX DNA yield | | | |
| 520 | ACVR2A | Low pLX DNA yield | | | |
| 521 | BLK | Low pLX DNA yield | | | |
| 522 | CDC2L1 | Low pLX DNA yield | | | |
| 523 | EGFR | Low pLX DNA yield | | | |
| 524 | EPHA3 | Low pLX DNA yield | | | |
| 525 | EPHB1 | Low pLX DNA yield | | | |
| 526 | ERBB4 | Low pLX DNA yield | | | |
| 527 | FASTKD3 | Low pLX DNA yield | | | |
| 528 | FGFR1 | Low pLX DNA yield | | | |
| 529 | FLT3 | Low pLX DNA yield | | | |
| 530 | FLT4 | Low pLX DNA yield | | | |
| 531 | HIPK3 | Low pLX DNA yield | | | |
| 532 | KSR | Low pLX DNA yield | | | |
| 533 | LYN | Low pLX DNA yield | | | |
| 534 | PANK4 | Low pLX DNA yield | | | |
| 535 | PDGFRA | Low pLX DNA yield | | | |
| 536 | PLK4 | Low pLX DNA yield | | | |
| 537 | RET | Low pLX DNA yield | | | |
| 538 | SGK3 | Low pLX DNA yield | | | |
| 539 | SRC | Low pLX DNA yield | | | |
| 540 | TXK | Low pLX DNA yield | | | |
| 541 | BRD4 | Inf. Effic. <70% | | | |
| 542 | CAMKK2 | Inf. Effic. <70% | | | |
| 543 | CKS1B | Inf. Effic. <70% | | | |
| 544 | CLK3 | Inf. Effic. <70% | | | |
| 545 | DAPK3 | Inf. Effic. <70% | | | |
| 546 | EPHA4 | Inf. Effic. <70% | | | |
| 547 | EPHB6 | Inf. Effic. <70% | | | |
| 548 | FGFR3 | Inf. Effic. <70% | | | |
| 549 | FRK | Inf. Effic. <70% | | | |
| 550 | GCK | Inf. Effic. <70% | | | |
| 551 | GNE | Inf. Effic. <70% | | | |
| 552 | HIPK4 | Inf. Effic. <70% | | | |
| 553 | ITK | Inf. Effic. <70% | | | |
| 554 | KDR | Inf. Effic. <70% | | | |
| 555 | LOC389599 | Inf. Effic. <70% | | | |
| 556 | LOC649288 | Inf. Effic. <70% | | | |
| 557 | MAP3K2 | Inf. Effic. <70% | | | |
| 558 | NEK5 | Inf. Effic. <70% | | | |
| 559 | NTRK1 | Inf. Effic. <70% | | | |
| 560 | PAK1 | Inf. Effic. <70% | | | |
| 561 | PHKG2 | Inf. Effic. <70% | | | |
| 562 | PIK3CA | Inf. Effic. <70% | | | |
| 563 | PIK3R3 | Inf. Effic. <70% | | | |
| 564 | PIP5K1B | Inf. Effic. <70% | | | |

TABLE 4-continued

Ranking of average differential proliferation (1 µM PLX4720/control) for 597 kinase-related ORFs, relative to MEK DD

| RANK | GENE | AVERAGE | STDEV. | Z-SCORE | NOTES |
|---|---|---|---|---|---|
| 565 | RIPK1 | | Inf. Effic. <70% | | |
| 566 | RIPK2 | | Inf. Effic. <70% | | |
| 567 | RPS6KA2 | | Inf. Effic. <70% | | |
| 568 | RPS6KC1 | | Inf. Effic. <70% | | |
| 569 | STK17B | | Inf. Effic. <70% | | |
| 570 | TGFBR1 | | Inf. Effic. <70% | | |
| 571 | UHMK1 | | Inf. Effic. <70% | | |
| 572 | XRCC6BP1 | | Inf. Effic. <70% | | |
| 573 | BCKDK | | Replicate STDEV | | |
| 574 | C1orf57 | | Replicate STDEV | | |
| 575 | CAMKK1 | | Replicate STDEV | | |
| 576 | CDC2L2 | | Replicate STDEV | | |
| 577 | CDK5 | | Replicate STDEV | | |
| 578 | ERBB3 | | Replicate STDEV | | |
| 579 | GSG2 | | Replicate STDEV | | |
| 580 | LOC647279 | | Replicate STDEV | | |
| 581 | LYK5 | | Replicate STDEV | | |
| 582 | MAPK1 | | Replicate STDEV | | Lethal |
| 583 | MAP2K5 | | Replicate STDEV | | |
| 584 | MAP4K2 | | Replicate STDEV | | |
| 585 | NUAK2 | | Replicate STDEV | | |
| 586 | PDK2 | | Replicate STDEV | | Lethal |
| 587 | PFKM | | Replicate STDEV | | |
| 588 | PIK3R1 | | Replicate STDEV | | |
| 589 | PLK2 | | Replicate STDEV | | |
| 590 | PRKAR2A | | Replicate STDEV | | |
| 591 | RPS6KA3 | | Replicate STDEV | | |
| 592 | RPS6KA6 | | Replicate STDEV | | |
| 593 | SGK2 | | Replicate STDEV | | |
| 594 | SRPK3 | | Replicate STDEV | | |
| 595 | VRK1 | | Replicate STDEV | | |
| 596 | VRK2 | | Replicate STDEV | | |
| 597 | VRK3 | | Replicate STDEV | | |
| | A375 | | | SKMEL28 | |

TABLE 5

Results of a secondary screen quantifying the change in PLX4720 $GI_{50}$ induced by the top 9 candidate resistance ORFs Secondary Screen

| Gene | $GI_{50}$ (µM) | Fold Change $GI_{50}$ | Rank | Gene | GI50 (µM) | Fold Change $GI_{50}$ | Rank |
|---|---|---|---|---|---|---|---|
| A375 | | | | SKMEL28 | | | |
| MAP3K8 | >100.0 | 598 | 1 | MAP3K8 | >100.0 | ~100 | 1 |
| RAF1 | ≥100.0 | 598 | 2 | RAF1 | ≥10.0 | ≥10 | 2 |
| CRKL | >10.0 | 59.8 | 3 | CRKL | 9.7 | 9.7 | 3 |
| FGR | >10.0 | 59.8 | 4 | FGR | 5 | 5 | 4 |
| PRKCE | 4.41 | 26.4 | 5 | PRKCH | 2.26 | 2.26 | 5 |
| PRKCH | 4.14 | 24.7 | 6 | PRKCE | 1.91 | 1.91 | 6 |
| ERBB2 | 1.33 | 7.95 | 7 | AXL | 1.18 | 1.18 | 7 |
| AXL | 1 | 5.98 | 8 | ERBB2 | 1 | 1 | 8 |
| PAK3 | 0.4934 | 2.95 | 9 | PAK3 | 0.9041 | 0.9041 | 9 |
| Controls | | | | Controls | | | |
| Mock | 0.1528 | 0.91 | | Mock | 0.5287 | 1.89 | |
| MEK1 | 0.1671 | 1 | (−) | MEK1 | 1 | 1 | (−) |
| MEK DD | 4.8 | 28 | (+) | MEK DD | 8.29 | 8.29 | (+) |

TABLE 6

Patient characteristics

| Patient | Tissue | Age (years) | Gender | Biopsy Location | Time from primary diagnosis (years) | Time from metastatic disease diagnosis (years) | Response | BRAF status (pre-treatment) | BRAF status (on-treatment/ post-relapse) | NRAS status | KRAS status | pMEK status | pERK status |
|---|---|---|---|---|---|---|---|---|---|---|---|---|---|
| Pt 1 | Tissue Biopsy | 49 | F | Back | 5 | 3 | Partial Response | V600E | N/A | N/A | N/A | N/A | N/A |
| Pt 2 | Tissue Biopsy | 67 | M | Back | 2 | 0 | Partial Response | V600E | N/A | N/A | N/A | N/A | N/A |
| Pt 3 | Tissue Biopsy | 68 | M | Leg | 11 | 0 | Partial Response | V600E | N/A | N/A | N/A | N/A | N/A |
| MM-R | Tissue Biopsy | 38 | M | Axilla | 0 | 0 | Partial Response | V600E | V600E | WT | WT | * | * |
| M307 | Short-term Culture | 59 | M | Axillary Lymph node | 4 | 4 | Stable Disease | V600E | V600E | N/A | N/A | Ref. (14) | ** |

Figure 20A:
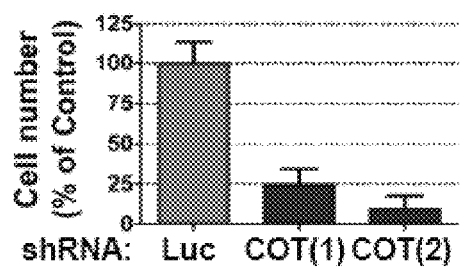
FIGS. 20A-20B illustrate that depletion of COT affects viability in the COT amplified cell line RPMI-7951. (a) Quantification of RPMI-7951 viability following lentiviral shRNA-mediated COT depletion (shCOT), relative to control shRNA (shLuc). Error bars represent standard deviation between replicates. (b) Immunoblot analysis showing relative COT protein expression in shLuc and shCOT-expressing RPMI-7951.
Figure 20B:
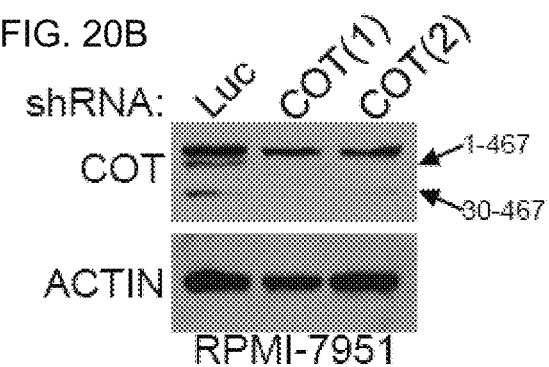

* See FIG. 20
** See FIG. 3f

The invention claimed is:

1. A method of treating cancer in a first subject in need thereof, comprising
administering to the first subject an effective amount of a RAF inhibitor selected from the group consisting of RAF265, sorafenib, SB590885, PLX 4720, PLX4032, GDC-0879 and ZM 336372, and an effective amount of a second inhibitor,
wherein the second inhibitor is a MAP3K8 (TPL2/COT) inhibitor selected from the group consisting of 4-(3-chloro-4-fluorophenylamino)-6-(pyridin-3-ylmethyl-amino)-3-cyano-[1,7]-naphthyridine, the inhibitory RNA of SEQ ID NO: 16, and the inhibitory RNA of SEQ ID NO: 17.

2. The method of claim 1, wherein the cancer in the first subject has cancer cells comprising a BRAF mutation or a B-RAFV600E mutation.

3. The method of claim 2, wherein the cancer in the first subject has cancer cells comprising a B-RAFV600E mutation.

4. The method of claim 1, further comprising assaying a gene copy number, a mRNA or a protein level or phosphorylation of one or more kinase targets selected from the group consisting of MAP3K8 (TPL2/COT), RAF1 (CRAF), CRKL(CrkL), FGR (Fgr), PRKCE (Prkce), PRKCH (Prkch), ERBB2 (ErbB2), AXL (Axl), and PAK3 (Pak3) in cancer cells obtained from the first subject and comparing the gene copy number, the mRNA or the protein level or the phosphorylation with a gene copy number, a mRNA or a protein level or phosphorylation of the target kinase in cells obtained from a second subject without the cancer; and
administering the effective amount of the RAF inhibitor and the effective amount of the second inhibitor to the first subject having an increased gene copy number or an alteration in mRNA expression or protein overexpression or phosphorylation of the target kinase in the cancer cells obtained from the first subject relative to the cells obtained from a second subject without the cancer.

5. The method of claim 1, wherein the first subject has innate resistance to the RAF inhibitor.

6. The method of claim 1, wherein the cancer is selected from the group consisting of melanoma, breast cancer, colorectal cancers, glioma, lung cancer, ovarian cancer, sarcoma and thyroid cancer.

7. The method of claim 1, wherein the cancer is melanoma.

8. A method of treating cancer in a first subject in need thereof, the method comprising:
identifying a first subject having an increased gene copy number or an alteration in mRNA expression or protein overexpression or phosphorylation of one or more kinase targets in cancer cells of the first subject relative to cells of a second subject without the cancer, the one or more kinase targets selected from the group consisting of MAP3K8 (TPL2/COT), CRKL(CrkL), FGR (Fgr), PRKCE (Prkce), PRKCH (Prkch), ERBB2 (ErbB2), AXL (Axl), and PAK3 (Pak3); and
administering to the first subject an effective amount of a RAF inhibitor selected from the group consisting of RAF265, sorafenib, SB590885, PLX 4720, PLX4032, GDC-0879 and ZM 336372, and an effective amount of a second inhibitor, wherein the second inhibitor is a MAP3K8 (TPL2/COT) inhibitor selected from the group consisting of 4-(3-chloro-4-fluorophenylamino)-6-(pyridin-3-ylmethylamino)-3-cyano-[1,7]-naphthyridine, the inhibitory RNA of SEQ ID NO: 16, and the inhibitory RNA of SEQ ID NO: 17.

9. The method of claim 8, wherein the subject has innate resistance to the RAF inhibitor.

10. The method of claim 8, wherein the cancer is selected from the group consisting of melanoma, breast cancer, colorectal cancers, glioma, lung cancer, ovarian cancer, sarcoma and thyroid cancer.

11. The method of claim 8, wherein the cancer is melanoma.

12. The method of claim 8, wherein the first subject has cancer cells comprising a B-RAFV600E mutation.

* * * * *